US006956371B2

(12) United States Patent
Prammer

(10) Patent No.: US 6,956,371 B2
(45) Date of Patent: Oct. 18, 2005

(54) METHOD AND APPARATUS FOR DETECTING DIFFUSION SENSITIVE PHASES WITH ESTIMATION OF RESIDUAL ERROR IN NMR LOGS

(75) Inventor: Manfred Prammer, Downingtown, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 11 days.

(21) Appl. No.: 10/352,763

(22) Filed: Jan. 28, 2003

(65) Prior Publication Data

US 2004/0008027 A1 Jan. 15, 2004

Related U.S. Application Data

(63) Continuation-in-part of application No. 09/874,028, filed on Jun. 5, 2001, now Pat. No. 6,512,371, which is a continuation-in-part of application No. 08/822,567, filed on Mar. 19, 1997, now Pat. No. 6,242,912, which is a continuation of application No. 08/542,340, filed on Oct. 12, 1995, now abandoned.

(51) Int. Cl.[7] .............................................. G01V 3/00
(52) U.S. Cl. ...................................... 324/303; 324/300
(58) Field of Search ................................ 324/303, 300, 324/322, 318, 309, 307, 301

(56) References Cited

U.S. PATENT DOCUMENTS

| | | | |
|---|---|---|---|
| 2,973,471 A | 2/1961 | Armistead et al. | |
| 3,205,477 A | 9/1965 | Kalbfell | |
| 3,213,357 A | 10/1965 | Brown et al. | |

(Continued)

FOREIGN PATENT DOCUMENTS

| | | | | |
|---|---|---|---|---|
| EP | 0 295 134 A2 | 12/1988 | ............ | G01V/3/32 |
| EP | 0 581 666 A3 | 2/1994 | ............ | G01V/3/32 |
| EP | 0 649 035 B1 | 4/1995 | ............ | G01V/3/32 |
| GB | 2 056 082 A | 7/1980 | .......... | G01N/24/08 |
| WO | WO 92/10768 | 6/1992 | ............ | G01V/3/32 |
| WO | WO 98/25164 | 6/1998 | ............ | G01V/3/32 |

OTHER PUBLICATIONS

Akkurt et al., "NMR Logging of Natural Gas Reservoirs," SPWLA 36th Annual Logging Symposium (Jun. 26–29, 1995).
Akkurt et al., "Selection of Optimal Acquistion Parameters for MRIL Logs," SPWLA 37th Annual Logging Symposium, Jun. 16–19, 1996.

(Continued)

*Primary Examiner*—Brij Shrivastav
(74) *Attorney, Agent, or Firm*—Jones Day

(57) ABSTRACT

A method and system are disclosed for NMR echo-train data acquisition and processing for enhanced tracking of the error in the signal due to magnetoacoustic effects, known as ringing, that are not cancelled out or otherwise corrected. In one aspect, the method enables correction of ringing signals in a single pass by way of collecting a composite signal that includes echoes due to pulses at least at two different frequencies. The choice of one or more of the frequencies, the phase of the pulses, and the recovery period enable cancellation of the ringing signal from the echoes, including the echo from an excitation pulse. In another aspect, the method encompasses providing protection against errors due to tool motion by saturating a relatively wide sensitive region with the echo signals collected from within this relatively wide sensitive signal. Preferred embodiments of the invention include one or more of the aforementioned aspects.

23 Claims, 36 Drawing Sheets

U.S. PATENT DOCUMENTS

| | | |
|---|---|---|
| 3,360,716 A | 12/1967 | Bloom et al. |
| 3,395,337 A | 7/1968 | Varian |
| 3,402,344 A | 9/1968 | Brown et al. |
| 3,453,433 A | 7/1969 | Alger et al. ............... 250/83.3 |
| 3,508,438 A | 4/1970 | Alger et al. .................. 73/152 |
| 3,567,935 A | 3/1971 | Nagel ........................ 250/83.1 |
| 3,567,936 A | 3/1971 | Tittman ..................... 250/83.1 |
| 3,590,228 A | 6/1971 | Burke ................... 235/151.35 |
| 3,593,116 A | 7/1971 | Culpepper .................. 324/0.5 |
| 3,617,867 A | 11/1971 | Herzog ....................... 324/0.5 |
| 3,638,484 A | 2/1972 | Tixier .......................... 73/152 |
| 3,657,730 A | 4/1972 | Robinson et al. ............ 324/0.5 |
| 3,667,035 A | 5/1972 | Slichter ................... 324/0.5 R |
| 3,777,560 A | 12/1973 | Guignard ................... 73/151.5 |
| 3,784,898 A | 1/1974 | Darley et al. ............ 324/0.5 R |
| 3,896,668 A | 7/1975 | Anderson et al. ............. 73/152 |
| 4,291,271 A | 9/1981 | Lauffer ........................ 324/307 |
| 4,310,887 A | 1/1982 | Suau ........................... 364/422 |
| 4,350,955 A | 9/1982 | Jackson et al. ............. 324/303 |
| 4,479,564 A | 10/1984 | Tanguy ........................ 181/105 |
| 4,528,508 A | 7/1985 | Vail, III ...................... 324/303 |
| 4,536,714 A | 8/1985 | Clark .......................... 324/338 |
| 4,629,986 A | 12/1986 | Clow et al. ................. 324/303 |
| 4,656,422 A | 4/1987 | Vail, III et al. ............. 324/303 |
| 4,686,364 A | 8/1987 | Herron ........................ 250/256 |
| 4,707,658 A | 11/1987 | Frahm et al. ............... 324/309 |
| 4,710,713 A | 12/1987 | Strikman .................... 324/303 |
| 4,714,881 A | 12/1987 | Givens ........................ 324/303 |
| 4,717,876 A | 1/1988 | Masi et al. .................. 324/303 |
| 4,717,877 A | 1/1988 | Taicher et al. .............. 324/303 |
| 4,717,878 A | 1/1988 | Taicher et al. .............. 324/303 |
| 4,728,892 A | 3/1988 | Vinegar et al. ............. 324/309 |
| 4,785,245 A | 11/1988 | Lew et al. ................... 324/308 |
| 4,792,757 A | 12/1988 | Vail, III et al. ............. 324/303 |
| RE32,913 E | 4/1989 | Clark .......................... 324/338 |
| 4,825,163 A | 4/1989 | Yabusaki et al. ........... 324/318 |
| 4,829,252 A | 5/1989 | Kaufman .................... 324/309 |
| 4,875,013 A | 10/1989 | Murakami et al. .......... 324/318 |
| 4,885,540 A | 12/1989 | Snoddy et al. .............. 324/318 |
| 4,899,112 A | 2/1990 | Clark et al. ................. 324/338 |
| 4,933,638 A | 6/1990 | Kleinberg et al. .......... 324/303 |
| 4,933,640 A | 6/1990 | Kuckes ........................ 324/339 |
| 4,939,648 A | 7/1990 | O'Neill et al. .............. 364/422 |
| 4,949,045 A | 8/1990 | Clark et al. ................. 324/338 |
| 4,987,368 A | 1/1991 | Vinegar ....................... 324/303 |
| 4,994,777 A | 2/1991 | Leupold et al. ............. 335/302 |
| 5,023,551 A | 6/1991 | Kleinberg et al. .......... 324/303 |
| 5,055,787 A | 10/1991 | Kleinberg et al. .......... 324/303 |
| 5,055,788 A | 10/1991 | Kleinberg et al. .......... 324/303 |
| 5,086,275 A | 2/1992 | Roemer ....................... 324/309 |
| 5,122,746 A | 6/1992 | King et al. .................. 324/307 |
| 5,138,263 A | 8/1992 | Towle ......................... 324/338 |
| 5,200,699 A | 4/1993 | Baldwin et al. ............. 324/303 |
| 5,212,447 A | 5/1993 | Paltiel ......................... 324/300 |
| 5,235,285 A | 8/1993 | Clark et al. ................. 324/342 |
| 5,280,243 A | 1/1994 | Miller ......................... 324/303 |
| 5,291,137 A | 3/1994 | Freedman ................... 324/303 |
| 5,309,098 A | 5/1994 | Coates et al. ............... 324/303 |
| 5,349,184 A | 9/1994 | Wraight ...................... 250/266 |
| 5,350,925 A | 9/1994 | Watson .................... 250/269.3 |
| 5,359,324 A | 10/1994 | Clark et al. ............... 340/854.3 |
| 5,363,041 A | 11/1994 | Sezginer ..................... 324/303 |
| 5,365,171 A | 11/1994 | Buess et al. ................ 324/307 |
| 5,376,884 A | 12/1994 | Sezginer ..................... 324/303 |
| 5,379,216 A | 1/1995 | Head ........................... 364/422 |
| 5,381,092 A | 1/1995 | Freedman ................... 324/303 |
| 5,387,865 A | 2/1995 | Jerosch-Herold et al. ... 324/303 |
| 5,397,989 A | 3/1995 | Spraul et al. ............... 324/321 |
| 5,412,320 A | 5/1995 | Coates ........................ 324/303 |
| 5,432,446 A | 7/1995 | Macinnis et al. ........... 324/303 |
| 5,453,692 A | 9/1995 | Takahashi et al. .......... 324/318 |
| 5,486,761 A | 1/1996 | Sezginer ..................... 324/303 |
| 5,486,762 A | 1/1996 | Freedman et al. .......... 324/303 |
| 5,497,087 A | 3/1996 | Vinegar et al. ............. 324/303 |
| 5,498,960 A | 3/1996 | Vinegar et al. ............. 324/303 |
| 5,517,115 A | 5/1996 | Prammer .................... 324/303 |
| 5,557,200 A | 9/1996 | Coates ........................ 324/303 |
| 5,557,201 A | 9/1996 | Kleinberg et al. .......... 324/303 |
| 5,565,775 A | 10/1996 | Stallmach et al. .......... 324/303 |
| 5,585,720 A | 12/1996 | Edwards ..................... 324/309 |
| 5,629,623 A | 5/1997 | Sezginer et al. ............ 324/303 |
| 5,680,043 A | 10/1997 | Hurlimann et al. ......... 324/303 |
| 5,696,448 A | 12/1997 | Coates et al. ............... 324/303 |
| 5,705,927 A | 1/1998 | Sezginer et al. ............ 324/303 |
| 5,757,186 A | 5/1998 | Taicher et al. .............. 324/303 |
| 5,767,674 A | 6/1998 | Griffin et al. ............... 324/303 |
| 5,796,252 A | 8/1998 | Kleinberg et al. .......... 324/303 |
| 5,869,755 A | 2/1999 | Ramamoorthy et al. . 73/152.05 |
| 5,914,598 A | 6/1999 | Sezginer et al. ............ 324/303 |
| 5,923,167 A | 7/1999 | Chang et al. ................ 324/303 |
| 5,936,405 A | 8/1999 | Prammer et al. ........... 324/303 |
| 5,977,768 A | 11/1999 | Sezginer et al. ............ 324/303 |
| 5,992,519 A | 11/1999 | Ramakrishnan et al. ..................... 166/250.15 |
| 6,005,389 A | 12/1999 | Prammer .................... 324/303 |
| 6,008,646 A | 12/1999 | Griffin et al. ............... 324/303 |
| 6,023,163 A | 2/2000 | Flaum et al. ................ 324/303 |
| 6,049,205 A | 4/2000 | Taicher et al. .............. 324/303 |
| 6,084,408 A * | 7/2000 | Chen et al. .................. 324/303 |
| 6,111,408 A | 8/2000 | Blades et al. ............... 324/303 |
| 6,115,671 A | 9/2000 | Fordham et al. ................ 702/8 |
| 6,121,774 A | 9/2000 | Sun ............................. 324/303 |
| 6,133,734 A | 10/2000 | McKeon ..................... 324/303 |
| 6,140,817 A | 10/2000 | Flaum et al. ................ 324/303 |
| 6,163,153 A | 12/2000 | Reiderman et al. ......... 324/314 |
| 6,204,663 B1 * | 3/2001 | Prammer .................... 324/303 |
| 6,229,308 B1 * | 5/2001 | Freedman ................... 324/303 |
| 6,242,912 B1 | 6/2001 | Prammer et al. ........... 324/303 |
| 6,246,236 B1 | 6/2001 | Poitzsch et al. ............. 324/303 |
| 6,253,155 B1 | 6/2001 | Hagiwara ....................... 702/9 |
| 6,255,819 B1 | 7/2001 | Day et al. .................... 324/303 |
| 6,268,726 B1 | 7/2001 | Prammer et al. ........... 324/303 |
| 6,326,785 B1 * | 12/2001 | Kruspe ........................ 324/303 |
| 6,388,441 B1 * | 5/2002 | Chen ........................... 324/303 |
| 6,512,371 B2 | 1/2003 | Prammer .................... 324/303 |
| 6,525,534 B2 * | 2/2003 | Akkurt et al. ............... 324/303 |
| 6,541,969 B2 * | 4/2003 | Sigal et al. .................. 324/303 |

OTHER PUBLICATIONS

Brown et al., "Nuclear Magnetism Logging," Transactions of the American Institute of Mining, Metallurgical and Petroleum Engineers, vol. 219 (1960), pp. 199–207.

Brownstein et al., "Importance of classical diffusion in NMR studies of water in biological cells," The American Physical Society, vol. 19, No. 6, (1979) pp. 2446–2453.

Cannon et al., "Quantitative NMR Interpretation," Society of Petroleum Engineers, SPE 49010, 1998.

Carr et al., "Effects of Diffusion on Free Precision in Nuclear Magnetic Resonance Experiments," *Physical Review*, vol. 94. No. 3 (May 1, 1954), pp. 630–638.

Chandler et al., "Improved Log Quality with a Dual–Frequency Pulsed NMR Tool," Society of Petroleum Engineers (1994) pp. 23–35.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Chen et al., "Estimation of Hydrocarbon Viscosity with Multiple TE Dual Wait–Time MRIL Logs," Society of Petroleum Engineers, SPE 49009, 1998.

Chen et al., "Improving the Accuracy of NMR Relaxation Distribution Analysis in Clay–Rich Reservoirs and Core Samples," paper SCA 9702, in 1997 international symposium proceedings: Society of Professional Well Log Analysts, Society of Core Analysts Chapter–at–large, p. 10, 1997.

Clavier et al., "Theoretical and Experimental Bases for the Dual–Water Model for Interpretation of Shaly Sands," Society of Petroleum Engineers Journal, 1984, pp. 153–168.

Coates et al., "A New Approach to Improved Log–Derived Permeability," SPWLA Fourteenth Annual Logging Symposium, May 6–9, 1973, pp. 1–27.

Coates et al., "An Investigation of a New Magnetic Resonance Imaging Log," National SPWLA Convention (Jun. 18, 1991), pp. 1–24.

Coates et al., "Applying NMR Total and Effective Porosity to Formation Evaluation," Society of Petroleum Engineers, Inc., SPE 38736, 1997.

Coates et al., "Core Data and the MRIL Show—A New Approach to 'Formation Factor,'" National SPWLA Convention (Jun. 15, 1992), pp. 1–15.

Coates et al., "The Magnetic Resonance Imaging Log Characterized by Comparison With Petrophysical Properties and Laboratory Core Data," Society of Petroleum Engineers, SPE 22723, 1991, pp. 627–635.

Dunn et al., "A Method for Inverting NMR Data Sets Wtih Different Signal to Noise Ratios," SPWLA 39th Annual Logging Symposium, May 26–29, 1998.

Edwards et al., "Effects of Tool Design and Logging Speed on $T_2$ NMR Log Data," SPWLA 38th Annual Logging Symposium Jun. 15–18, 1997.

Edwards et al., "Improved NMR Well Logs From Time–Dependent Echo Filtering," SPWLA 37th Annual Logging Symposium, Jun. 16–19, 1996.

Farrar et al., "Pulse and Fourier Transform NMR Introduction to Theory and Methods," Academic Press (1971) pp. 26–29.

Freedman et al., "Combining NMR and Density Logs for Petrophysical Analysis in Gas–Bearing Formations," SPWLA 39th Annual Logging Symposium, May 26–29, 1998.

Gallegos et al., "A NMR Technique for the Analysis of Pore Structure: Determination of Continuous Pore Size Distributions," Journal of Collid and Interface Science, vol. 122, No. 1, Mar. 1988, pp. 143–153.

Gallegos et al., "A NMR Technique for the Analysis of Pore Structure: Application to Materials with Well–Defined Pore Structure," Journal of Colloid and Interface Science, vol. 119, No. 1, Sep. 1987, pp. 127–140.

Herrick et al., "An Improved Nuclear Magnetism Logging System and its Application to Formation Evaluation," Society of Petroleum Engineers, SPE 8361, 1979.

Hou et al., "Nuclear Magnetic Resonance Logging Methods for Fluid Typing," Society of Petroleum Engineers, Inc., SPE 48896, 1998.

Howard et al., "Proton Magnetic Resonance and Pore–Size Variations in Reservoir Sandstones," *Society of Petroleum Engineers* (1990), pp. 733–741.

Hull et al., "Field Examples of Nuclear Magnetism Logging," Journal of Petroleum Technology, 1960, pp. 14–22.

Jackson et al., "Nuclear Magnetic Resonance Well Logging," The Log Analyst, Sep.–Oct., 1984, pp. 16–30.

Jackson et al., "Western Gas Sands Project Los Alamos NMR Well Logging Tool Development," Los Alamos National Laboratory (Oct. 1981—Sep. 1982) pp. 1–28.

Kenyon et al., "Pore–Size Distribution and NMR in Microporous Cherty Sandstones," SPWLA Thirtieth Annual Logging Symposium (Jun. 11–14, 1989), pp. 1–24.

Kleinberg et al., "NMR Properties of Reservoir Fluids," The Log Analyst, Nov.–Dec. 1996, pp. 20–32.

Kleinberg et al., "Novel NMR Apparatus for Investigating an External Sample," *Journal of Magnetic Resonance*, (1992) pp. 466–485.

Kleinberg et al., "Nuclear Magnetic Resonance of Rocks: $T_1$ vs. $T_2$," Society of Petroleum Engineers, SPE 26470, 1993, pp. 553–563.

Menger et al., "A New Algorithm for Analysis of NMR Logging Data," Society of Petroleum Engineers, Inc., SPE 49013, 1998.

Miller et al., "Spin Echo Magnetic Resonance Logging: Porosity and Free Fluid Index Determination," *Society of Petroleum Engineers*, SPE 20561 (1990), pp. 321–334.

Morriss et al., "Field Test of an Experimental Pulsed Nuclear Magnetism Tool," SPWLA Annual Logging Symposium (Jun. 13–16, 1993), pp. 1–23.

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Nascimento et al., "Anomalous NMR Responses in Highly Permeable Sandstone Reservoirs: A Case Study," SPWLA 40th Annual Logging Symposium, May 30–Jun. 3, 1999.

Neuman et al., "Applications of Nuclear Magnetism Logging to Formation Evaluation," Journal of Petroleum Technology, vol. 34, (1982) pp. 2853–2862.

Petrakis et al., "The Utilization of Nuclear Magnetic Resonance Spectroscopy for Petroleum, Coal, Oil Shale, Petrochemicals, and Polymers. Phenomenology, Paradigms of Applications, and Instrumentation," 594 Applied Spectroscopy Reviews vol. 15 (1979) No. 2, pp. 195–260.

Prammer et al., "A New Multiband Generation of NMR Logging Tools," Society of Petroleum Engineers, SPE 49011, 1998.

Prammer et al., "Measurements of Clay–Bound Water and Total Porosity by Magnetic Resonance Logging," Society of Petroleum Engineers, SPE 36522, 1996.

Prammer et al., "Theory and Operation of a New, Multi–Volume, NMR Logging System," SPWLA 40th Annual Logging Symposium, May 30–Jun. 3, 1999.

Prammer, M.G., "NMR Pore Size Distributions and Permeability at the Well Site," *Society of Petroleum Engineers*, SPE 28368, (1994) pp. 55–64.

*Schlumberger Technology News—Oilfield Bulletin*, "Fifth Generation Nuclear Magnetic Resonance Logging Tool: A Major Advance in Producibility Measurement Technology," (Jul. 1995) (2 pp.).

*Schlumberger Wireline & Testing*, "Combinable Magnetic Resonance tool reliably indicates water–free production and reveals hard–to–find pay zones," (Jun. 1995).

Singer et al., "Fast NMR Logging for Bound Fluid and Permeability," SPWLA 38th Annual Logging Symposium, Jun. 15–18, 1997.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Tang et al., "LP–ZOOM, a Linear Prediction Method for Local Spectral Analysis of NMR Signals," Journal of Magnetic Resonance 79, 190–196 (1988).

Waxman et al., "Electrical Conductivities in Oil–Bearing Shaly Sands," *Society of Petroleum Engineers Journal* (1968) pp. 107–122.

Güven, "Molecular Aspects of Clay–Water Interactions," CMS Workshop Lectures, vol. 4.

Regrim, "Chapter 8: Clay–Water System," In *Clay Mineralogy*, $2^{nd}$ Ed. 1968.

* cited by examiner

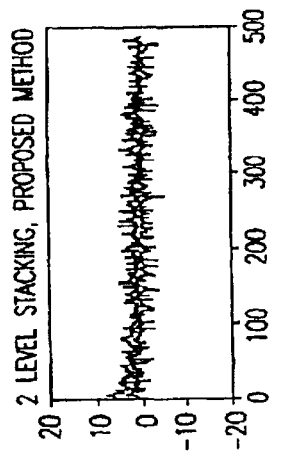
FIG.5A UNSTACKED, PROPOSED METHOD
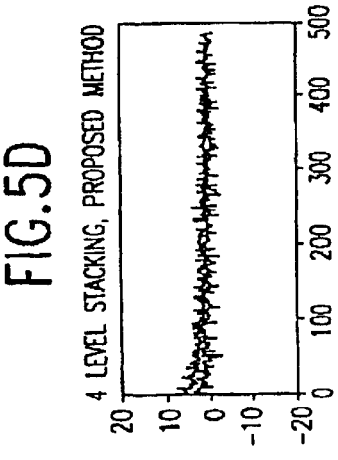
FIG.5B 16 LEVEL STACKING, CURRENT METHOD
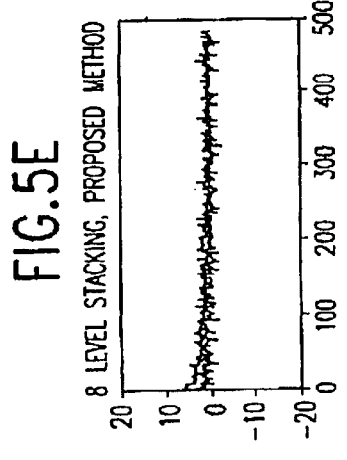
FIG.5C 16 LEVEL STACKING, PROPOSED METHOD
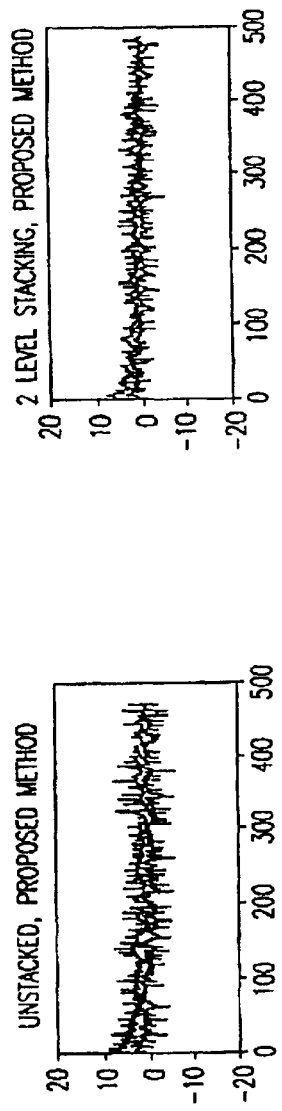
FIG.5D 2 LEVEL STACKING, PROPOSED METHOD
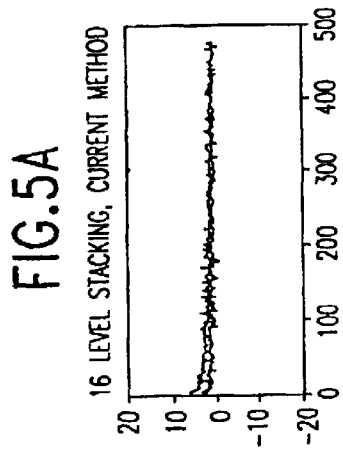
FIG.5E 4 LEVEL STACKING, PROPOSED METHOD
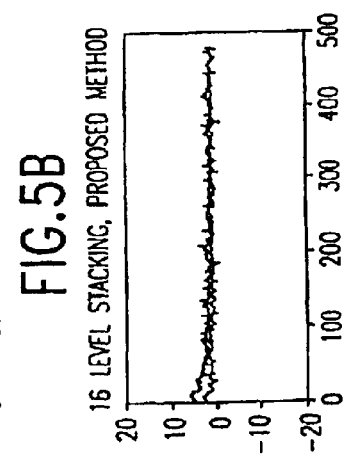
FIG.5F 8 LEVEL STACKING, PROPOSED METHOD SEQUENTIAL PAPs OVERLAPPING PAPs

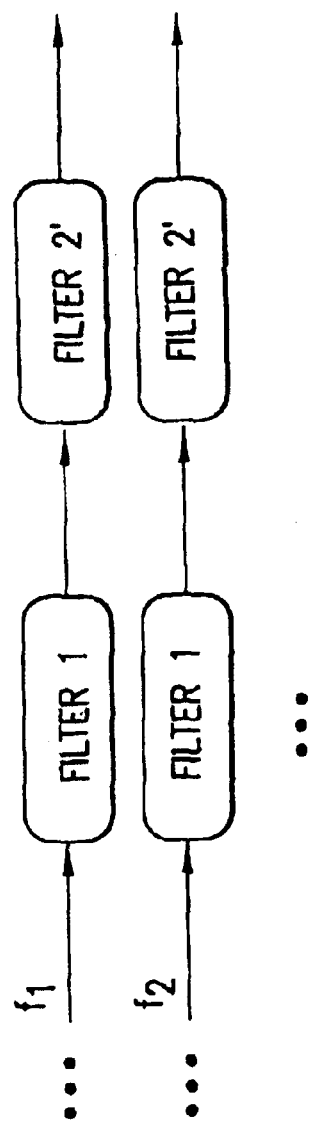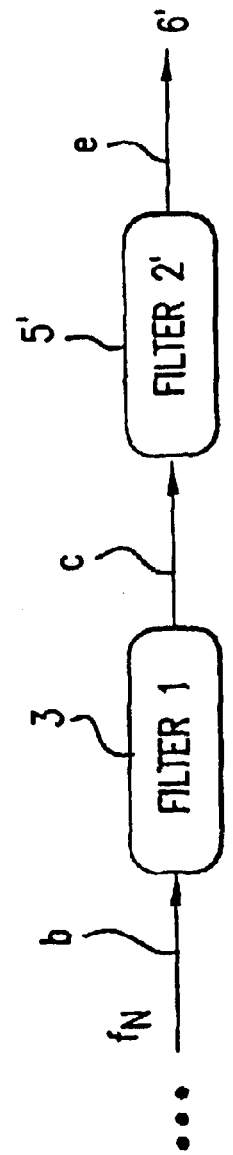

FREQ. 1: $E_x - R_y - A_{11} - R_y - A_{21} - R_y - A_{31} - R_y -$ etc.

FREQ. 2: $E_x - R_y - A_{12} - R_y - A_{22} - R_y - A_{32} - R_y -$ etc.

FREQ. 1: $E_x - R_{-y} - A_{13} - R_{-y} - A_{23} - R_{-y} - A_{33} - R_{-y} -$ etc.

FREQ. 2: $E_x - R_{-y} - A_{14} - R_{-y} - A_{24} - R_{-y} - A_{34} - R_{-y} -$ etc.

NEW MEASUREMENT CYCLE

FIG. 25

METHOD AND APPARATUS FOR DETECTING DIFFUSION SENSITIVE PHASES WITH ESTIMATION OF RESIDUAL ERROR IN NMR LOGS

REFERENCE TO RELATED APPLICATIONS AND PATENTS

This application is a continuation-in-part of and claims the benefit of the U.S. patent application Ser. No. 09/874,028, filed on Jun. 5, 2001 now U.S. Pat No. 6,512,371, which is a continuation-in-part of the U.S. patent application Ser. No. 08/822,567, filed on Mar. 19, 1997 and issued as U.S. Pat. No. 6,242,912, which is a continuation of U.S. patent application Ser. No. 08/542,340 filed on Oct. 12, 1995, now abandoned, all of which applications and issued patents are incorporated herein by reference in their entirety for all purposes. This application also incorporates by reference in its entirety for all purposes the U.S. patent application Ser. No. 09/736,754, filed on Dec. 14, 2000.

FIELD OF THE INVENTION

The present invention concerns nuclear magnetic resonance (NMR) logging and more specifically relates to a method and apparatus for NMR data acquisition and processing. More particularly, the present invention relates to diffusion measurement, non-formation signal error detection and correction, and to providing improved vertical resolution of data logs acquired using NMR logging tools. The present invention also encompasses a system and method for detecting, with NMR logging, the presence and estimating the quantity of gaseous and liquid hydrocarbons in the near wellbore zone.

BACKGROUND OF THE INVENTION

In oil and gas exploration it is desirable to understand the structure and properties of the geological formation surrounding a borehole, in order to determine if the formation contains hydrocarbon resources (oil and/or gas), to estimate the amount and producibility of hydrocarbon contained in the formation, and to evaluate the best options for completing the well in production. A significant aid in this evaluation is the use of wireline logging and/or logging-while-drilling (LWD) measurements of the formation surrounding the borehole (referred to collectively as "logs" or "log measurements"). Typically, one or more logging tools are lowered into the borehole and the tool readings or measurement logs are recorded as the tools traverse the borehole. These measurement logs are used to infer the desired formation properties.

Petrophysical parameters of a geologic formation which are typically used to determine whether the formation will produce viable amounts of hydrocarbons include the formation porosity PHI, fluid saturation S, the volume of the formation, and its permeability K. Formation porosity is the pore volume per unit volume of formation; it is the fraction of the total volume of a sample that is occupied by pores or voids. The saturation S of a formation is the fraction of a its pore volume occupied by the fluid of interest. Thus, water saturation $S_W$ is the fraction of the pore volume, which contains water. The water saturation of a formation can vary from 100% to a small value, which cannot be displaced by oil, and is referred to as irreducible water saturation $S_{Wirr}$. For practical purposes it can be assumed that the oil or hydrocarbon saturation of the formation $S_O$ is equal to $S_O=1-S_W$. Obviously, if the formation's pore space is completely filled with water, that is if $S_W=1$, such a formation is of no interest for the purposes of an oil search. On the other hand, if the formation is at $S_{Wirr}$ it will produce all hydrocarbons and no water. Finally, the permeability K of a formation is a measure of the ease with which fluids can flow through the formation, i.e., its producibility.

In recent years nuclear magnetic resonance (NMR) logging has become very important for purposes of formation evaluation and is one of the preferred methods for determining formation parameters. Improvements in the NMR logging tools, as well as advances in data analysis and interpretation allow log analysts to generate detailed reservoir description reports, including clay-bound and capillary-bound related porosity, estimates of the amounts of bound and free fluids, fluid types (i.e., oil, gas and water), permeability and other properties of interest.

The importance of Nuclear magnetic resonance (NMR) logging, at least in part, is due to the fact that unlike nuclear porosity logs, the NMR measurement is environmentally safe and is unaffected by variations in matrix mineralogy. The NMR logging method is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-lattice relaxation time. Another related and frequently used NMR logging parameter is the so called spin-spin relaxation time constant $T_2$ (also known as transverse relaxation time) which is an expression of the relaxation due to non-homogeneities in the local magnetic field over the sensing volume of the logging tool.

NMR tools used in practical applications include, for example, the centralized MRIL® tool made by NUMAR Corporation, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994. Certain details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200; 5,696,448 and 5,936,405. The structure and operation of the Schlumberger CMR tool is described, for example, in U.S. Pat. Nos. 4,939,648; 5,055,787 and 5,055,788 and further in "Novel NMR Apparatus for Investigating an External Sample," by Kleinberg, Sezginer and Griffin, J. Magn. Reson. 97, 466–485, 1992; and "An Improved NMR Tool Design for Faster Logging," D. McKeon et al., SPWLA 40th Annual Logging Symposium, May–June 1999. The content of the above patents is hereby expressly incorporated by reference for all purposes, and all non-patent references are incorporated by reference for background.

Of the above mentioned patents, U.S. Pat. No. 5,280,243 to Miller discloses an NMR apparatus and method of use for geophysical examination of a bore-hole as it is being drilled. In operation, the apparatus connected to the drill bit generates a gradient static magnetic field in a region of the bore hole adjacent the apparatus. This static field extends radially with respect to the longitudinal axis of the apparatus and has a, generally, uniform amplitude along the azimuth with respect to that axis. Typically, a pulsed radio frequency magnetic field excites nuclei in a substantially cylindrical shell around the tool that defines in the formation a sensitive region extending along the length of the tool and having thickness of about 1 mm. Due to this relatively narrow sensitive region, standard wireline NMR relaxation time measurements are difficult to perform with this tool because lateral vibrations during the measurement time would reduce the accuracy of the measurement.

Another U.S. Pat. No. 5,557,201 to Kleinberg et al. discloses a pulsed NMR device in which the accuracy of the measurement with respect to lateral tool vibrations is enhanced by providing a larger sensitive region. This is achieved by a special tool architecture using two tubular permanent magnets with same poles facing each other, and an antenna positioned in the recess between the two magnets. In operation, this tool architecture provides a sensitive region in the formation, which is larger laterally, but greatly reduced along the borehole axis with vertical tool motions adversely affecting the accuracy of the tool measurements.

Another U.S. Pat. No. 6,051,973, assigned to the assignee of this application, which is incorporated herein in its entirety for all purposes, discloses a method and system for measuring a saturation-recovery sequence to reduce errors due to the motion of the logging tool. Motion-independence is achieved, for instance, by issuing a broad-band saturation pulse that covers a large volume within the sample, followed by a narrow-band read-out sequence such that the narrow-band is within the broad-band.

The MRIL® tool is capable of performing a variety of borehole NMR logging measurements the accuracy of which can be improved using the method of the present invention. See, for example, the U.S. Pat. No. 6,242,912 B1, which is a file wrapper continuation of U.S. application Ser. No. 08/542,340, now abandoned, assigned to the assignee of the present application, which teaches systems and methods for lithology independent gas detection. U.S. Pat. No. 6,005,389 assigned to the assignee of the present application and which was filed Mar. 13, 1997 claiming priority of provisional application Ser. No. 60/013,484, teaches, among other things, the use of a rapid-fire CPMG pulse sequence to detect and quantify components having very short relaxation times, such as clay-bound water. The entire content of these patents is hereby expressly incorporated by reference. These and other NMR measurement methods using the MRIL® tool, as well as measurement methods using the Schlumberger CMR tool, can be improved when performed in conjunction with the method of the present invention.

NMR tools of the type discussed above generally measure the time for hydrogen nuclei present in the earth formation to realign their spin axes, and consequently their bulk magnetization, either with an externally applied magnetic field, or perpendicularly to the magnetic field, after momentary reorientation due to the application of specific radio frequency (RF) pulses. The externally applied magnetic field is typically provided by a magnet disposed in the tool. The spin axes of the hydrogen nuclei in the earth formation are, in the aggregate, caused to be aligned with the magnetic field induced in the earth formation by the magnet. The NMR tool includes an antenna positioned near the magnet and shaped so that a pulse of radio frequency (RF) power conducted through the antenna induces a magnetic field in the earth formation orthogonal to the field induced by the magnet. The RF pulse has a duration predetermined so that the spin axes of the hydrogen nuclei generally align themselves perpendicular both to the orthogonal magnetic field induced by the RF pulse and to the externally applied magnetic field. After the pulse ends, the nuclear magnetic moment of the hydrogen nuclei gradually relax, i.e., return to their alignment with the externally applied magnetic field; at the same time an antenna, which is typically the same as the one used by the initial pulse, is electrically connected to a receiver, which detects and measures voltages induced in the antenna by precessional rotation of the spin axes of the hydrogen nuclei.

An actual NMR measurement involves a plurality of pulses grouped into pulse sequences, most frequently of the type known in the art as Carr-Purcell-Meiboom-Gill (CMPG) pulsed spin echo sequences. As known in the art, each CPMG sequence consists of a 90-degree (i.e., $\pi/2$) pulse followed by a large number of 180-degree (i.e., $\pi$) pulses. The 90-degree pulse rotates the proton spins into the transverse plane and the 180-degree pulses generate a sequence of spin echoes by refocusing the transverse magnetization after each spin echo.

It should be apparent that it is important for the NMR measurements to register only signals that are generated by the formation of interest. However, non-formation signals—often referred to as "offset" or "ringing" signals—arise for a variety of reasons. For example, they may be caused by the high-sensitivity tool electronics (e.g., "offsets"), or may be due to magnetostrictive effects (e.g., "ringing") that arise from interactions between pulsed magnetic fields and electronic or magnetic components in the tool. For example, when RF pulses are applied to the antenna, the magnet or antenna can become physically deformed by magnetostriction. After each RF pulse is turned off, the magnet tends to return to its original shape in a series of damped mechanical oscillations, known as "ringing." Ringing induces voltages in the antenna, which can interfere with measurement of the voltages induced by the spin echoes.

A method known in the art for reducing the effect of offsets, ringing and possibly other non-formation signals is to make spin echo measurements in predetermined cycles. Typically, two pulse sequences of opposite phase are acquired to cancel electronic offsets and 180-degree ringing. The pair of pulse sequences is called a phase-alternated pair (PAP). PAP measurements are performed by making a second set of spin echo measurements starting with an original transverse alignment (90 degree) RF pulse, which is inverted in phase from the 90 degree pulse used to start the first set of spin echo measurements. Voltages induced in the antenna during the second set of spin-echo measurements are inverted in polarity from the voltages induced in the first set of measurements. The signals from the second set of measurements can then be subtracted from the signals in the first set of measurements to substantially remove coherent noise, such as the ringing-induced signals. (For simplicity, in the following discussion "ringing" will be used as a catch-all term designating undesirable non-formation signals). Accordingly, in the "PAP method" successive echo-train signals are acquired from the formation that are alternately in-phase and anti-phase with respect to signals that are generated outside the formation; thus, a typical PAP simply comprises any adjacent pair of in-phase and anti-phase CPMG echo-trains. An implicit assumption in this operation is that the tool-related, non-formation signals in an echo-train can somehow be characterized, and that they change little, or even not at all, between successive echo-trains.

Mathematically, the PAP method can be illustrated as follows. Suppose that an individual spin echo train ($CPMG_0$) can be characterized as a summation of a decaying NMR signal from the formation ($S_0$), a non-formation signal ($O_0$), and random or thermal noise ($n_0$), so that $CPMG_0 = S_0 + O_0 + n_0$. The subsequent phase-alternated echo-train ($CPMG_1$), is then given by $CPMG_1 = -S_1 + O_1 + n_1$. Since changes in the non-formation signal are assumed to be minimal, the difference between the two echo-trains (PAP) cancels the non-formation signals, leaving an echo-train that is a composite of the signals and the noise, i.e.:

$$PAP = (S_0 + S_1) + n\Delta$$

Accordingly, in the prior art non-formation noise is removed using the above PAP process, in which one or more phase alternate pair signals are subtracted to remove the ringing. The two acquisition sequences in each phase alternate pairs must be separated in time by $T_W$, the time to repolarize the media. During logging, the tool is moving at a speed v, so that the PAPs are separated by a distance equal to $v^*T_W$. Clearly, this limits the vertical resolution achievable with the tool.

It is thus apparent that to minimize or ideally eliminate non-formation components of the input signal, in accordance with the prior art it is the PAP, rather than the individual echo-train that becomes the basic measured element, which is then processed in similar manner to NMR echo-trains acquired in a laboratory. A potential advantage of the prior art method is that it results in increased SNR of the output signal due to the averaging operation. As discussed above, however, using PAPs as opposed to single echo trains as basic measurement units also introduces a delay that places various constraints on both the achievable logging speed and the vertical resolution of NMR logs.

As noted, prior art methods use a single operation to accomplish both the ringing elimination, as well as the signal-to-noise improvement by means of experiment stacking. One requirement of the prior art methods is to select an amount of stacking necessary for a desired SNR that includes, with equal weight, every PAP at every acquired frequency. This is typically referred to as "boxcar" filtering of the data. For an NMR tool operating at a single frequency, the number of PAPs stacked is simply one or more. For NMR logging tools, such as the MRIL® Prime, operating at N frequencies, the numbers of PAPs stacked must be a multiple of N. Since each PAP comprises two echo-trains, the minimum stacking for the MRIL® tool is two times the number of acquired frequencies. There are two problems associated with this approach. First, in formations with high signal-levels, the approach results in more stacking than is necessary to provide adequate signal-to-noise ratio. On the other hand, for those formations with lower signal-levels, in which more stacking is required to obtain adequate SNR, it is necessary to select an amount of stacking, which is a multiple of the minimum stacking. This is undesirable at least because the extra averaging introduces undesirable processing delays and, as shown below, reduces the maximum vertical resolution.

As shown in the detailed disclosure, in accordance with the present invention an alternative approach can be used where the ringing and random noise components are processed in two steps with possibly different filters. The results show that the (vertical) resolution of NMR logs can be improved in many cases. The output of the proposed processing method is consistently less noisy and more robust even in those cases where there is not a significant vertical resolution improvement compared to the conventional boxcar filter approach.

Focusing next on another deficiency associated with the prior art, as a consequence of the PAP method, the "best-possible" effective vertical resolution of an NMR log acquired with a moving tool is a combination of both the inherent vertical resolution of the tool antenna—the antenna aperture—and the distance traveled between the pair of echo-train measurements that comprise a PAP. As discussed above, however, in many logging situations the vertical resolution is further compromised by the need to average data from multiple PAPs to ensure an adequate signal-to-noise ratio (SNR) for confident data analysis. For example, it is known in the art to improve the SNR of NMR well logging measurements by averaging a plurality of PAPs, typically eight or more.

Depending on the specific "PAP accounting method" employed, echo-trains can form PAPs in a number of different ways. For example, in one method, two adjacent echo-trains form a single PAP, three adjacent echo-trains form two PAPs, and four echo-trains form three PAPs. In an alternative method, while two adjacent echo-trains still form a single PAP, four adjacent echo-trains might be needed to form two PAPs, with six adjacent echo-trains needed to form three. See FIG. 11A. Illustrated in the figure is the "overlapping" mode of operation (of the CMR tool discussed above), where one PAP is acquired every sample interval. As illustrated, in an overlapping mode the two CPMGs overlap half of the sample interval, and the tool relies on the wait time to polarize the hydrogen spins for the NMR measurement. The logging speed (v) of the tool depends on a number of factors, primarily the sample interval and the measurement wait time.

As shown in FIG. 11B in a different embodiment of the CMR tool (CMR Plus), to speed up the measurements the tool uses a new measurement sequence called a sequential PAP. As illustrated, the tool acquires a single CPMG per sample interval, and the phase of each successive CPMG is shifted 180 degrees. A PAP is formed every sample interval by combining the most recent CPMG with the prior CPMG. This measurement sequence allows the tool to move faster, however, it is apparent that the number of independent CPMGs is reduced, which increases the noise level.

In earlier models of the MRIL® tool, the typical logging speed used to acquire NMR data is sufficiently low, so that the effective vertical resolution of the NMR log is dominated by the need to stack multiple PAPs to obtain adequate SNR. For the multi-frequency MRIL® Prime tool, however, the use of multiple NMR measurement frequencies is conceptually equivalent to the simultaneous acquisition of multiple passes with the earlier logging tools. Thus, MRIL® Prime logs could be acquired at faster logging speeds, with the required SNR obtained by stacking multiple PAPs across the frequency bands.

Unfortunately, in high-signal formations (e.g., high porosity, oil-or water-filled rocks), where the logging speeds can be comparatively fast, the effective vertical resolution of the NMR log becomes dominated by the tool movement during a single PAP. For example, with a recovery time of 10 seconds between echo-trains in a PAP, with PAPs acquired at all possible frequencies, the elapsed time between the first echo-train in the first-frequency PAP and the second echo-train for the last-frequency PAP, is close to 20 seconds. At a logging speed of 900 ft/hr (15 ft/min), the MRIL® tool will move approximately 5 feet during this measurement: when combined with the inherent vertical resolution of the antenna (which is approximately 2 feet), the effective vertical resolution becomes roughly 7 feet.

Enhancing the resolution of the logs is a significant problem, because subsurface formations are generally heterogeneous, so that porosity, saturation and lithology vary with position. A common example of heterogeneity is the presence in the formation of geological layers, or beds. Because logging tools have a nonzero volume of investigation, more than one layer may lie within the volume of investigation of a tool. In such cases, the petrophysical evaluation of one layer may be distorted by the presence of another layer falling within the larger volume of investigation of the tool. The above phenomenon leads to a specific problem in the analysis of subsurface formations that include one or more underground layers, especially when the layers are thin compared with the vertical resolution of the measuring tool. Such layers have become subject to significant commercial interest because of their production potential. Any knowledge about the composition and properties of such layered formations that helps better estimate their production potential has thus become increasingly valuable.

Clearly, to make the best use of the NMR logging tools, it is necessary that the current reliance on the PAP as the basic measured element be reduced. Clearly, if for example the MRIL® Prime data can be acquired and/or processed in such a manner that a single echo-train, rather than a PAP, becomes the basic unit of measurement, then it becomes possible to provide an NMR log with an effective vertical resolution much closer to the inherent resolution defined by the length of the tool antenna. Using the assumptions in the example above, if it was only necessary to stack echo-trains from four frequencies to obtain adequate SNR, the elapsed time of the measurements would be about 5 seconds, during which time the MRIL® tool would move approximately 1 foot, resulting in the effective vertical resolution of the NMR log of approximately 3 feet. It is clear therefore that any mechanism that for a given SNR supported by the formation can increase the vertical resolution of the tool without decreasing the logging speed is highly desirable.

Turning to the measured signal from the error and speed related concerns, an important measurement parameter used in NMR well logging is the formation diffusion D. Generally, diffusion refers to the motion of atoms in a gaseous or liquid state due to their thermal energy. The diffusion parameter D is dependent on the pore sizes of the formation and offers much promise as a separate permeability indicator. In a uniform magnetic field, diffusion has little effect on the decay rate of the measured NMR echoes. In a gradient magnetic field, however, diffusion causes atoms to move from their original positions to new ones, which moves also cause these atoms to acquire a different phase shifts compared to atoms that did not move, and will thus contribute to a faster rate of relaxation. Therefore, in a gradient magnetic field diffusion is a logging parameter, which can provide independent information about the structure of the geologic formation of interest, the properties of the fluids in it, and their interaction.

It has been observed that the mechanisms, which determine the values of $T_1$, $T_2$ and D depend on the molecular dynamics of the sample being tested. In bulk volume liquids, typically found in large pores of the formation, molecular dynamics is a function of molecular size and inter-molecular interactions, which are different for each fluid. Thus, water, gas and different types of oil each have different $T_1$, $T_2$ and D values. On the other hand, molecular dynamics in a heterogeneous media, such as a porous solid which contains liquid in its pores, differs significantly from the dynamics of the bulk liquid and generally depends on the mechanism of interaction between the liquid and the pores of the solid media. It will thus be appreciated that a correct interpretation of the measurement parameters $T_1$, $T_2$ and D can provide valuable information relating to the types of fluids involved, the structure of the formation and other well logging parameters of interest.

A major barrier to using NMR logging alone for determination of porosity and other parameters of interest in the past has been the widespread belief that a near-wellbore NMR measurement cannot detect hydrocarbon gases. Failure to recognize such gases may result in their contribution being misinterpreted as bound fluid, which mistake may in turn result in excessively high irreducible water saturations and correspondingly incorrect permeability estimates. It has recently been found, however, that the NMR properties of gas are in fact quite different from those of water and oil under typical reservoir conditions and thus can be used to quantify the gas phase in a reservoir. More specifically, the Magnetic Resonance Imaging Log (MRIL®) tools of NUMAR Corporation have registered the gas effect as distortion in the bound volume irreducible (BVI) and/or free fluid index (FFI) measurements.

In the paper, entitles "NMR Logging of Natural Gas Reservoirs," paper N, presented at the $36^{th}$ Annual SPWLA Symposium, Paris, Jun. 26–29, 1995, Akkurt, R. et al. have shown one approach of using the capabilities provided by NUMAR's MRIL® tool for detection of gas. The content of the Akkurt et al. paper is incorporated herein for all purposes. In this paper, the authors point out that NMR signals from gas protons are detectable, and derive $T_1$ relaxation and diffusion properties of methane-dominated natural gas mixtures at typical reservoir conditions. The magnetic field gradient of the MRIL® is used to separate and to quantify water, oil and gas saturations based solely on NMR data.

The results in the Akkurt paper are based on the NUMAR MRIL-C tool, the output of which is used to obtain $T_2$ spectra. $T_2$ spectra are extracted from the raw CPMG echo trains by breaking the total NMR signal M(t) into N components, called bins, according to the formula:

$$M(t) = \sum_{i=1}^{N} a_i \exp(-t/T_2)$$

where $a_i$ is the porosity associated with the i-th bin. Each bin is characterized by a fixed center transverse relaxation time $T_{2i}$. The total NMR porosity is then determined as the sum of the porosities $a_i$ in all bins. The $T_2$ spectrum model is discussed in detail, for example, in Prammer, M. G., "NMR Pore Size Distributions and Permeability at the Well Site," paper SPE 28368, presented at the 69-th Annual Technical Conference and Exhibition, Society of Petroleum Engineers, New Orleans, Sep. 25–28, 1994, the content of which is expressly incorporated herein for all purposes.

On the basis of the $T_2$ spectra, two specific methods for gas measurements are proposed in the Akkurt paper and will be considered briefly next to provide relevant background information. The first method is entitled "differential spectrum method" (DSM). The DSM is based on the observation that often light oil and natural gas exhibit distinctly separated $T_2$ measurements in the presence of a magnetic field gradient, even though they may have overlapping $T_1$ measurement values. Also, it has been observed that brine and water have distinctly different $T_1$ measurements, even though their $D_0$ values may overlap. The DSM makes use of these observations and is illustrated by a specific example for a sandstone reservoir containing brine, light oil and gas. According to the Akkurt et al. paper, two separate logging passes are made with different wait times $TR_1$, and $TR_s$, such that the longer time $TR_1 \geq T_{1g}$, and the shorter time satisfies the relationship $T_{1g} \geq TR_s \geq 3T_{1wmax}$.

Due to the large $T_1$ contrast between the brine and the hydrocarbons the water signal disappears when the spectra of the two signals are subtracted. Thus, the differential $T_2$ spectrum contains only hydrocarbon signals. It should be noted that the subtraction of the $T_2$ spectra also eliminates all bound water, making the DSM very useful in shaly sands.

The second method proposed in the Akkurt et al. paper is called "shifted spectrum method" (SSM). Conceptually the method is based on the observation that since the surface relaxation for gas is negligible, the apparent $T_2$ relaxation can be expressed as:

$$\frac{1}{T_2} = \frac{1}{T_{2b}}\left[1 + \frac{(\gamma G\tau)^2 D T_{2B}}{2}\right]$$

where G is the magnetic field gradient, D is the diffusion coefficient, $\tau$ is half the interecho time, $\gamma$ is the gyromagnetic ratio and $T_{2B}$ refers to the bulk relaxation. It is known in the art that for gas, which is a non-wetting phase, $T_1 = T_{1B} \approx T_{2B}$. Therefore, given that the product $D_0, T_1$ of a gas after substitution in the expression above is an order of magnitude larger than oil and two orders of magnitude larger than brine, it can be seen that the already large $DT_1$ contrast of gas can be enhanced even further by increasing the interecho time $2\tau$ in order to allow the separation of two fluids that overlap in $T_1$. The SSM is based on the above concept and may result in the signal from gas being shifted out of the detectability range, so that the single spectrum peak is due to brine.

While the DSM and the SSM methods discussed in the Akkurt et al. paper and briefly summarized above provide a possible working approach to detection of gas using solely NMR data, the methods also have serious disadvantages which diminish their utility in practical applications. Specifically, due to the fact that two separate logging passes are required, the Akkurt methods show relatively poor depth matching properties on repeat runs. Furthermore, subtraction of signals from different logging passes is done in the $T_2$ spectrum domain which may result in losing valuable information in the transformation process, especially when the received signals have low signal-to-noise ratios (SNRs). In fact, for a typical logging pass, low hydrocarbon index (HI) of the gases in the formation, and relatively long $T_1$, times generally lead to low SNR of the received signals. After transformation into the $T_2$ spectrum domain even more information can be lost, thus reducing the accuracy of the desired parameter estimates. Finally, the Akkurt et al. paper does not indicate ways of solving additional problems such as accounting for low gas saturation in the sensitive volume, the presence of gases other than methane, and the temperature dependency of the filed gradient.

While techniques have been developed in the prior art to extract information about the structure and the fluid composition of a geologic formation, so far no consistent NMR well logging method has been proposed to accurately and efficiently interpret these measurement parameters by accounting for the different effects of individual fluids and various sources of error. This often leads to inaccurate or misleading log data interpretation, which, in turn, can cause costly errors in the oil exploration practice. Therefore, there is a need for a NMR system and method for providing consistent and accurate evaluation of geologic formations using a combination of substantially simultaneous log measurements to take into account the effects of different fluids. Since in the presence of very high ringing amplitudes (100%–200% of full scale NMR signals), the residuals from phase- and frequency-alternation are still strong enough to affect the final result (a 200% ringing signal, cancelled with 98% efficiency, can result in about +/−4 p.u. (porosity unit) error in the final result) it is desirable to measure both the efficiency of the ringing cancellation and the amplitude and phase (i.e sign) of the ringing residual with respect to the NMR signal. This can serve as a quality control indicator as well as leading to additional corrective measures or avoidance of unnecessary corrective measures.

SUMMARY OF THE INVENTION

Accordingly, it is an object of the present invention to overcome deficiencies associated with the prior art and in particular to provide a method and system for improving the resolution of borehole NMR logging measurements, suppressing artifacts in NMR data obtained from logging measurements, and providing an estimate of residual artifacts to enable additional noise and artifact reduction if required.

These and other objects are accomplished in accordance with a preferred embodiment of the present invention by a novel approach in which non-formation, i.e., ringing, signals are characterized and removed from the underlying NMR spin echo signals. In particular, to analyze the ringing signals it is first proposed to combine several acquisition sequences such that the ringing components are substantially removed. Moreover, the combined acquisition sequences also provide an estimate of the residual ringing signal remaining. This residual ringing signal may be used to decide whether additional processing steps are desirable to further improve the SNR.

A method of the present invention for nuclear magnetic resonance (NMR) measurement of a geologic formation comprises providing, in a geologic formation, at least one first plurality of phase alternated NMR pulses at a first frequency ($F_1$), and receiving at least one corresponding first signal in response thereto. The method includes providing, not necessarily simultaneously, at least one second plurality of phase alternated NMR pulses at a second frequency ($F_2$), and receiving at least one corresponding second signal in response thereto. In an embodiment of the invention, a difference between the first and second frequencies is a function of one or more of an inter echo spacing, a time delay between an excitation pulse and a data acquisition window, and a rate for generating echoes. The received the first and second signals are combined to obtain a corrected NMR signal.

Suitable choices of dephasing delays between plurality of NMR pulses allow for measuring different phases in the formation and improving signal to noise ratio of NMR signals. A method of the present invention comprises: providing, separated by a first dephasing delay, a first and second plurality of phase alternated NMR pulses at a frequency $F_1$ and receiving a first and second corresponding signals in response thereto. Similarly, providing, separated by a second dephasing delay, a third and fourth plurality of phase alternated NMR pulses at a frequency $F_2$ and receiving a third and fourth corresponding signals in response thereto. A residual non-formation signal contribution is estimated by combining the second and the fourth received signals. Preferably, a de-phasing delay is about $(N+1/2)\tau$, where $\tau$ is proportional to the time between two echoes and N is an integer, which is less than 6.

In another aspect, the difference between the first and second frequencies is given by $$|F_1 - F_2| = \left(n + \frac{1}{2}\right)\frac{1}{2\tau},$$

wherein n is an integer, and $\tau$ is an inter echo spacing. Preferably, n is zero. In alternative embodiments n is sufficiently large, e.g., 2, resulting the first frequency $F_1$ and the second frequency $F_2$ corresponding to non-overlapping resonant volumes in the geologic formation.

In another aspect, in an embodiment of the invention, echoes from corresponding interleaved pulses at the first frequency $F_1$ and second frequency $F_2$ are combined to form a composite signal. The echoes in the composite signal are processed to generate a difference signal between a first echo at the first frequency $F_1$, corresponding to a first recovery time, and a second echo corresponding the second frequency $F_2$, to a second recovery time. The recovery times may be selected to reduce or substantially eliminate signals associated with one or more of a gas phase, water phase, and oil phase in the geological formation by dephasing.

In another aspect, additional frequencies may be employed such as for providing a fifth plurality of NMR pulses corresponding to a third frequency $F_3$, wherein the first frequency $F_1$ and third frequency $F_3$ correspond to non-overlapping resonant volumes in the geologic formation and pulses at the first frequency $F_1$ maybe interleaved with pulses at the third frequency $F_3$. For estimating the effects of diffusion and/or selecting phases sensitive thereto echoes from corresponding interleaved pulses at the first frequency $F_1$ and third frequency $F_3$ are combined to form a composite signal, which is processed to generate a difference signal between a first echo, corresponding to a first recovery time, and a second echo corresponding to a second recovery time.

Preferably, the first and second echo in the composite signal form a pair of echoes substantially corresponding to a single depth mark and the composite signal comprises a plurality of pairs of echoes.

In an aspect of the invention, there is provided a method for determining petrophysical properties of a volume of earth formation in a borehole using an NMR tool. The method comprises the steps of: providing a static magnetic field in said volume of earth; providing oscillating magnetic fields in said volume of earth formation, to detect echoes thereto as an induced signal, according to pulse sequence comprising a first set of CPMG pulses associated with a pulse echo spacing $\tau_1$ and a second set of CPMG pulses associated with a pulse echo spacing $\tau_2$, shorter than $\tau_1$; and processing the induced signal with additional induced signals to determine petrophysical properties of the volume of earth formation.

In an aspect, the additional induced signals correspond to at least one saturation recovery time different than a saturation recovery time of the pulse sequence. Furthermore, data comprising the induced signal and the additional induced signals may be acquired in at least two orthogonal channels.

In an aspect of the invention, there is provided a method for making nuclear magnetic resonance (NMR) measurements of a geologic formation using an NMR logging tool, comprising the steps of: providing a static magnetic field in the a volume of the formation; applying oscillating magnetic fields according to at least one modified CPMG pulse sequence characterized by at least one first echo spacing TD and a second echo spacing TE; wherein the at least one first echo spacing TD is selected to correspond to diffusion characteristics of fluids in the formation and cause corresponding amplitude loss in induced NMR echo signals, and TE is relatively short, such that diffusion in the corresponding induced NMR echo signals is substantially negligible; measuring the induced NMR echo signals; determining the amount of amplitude loss resulting from at least one TD interval; and computing diffusion properties of fluids in the formation based on the determined amplitude loss. Preferably, the modified CPMG sequence is repeated with an echo spacing TD≧TE. Preferably, TD is selected to cause loss of signals associated with the gas phase and the water phase to derive petrophysical properties of the geological formation, and/or estimate diffusivity values for gas, water and oil phases in the formation, and/or select values for the TD and TE echo spacings based on the estimated diffusivity values.

Advantageously, the selection of values for the TD and TE echo spacings may be based on forward-modeling of signal components to achieve maximum contrast between fluid phases. In another aspect, the invention also includes a modified CPMG sequence suitable for generating two or more orthogonal channels that are combined to edit out, in NMR data collected using an NMR logging tool, information primarily relating to diffusion, gas, water, brine, or oil, the modified CPMG sequence having at least two different echo-to-echo spacings.

In another aspect, the invention also includes a system for increasing the resolution of NMR log data obtained using a multi-frequency NMR tool having N operating frequencies, comprising: means for providing a NMR pulse echo signal comprising components corresponding to at least two operating frequencies of the tool; means for separating the provided pulse echo signal into two or more data-flow paths, each data flow path corresponding to an operating frequency of the tool; means for processing the signal in each data flow path separately to remove coherent noise components; means for combining output signals from the separately processed data flow paths to remove random noise components; and means for estimating residual coherent noise. Preferably, the system further comprises means responsive to the residual coherent noise for initiating additional noise reduction by stacking at least one more signal.

BRIEF DESCRIPTION OF THE DRAWINGS

FIG. 5 illustrates the effects of different levels of experiment stacking as applied in the Experiment Stacking step in accordance with the present invention;

FIGS. 22, 23 and 24 illustrate in more detail the method of the present invention replacing standard box-car processing with a two-stage filtering.

FIG. 25 illustrates an example cycle of pulse sequences in accordance with a preferred embodiment of the present invention for combining frequency dithering with phase alternation.

DETAILED DESCRIPTION OF THE PREFERRED EMBODIMENTS

During the course of the description like numbers will be used to identify like elements shown in the figures. Bold face letters represent vectors, while vector elements and scalar coefficients are shown in standard print.

I. The System

Figure 1:
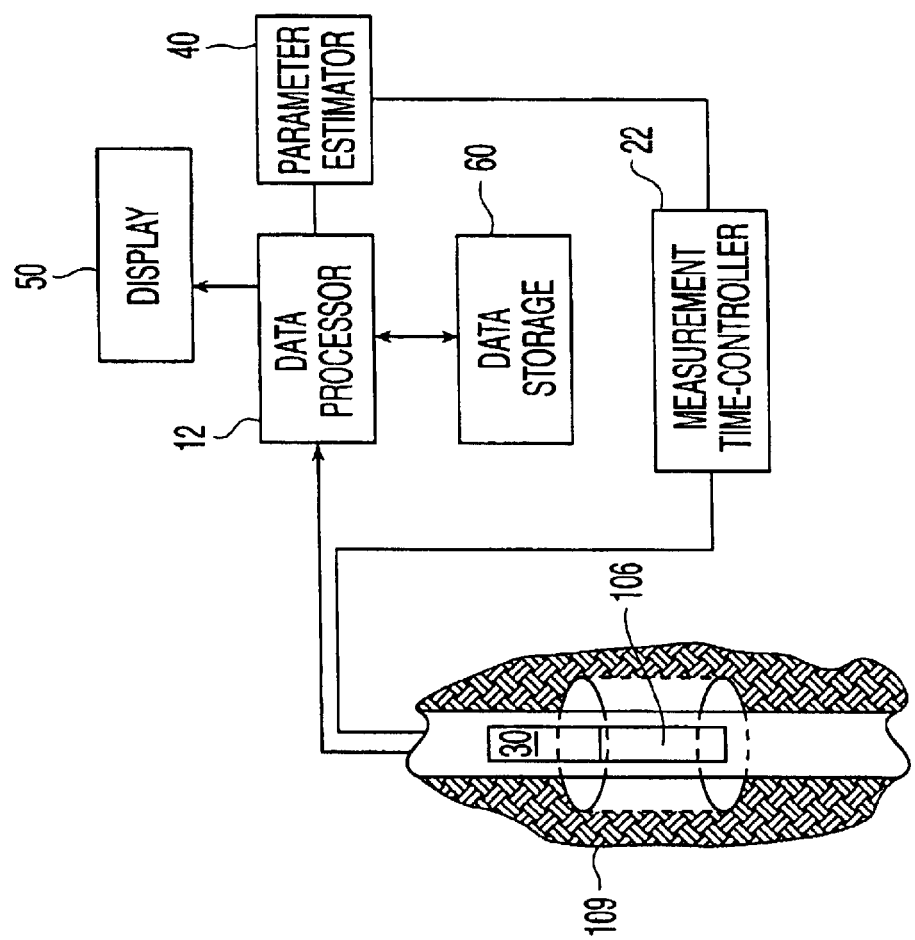
FIG. 1 is a block diagram of a NMR logging system used in accordance with the present invention.

FIG. 1 is a block diagram of a system in accordance with a specific embodiment of the present invention, which shows individual block components for controlling data collection, processing of the collected data and displaying the measurement results. In FIG. 1 a logging tool 106 comprises an NMR probe controller 30 and pulse echo detection electronics and is lowered in a borehole drilled in the formation 109. The output signal from the tool detection electronics is processed by data processor 12 to record NMR pulse echo data from the tool and analyze the relaxation characteristics of the materials surrounding the borehole. The output of the data processor 12 is fed to parameter estimator 40. Measurement cycle controller 22 provides an appropriate control signals to the probe. The processed data from the log measurements is stored in data storage 60. Data processor 12 is connected to display 50, which is capable of providing a graphical display of one or more measurement parameters, preferably superimposed on display data from data storage 60. The components of the system of the present invention shown in FIG. 1 can be implemented in hardware or software, or any combination thereof suitable for practical purposes.

In order to separate signal contributions from different fluids, an NMR tool must be able to operate in a three-dimensional parameter space: $T_2$ (transverse decay time), measured by a CPMG pulse-echo sequence: $T_1$ (longitudinal polarization time), measured by variable saturation-recovery times; and D (apparent, restricted diffusivity), measured by varying the CPMG pulse-echo spacing T in the presence of a magnetic field gradient.

In a preferred embodiment of the present invention measurements in a moving logging tool are enabled using, in relatively general form, apparatus for carrying out NMR borehole diffusion coefficient determinations. The apparatus includes a first portion, which is arranged to be lowered into a borehole in order to examine the nature of materials in the vicinity of the borehole.

The first portion comprises a magnet or a plurality of magnets, which generate a substantially uniform static magnetic field in a volume of investigation. The first portion also comprises an RF antenna coil which produces an RF magnetic field at the volume of investigation which field is substantially perpendicular to the static magnetic field.

In addition to the static magnetic field gradient generated by magnet(s), an optional magnetic field gradient coil, or plurality of coils, can also be used to generate a magnetic field gradient at the volume of investigation. This additional contribution to the magnetic field has a field direction preferably collinear with the substantially uniform field and has a substantially uniform magnetic field gradient, which may or may not be switched on and off by switching the dc current flowing through the coil or coils. The magnet or magnets, antenna and the gradient coil constituting portion are also referred to as a probe.

The antenna together with a transmitter/receiver (T/R) matching circuit typically include a resonance capacitor, a T/R switch and both to-transmitter and to-receiver matching circuitry and are coupled to an RF power amplifier and a receiver preamplifier. A power supply provides the dc current required for the magnetic field gradient generating coils. All the elements described above are normally contained in a housing, which is passed through the borehole. Alternatively, some of the above elements may be located above ground.

The control circuitry for the logging apparatus may include a computer, which provides a control output to a pulse programmer, which receives an RF input from a variable frequency RF source. The Pulse programmer controls the operation of the variable frequency RF source as well as an RF driver, which receives an input from the variable frequency RF source and outputs to an RF power amplifier.

The complex time-domain signal from the RF receiver preamplifier is supplied to an RF receiver, which optionally receives input from a phase shifter. Phase correction may be performed using signal processing algorithms. Pulse programmer controls the gradient coil power supply enabling and disabling the flow of current, and hence controls the generation of static or pulsed field gradients, according to the commands of the computer. Some or all of the elements described above may be disposed in an above-ground housing and/or below ground. Improved devices and measurement methods, which can be used with or as the probe are described generally in U.S. Pat. Nos. 4,710,713; 4,717,876; 4,717,877; 4,717,878, 5,212,447; 5,280,243; 5,309,098 and 5,412,320 all of which are commonly owned by the assignee of the present invention. A specific embodiment of the tool which can be used in accordance with the present invention is also discussed in detail in Chandler et al., "Improved Log Quality with a Dual-Frequency Pulsed NMR Tool," paper SPE 28365, presented at the 69-th Annual Technical Conference and Exhibition, Society of Petroleum Engineers, New Orleans, Sep. 25–28, 1994. The contents of these patents and the Chandler et al. paper are hereby expressly incorporated for all purposes.

Figure 2:
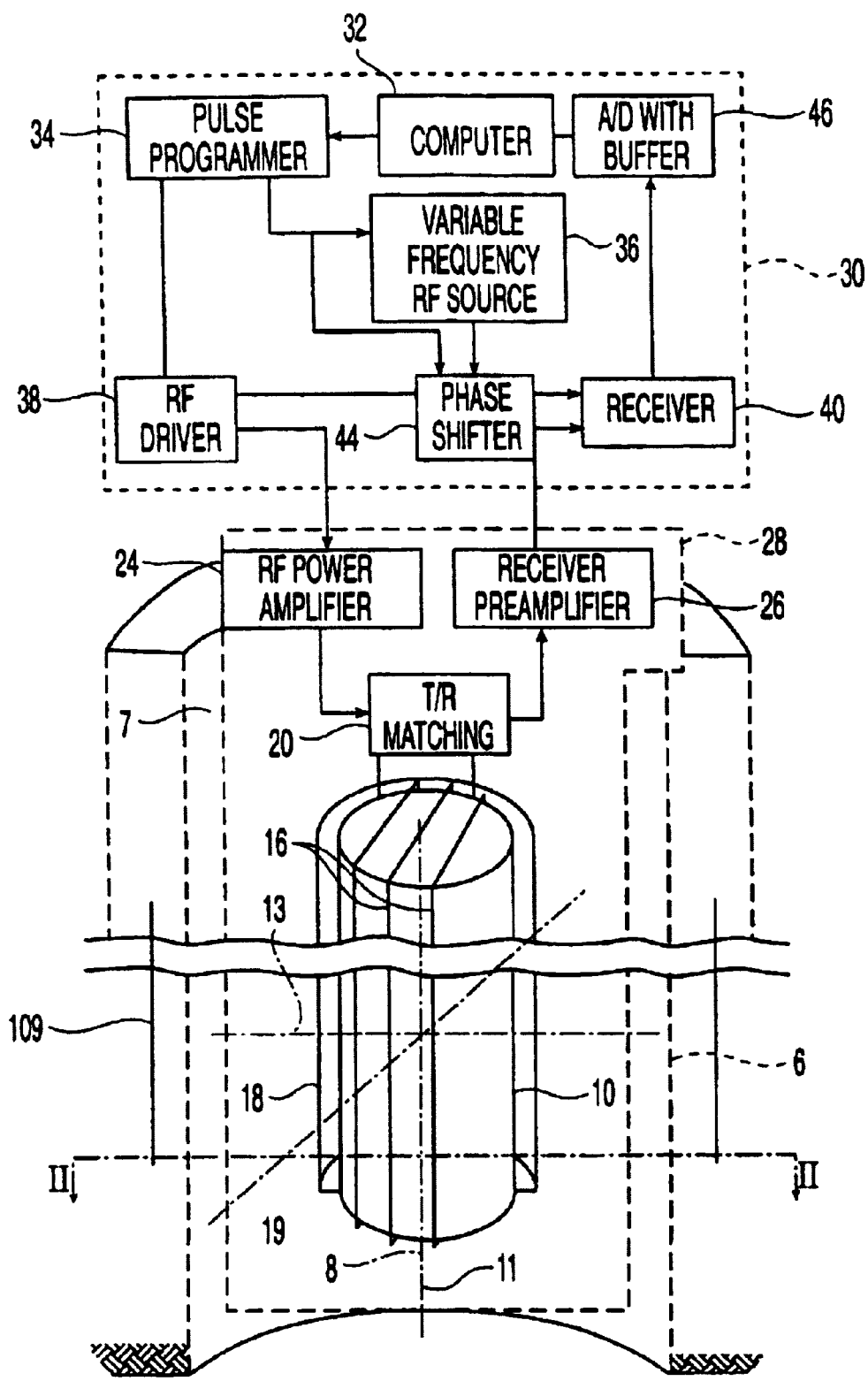
FIG. 2 is a partially schematic, partially block diagram of a NMR logging tool and attached electronics used in a preferred embodiment.

Reference is now made to FIG. 2, which illustrates in a semi-block diagram form an NMR logging apparatus, such as the MRIL® Prime tool of Numar Corporation (a Halliburton Company), which can be used for NMR measurements in accordance with the present invention. In standard operation, first portion 6 of the tool is arranged for lowering into a borehole 7 having a borehole longitudinal axis 8 in order to examine properties of the geologic formation in the vicinity of borehole 7.

The first portion comprises a generally cylindrical permanent magnet 10, preferably having a longitudinal axis 11, which is preferably coaxial with the longitudinal axis 8 of the borehole. Alternatively, a plurality of permanent magnets 10 may be employed. Permanent magnet 10 preferably has uniform magnetization substantially perpendicular to the longitudinal axis of the logging tool, which is parallel to the longitudinal axis 8 of the borehole 7.

The first portion 6 also comprises one or more coil windings 16, which preferably are arranged on top of the permanent magnet and form the tool antenna. The magnetization direction 13 created by the antenna is substantially perpendicular to the longitudinal axis 11 of the bore hole. The coil windings 16, together with a transmitter/receiver (T/R) matching circuit 20 define a transmitter/receiver (T/R) circuit. T/R matching circuit 20 typically includes a resonance capacitor, a T/R switch and both to-transmitter and to-receiver matching circuitry and is coupled to a first RF power amplifier 24 and to a receiver pre-amplifier 26.

The permanent magnet 10 and coil windings 16 are preferably housed in a non-conductive, non-ferromagnetic protective housing 18. The housing and its contents will hereinafter be referred to as the probe 19.

In operation, the probe along with RF amplifier 24, preamplifier 26 and T/R matching circuit 20, designated collectively as housing 28 are passed through the borehole. Alternatively, some of the above elements may be located above ground in housing 30.

Disposed in a housing indicated in FIG. 2 by block 30, is a control circuitry, including a computer 32, which provides a control output to a pulse programmer 34. Pulse programmer 34 controls the operation of phase shifter 44, as well as an RF driver 38, which drives RF power amplifier 24. Pulse programmer 34 controls the operation of a variable frequency RF source 36, the output of which is passed through phase shifter 44 to the RF driver 38. The signal from RF driver 38 is amplified in RF power amplifier 24 and passed through T/R matching circuit 20 to the antenna 16.

NMR signals from excited nuclei in the formation surrounding the borehole are picked up by the receiving antenna 16 and passed through T/R matching circuit 20 to RF receiver pre-amplifier 26, the output of which is supplied to an RF receiver 40 which also receives an input from phase shifter 44. Receiver 40 outputs via an A/D converter with a buffer 46 to the computer 32 for providing desired well logging output data for further use and analysis.

As indicated above, the MRIL tool used in a preferred embodiment of the present invention is digitally based, so that raw echo data is digitized at the carrier frequency and all subsequent filtering and detection is performed in the digital domain. For the purposes of the present invention, the critical feature of the tool is its ability to operate at different frequencies.

Figure 28:
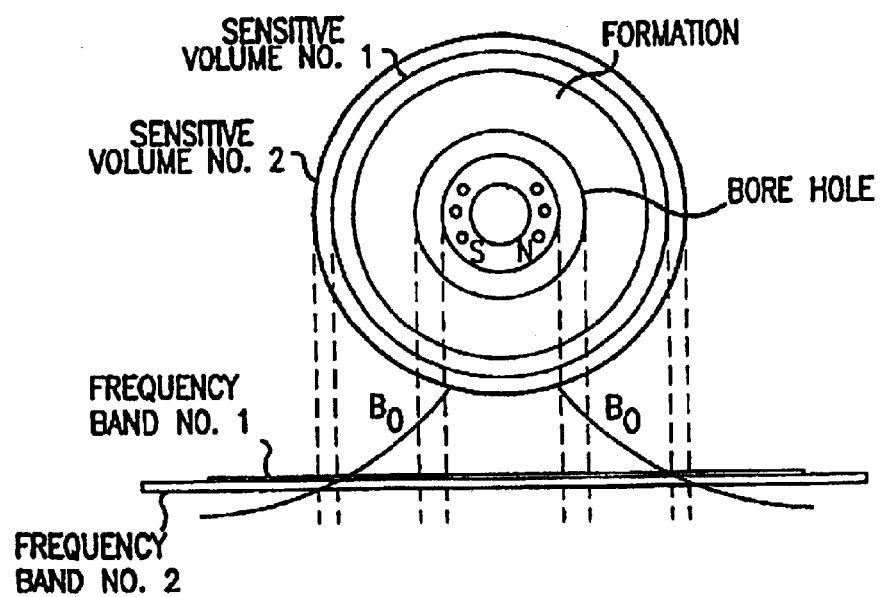
FIG. 28 illustrates the operation of a gradient logging tool in a multi-frequency mode at the example of dual-volume investigation.

The system is typically capable of "hopping" from one operating frequency to another, the effect of which includes shifting the radial position of the resonant volume for the tool. The frequency shift is selected in such manner that at least two non-overlapping resonant volumes are formed; each new resonant volume associated with a different frequency being filled with fully relaxed protons. Hopping between two or more (i.e., K) frequencies thus allows reducing the time between experiments approximately by a factor of K, without compromising complete $T_1$ measurements or adopting imprecise empirical $T_1/T_2$ relationships; the logging speed for the tool can accordingly be increased approximately K times. This feature is illustrated in FIG. 28 in which hopping between two different frequencies is shown to result in conducting measurements in two non-overlapping resonant volumes. In the specific example illustrated in FIG. 28 each frequency band is about 6 kHz wide and the two mean band frequencies are offset by about 15 kHz. This mode of operation forms two concentric annuli, each 0.04 inch (0.1 cm) thick, separated center to center by about 0.09 inches (0.23 cm).

The logging speed of the device used in a preferred embodiment of the present invention depends upon different factors including the SNR of the received signal, the desired log precision and vertical resolution, and the cycle time permitted by the $T_1$ parameter of the formation. Preferably, for greater than 95% recovery within a single resonant volume, the recovery time should satisfy the requirement $T_R \geq 3T_1$. As a consequence of the multi-frequency operation, the cycle time is only slightly longer than the $T_R$ normalized to the number of frequencies employed. (i.e. $T_C \approx T_R/2$ for two operating frequencies).

The MRIL tool used in a preferred embodiment of the present invention generally has a vertical excitation/response function that can be represented by a near-perfect rectangular aperture. In a specific embodiment, a high vertical resolution, 24" (60.96 cm) long aperture, or a lower vertical resolution, 43" (109.22 cm) long, aperture are used. In order to perform $T_1$-weighted signal measurements, as discussed in detail below, it is required that the formation volume being sensed remains substantially unchanged over the course of a recovery period. Specifically, for a moving tool, it has been determined that volume changes of about 10–20% still provide adequate measurement accuracy. It is possible to impose either a minimum aperture length or a maximum tool logging speed requirement which must satisfy the condition for substantial measurement stationarity. For example, in the specific embodiment of a 24" long aperture, assuming recovery time $T_R$=2s, and imposing a 10% accuracy requirement, it can be seen that the maximum allowed tool speed is v=5*2.4"/2 s=6 ft/min (3.05 cm/sec). For the alternate configuration using a 43" long antenna, under the same assumptions the maximum tool speed is about 11 ft/min (5.588 cm/sec).

For instance, for the purposes of making $T_1$ weighted measurements with a moving logging tool at least one long saturation-recovery (SR) interval is required, preferably of about 8–10 sec. It should be noted that for such an interval logging data is substantially insensitive to vertical tool displacement because at the end of the interval the formation magnetization is already close to an equilibrium. The transverse magnetization left after a CPMG sequence is quickly dephased in the strong gradient field. At this point, a saturation-recovery (SR) measurement can be started, as known in the art. The recovered magnetization is read out by the next CPMG train. In addition to the relatively long SR interval, one or more measurements are made using shorter recovery intervals, as described in more detail next.

Random lateral tool motion is a source of concern for the validity of the downhole $T_1$-weighted measurements in accordance with the present invention. The reason is that since the sensitive volume for the tool resembles a cylindrical slice of about 1–2 mm thickness, lateral swaying of the tool could cause an influx of fully polarized magnetization and thus give incorrect measurements. Studies of actual log data repeatedly acquired over the same zones, however, show monotonic recovery behavior of sequences with increasing SR intervals, indicating that lateral tool motion generally has a negligible effect on the actual measurements. Further evidence that side effects due to lateral motion of the tool are often insignificant is provided by the consistency of MPHI and FFI measurements made with the tool, which are both independent of the $T_1$ parameter. In addition, U.S. Pat. No. 6,051,973, assigned to the assignee of this application, issued on Apr. 18, 2000, and incorporated herein by reference in its entirety for all purposes, provides effective techniques for providing protection against errors due to tool motion. In particular, it teaches the use of a broadband saturating pulse followed by narrow pulse-echo sequences in NMR data collection to protect against the influx of fully polarized protons with lateral sway of the tool.

Another source of concern in NMR logging is the relatively shallow depth-of-investigation which, due to the generally cylindrical shape of the resonance volume of the tool, also depends on the borehole size. Thus, in some cases shallow depth-of-investigation along with the fact that invading fluid in the borehole replaces gas can lead to a reduction in the gas effect which can be sensed by the tool. It should be noted, however, that the MRIL tool's sensitive volume has an approximately 4" (10.16 cm) blind zone extending from the borehole wall. The presence of such blind zone effectively limits the influence of fluid invasion. Experimentally, in most cases residual hydrocarbon saturations seen by the tool have been shown to be sufficient for hydrocarbon detection purposes and can be close to uninvaded saturations.

The CPMG pulse sequences used with the MRIL tool in accordance with the present invention have been described generally in U.S. Pat. No. 5,212,447 assigned to the assignee of the present application. Also discussed in this patent are specific methods of conducting NMR measurements, including derivations of the diffusion coefficient D and/or $T_2$. The relevant portions of the disclosure of the U.S. Pat. No. 5,212,447 patent are expressly incorporated herein for all purposes. The MRIL tool used in accordance with a preferred embodiment of the present invention stores multiple pulse sequences downhole, in a memory within the probe. These sequences are then activated by commands from the measurement time controller of the surface system. At the surface, raw tool data are separated into data streams and associated with the correct calibration and correction tables in data processor. An essentially unlimited number of pulse sequences can be used quasi-simultaneously, as described in more detail next. In an alternative preferred embodiment of the present invention the operation of the tool can be re-programmed on command from surface controller.

Signal Modeling and Corrections

In accordance with a preferred embodiment of the present invention several parameters which correspond to the gas and the oil phases of the formation are computed in real time. Due to the fact that logging conditions dynamically change during the course of a pass, correction for various factors, which may affect the accuracy of the measurements have to be made. In the following paragraphs, a brief discussion is presented on the specifics of the parameter computations and the required corrections used to estimate the relative quantities of gas and oil in a formation of interest.

Corrections for the Influence of $T_1$ on Diffusion Measurements.

It is known in the art that the static field gradient required for downhole diffusion measurements induces stimulated echo effects within a CPMG echo train. These stimulated echoes partially undergo $T_1$ relaxation and therefore benefit less from the re-focusing effects of repeated pi. pulses in a standard CPMG sequence. In accordance with a preferred embodiment of the present invention this problem can be treated by introducing the concept of "effective" relaxation times, as described in more detail next.

In particular, it is known that the classic Carr-Purcell expression for spin echo attenuation due to transverse relaxation and diffusion in a field gradient, using the standard notations above, is given by the expression:

$$M_{xy}(t) = M_0 \exp\left(\left(-\frac{t}{T_2}\right) + \left(\frac{1}{3}\gamma^2 G^2 \tau^2 Dt\right)\right) \quad (1)$$

and, strictly speaking, is valid only if: (a) the gradient G is small, or (b) if only the on-resonance portion of the spin spectrum is utilized. As indicated above, however, the MRIL tool operates with a relatively strong gradient field, on the order of about 15–25 G/cm. In addition, low signal-to-noise considerations make it necessary to utilize the full bandwidth of the tool, so that strong off-resonance effects are necessarily included in the echo signals. Thus, for example, even for the simplest $T_2/D$ experiment which requires at least two different pulse-echo spacings $\tau$ a correction in the expression in Eq. (1) is required in order to avoid systematic errors. Consequently, the observed echo decay signal has to be modeled as a complex superposition of longitudinal relaxation, transverse relaxation and different diffusion times.

Therefore, in accordance with the present invention, the signal observed at the N-th echo is modeled as a superposition of all possible combinations of transitions between transverse and longitudinal magnetization and is given by the expression:

$$M_{xy}(2\tau N) = M_0 \sum_{i=0}^{N} A_i \exp\left(-\frac{2\tau}{T_1}(N-i) - \frac{2\tau}{T_2}i - \left(N - \frac{2i}{3}\right)\gamma^2 G^2 D\right) \quad (2)$$

Using the expression in Eq. (2), the effect of diffusion dephasing is taken into account by introducing "effective" transverse relaxation times $T_1^\dagger$ and $T_2^\dagger$ given by the following expressions:

$$1/T_1^\dagger = 1/T_1 + \gamma^2 G^2 \tau^2 D$$

$$1/T_2^\dagger = 1/T_2 + 1/3 * \gamma^2 G^2 \tau^2 D \quad (3)$$

It can be shown that direct echoes (i=N) decay with a rate $1/T_2$; indirect echo decay (i<N) is controlled by $1/T_1^\dagger$ and by $1/T_2^\dagger$. Without diffusion, indirect echoes decay either slower or at the same rate as direct echoes. With very fast diffusion, however, indirect echoes drop out faster than direct ones. The effect on combined echo amplitudes primarily depends on the receiver's bandwidth and has been determined to require an about 15% correction at high diffusion rates.

It should be noted that the expressions for the effective relaxation rates in Eq. (3) refer to the echo decay process, and not to the recovery of longitudinal magnetization, which is controlled by $T_1$. For gases, both effective relaxation times are dominated by the diffusion term in a gradient field and therefore $T_1 \gg T_1^\dagger \approx T_2^\dagger/3$. In this case, the echo train decays slightly faster than expected, and an analysis based on the standard Carr-Purcell formula will overestimate the diffusion parameter D. This problem is corrected by inserting into the Carr-Purcell formula of an effective pulse-echo spacing $\tau_{eff}$, which incorporates the influence of both pulse width and receiver bandwidth:

$$1/T_2^\dagger = 1/3 * (\tau_{eff} \gamma G)^2 D \quad (4)$$

It has been determined that for the MRIL systems used in accordance with a preferred embodiment of the present invention, the ratio $\tau_{eff}/\tau = 1.08$, thus resulting in a 16% correction for calculated gas diffusivities.

Magnetic Field Gradient and Probe Temperature.

As evident from Eq. (4), the prediction of $T_2^\dagger$ in the gas phase generally requires knowledge of the field gradient G, which is dependent on the probe temperature. A specific example of measurements of the depth-of-investigation (diameter of the sensitive zone) and the magnetic field gradient values, as functions of probe temperature, are summarized in Table 1.

TABLE 1

Sensitive diameter and magnetic field gradient of an MRIL ®/C 6" tool as functions of probe temperature.

| Temperature | Diameter | Field Gradient |
|---|---|---|
| 25° C. | 40.6 cm | 16.6 G/cm |
| 50° C. | 39.7 cm | 17.0 C/cm |
| 75° C. | 38.9 cm | 17.4 G/cm |
| 100° C. | 37.8 cm | 17.9 G/cm |
| 125° C. | 36.8 cm | 18.4 G/cm |
| 150° C. | 35.8 cm | 18.9 G/cm |

Typical values used in Eq. (4) are $\tau_{eff} = 0.65$ ms, $\gamma = 26750$ s$^{-1}$ G$^{-1}$, and G=18 G/cm. Probe temperature, as reported by a sensor embedded in the permanent magnet of the MRIL tool, is always recorded, which allows the calculation of the field gradient G at any point on the log.

3) Parameterization of HI, $T_1$ and $T_2$

The matched filter signal processing method of the present invention, described in more detail below, requires the calculation of hydrocarbon (oil and gas) signatures. These components are assumed to be the non-wetting phase, i.e., to be generally characterized by their bulk relaxation properties. As known in the art, the effects of temperature and pressure on $T_1$ and D of the gas phase substantially cancel each other, resulting in fairly stable and predictable values for both parameters, for which mathematical expressions are available. On the other hand, the corresponding values for the oil phase are generally dependent on the formation and are determined in accordance with the present invention from sample measurements conducted prior to the logging experiment.

In particular, the hydrogen index (HI) of oil is assumed to be 1.0. The measured drop in NMR porosity is typically observed in gas zones, because $HI_g < 1$. Most natural gases are predominantly methane. FIG. 28A shows $HI_g$ variations between about 0.2 and 0.6 for a methane gas under typical conditions. In overpressured reservoirs HIg can be about 0.7. Accordingly, the gas HI is sufficient to give readily detectable signals from gas. For methane gas, in accordance with a preferred embodiment of the present invention the corresponding index $HI_g$ is estimated mathematically using the expression 2.25×$\rho$, where $\rho$ is the gas density in g/cm$^3$, calculated by solving the equation of state. For gases other than methane, or for mixed gases, the multiplying factor is less than 2.25. For example, for a typical gas mix, characterized as $C_{1.1} H_{4.2}$, the factor becomes 2.17. In an alternative preferred embodiment of the present invention, the hydrogen index of different hydrocarbons can also be estimated using the expressions presented, for example, in "Schlumberger: Log Interpretation Principles/Applications," Schlumberger Educational Services, 1989, pp. 5–20 and 5–21, the content of which is expressly incorporated herein.

A simple power law has been found sufficient to fit published laboratory data for longitudinal relaxation time $T_1$ of methane gas, as well as log data. The expression used in accordance with the present invention is:

$$T_{1,g} = 25 \times 10^3 \rho / T^{1.17} \quad (5)$$

where $T_1$ is measured in seconds, the density $\rho$ in g/cm$^3$ and the absolute temperature T is in degrees Kelvin. Eq. (5) is valid for gas densities up to about 0.3 g/cm$^3$; higher densities generally approaching a liquefied gas state.

The non-wetting oil phase relaxes with its bulk relaxation $T_{1,o}$, which is determined, for example, by using viscosity measurements of a sample. It has been determined that in order to successfully detect liquid hydrocarbons, for the $T_1$-weighted measurements in accordance with the present invention a long $T_1$ component (low viscosity) on the order of 1–2 s is necessary. The relatively large values for the parameter $T_1$ of light hydrocarbons provide a mechanism for distinguishing these fluids from water, since $T_1$ of water in rocks is almost always less than about 500 msec. In partially hydrocarbon-saturated water wet rock the hydrocarbon-water contrast is even better because $T_1$ (and $T_2$) of water are shorter, due to the fact that water typically resides in the smallest pores.

Figure 29G:
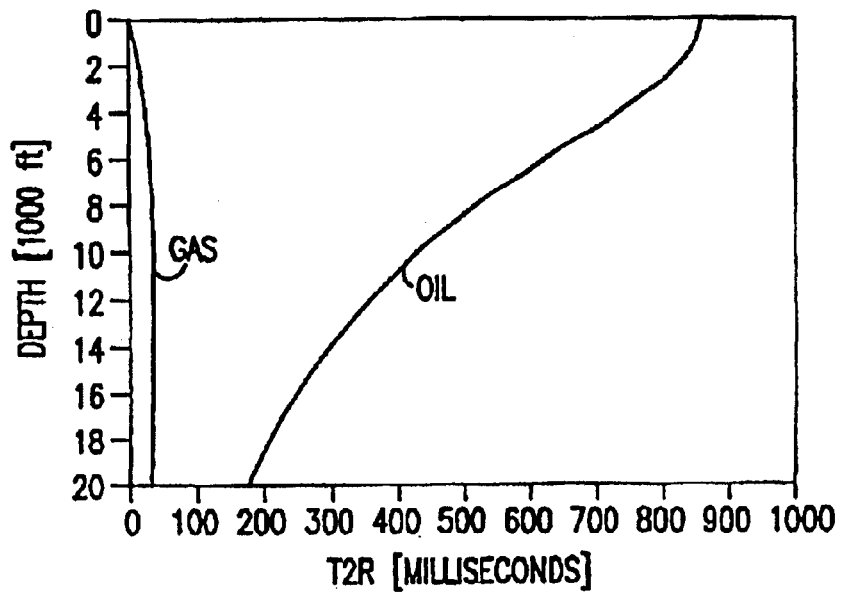
FIG. 29G illustrates the measured $T_{2R}$ for gas and oil as a function of logging depth.
Figure 29A:
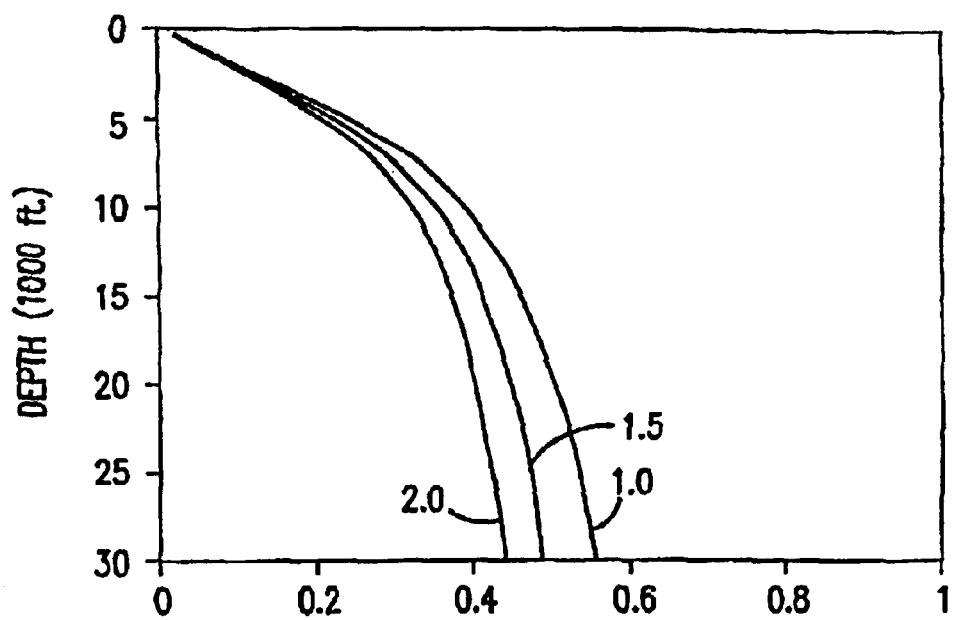
FIG. 29A shows the hydrogen index (HI) of methane as a function of depth at temperature gradients of 1, 1.5 and 2° F./100 ft.
Figure 29B:
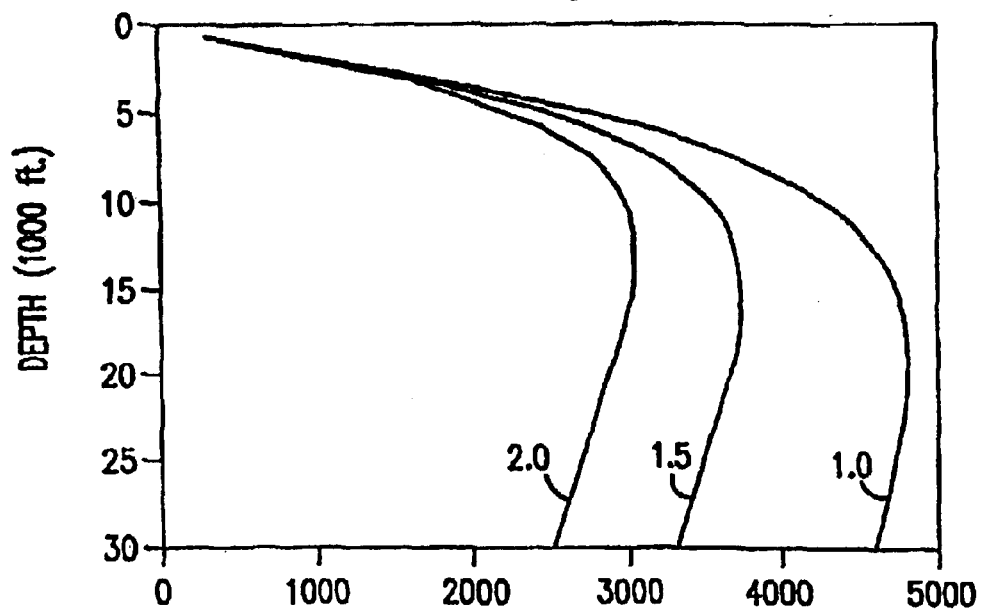
FIG. 29B shows the dependency of the longitudinal relaxation time $T_1$, as a function of depth at temperature gradients of 1, 1.5 and 2° F./100 ft, and pressure gradient of 43.3 psi/100 ft.
Figure 29C:
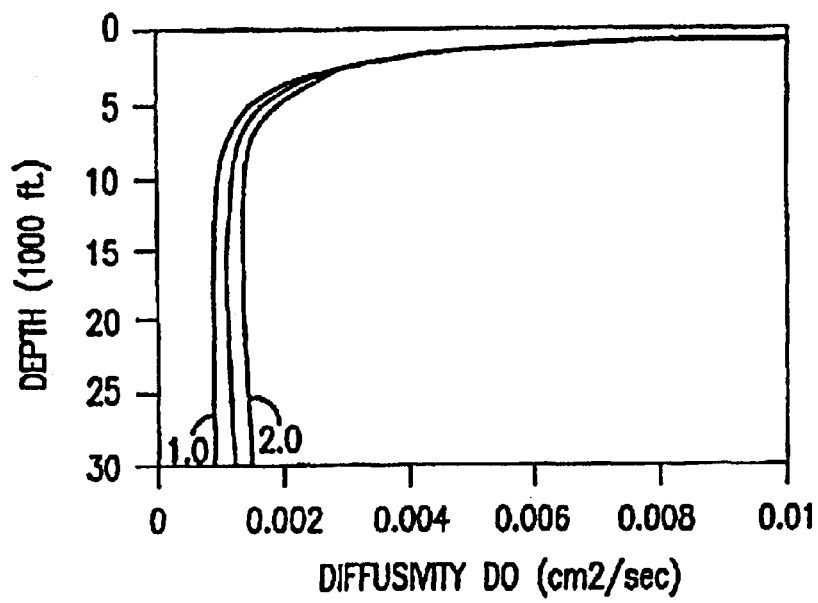
FIG. 29C shows the dependency of the self-diffusion coefficient $D_0$ of methane as a function of depth at temperature gradients of 1, 1.5 and 2° F./100 ft.
Figure 29D:
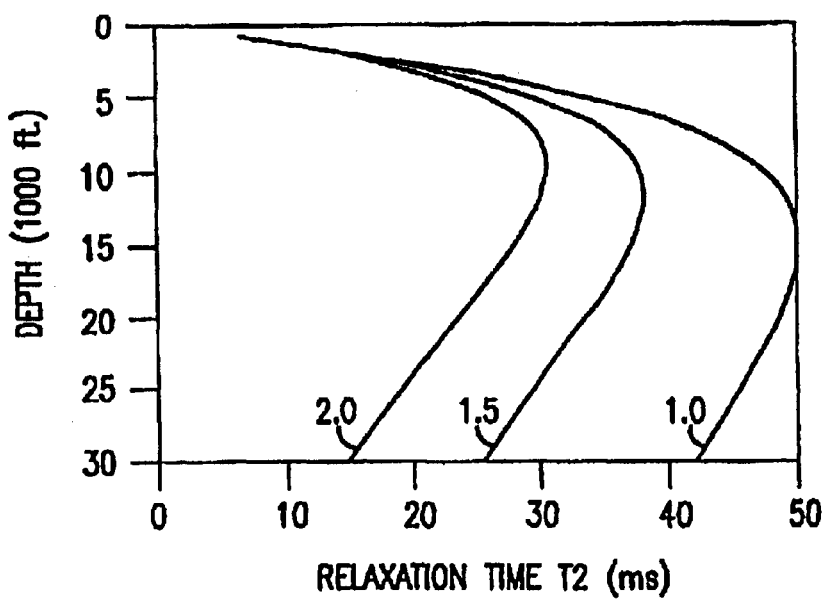
FIG. 29D shows the apparent transverse relaxation time $T_2$*based on diffusivity $D_0$ as in FIG. 29C, diffusion restriction $D/D_0$, and magnetic field temperature gradient of $-0.18\%/°$ C.
Figure 29E:
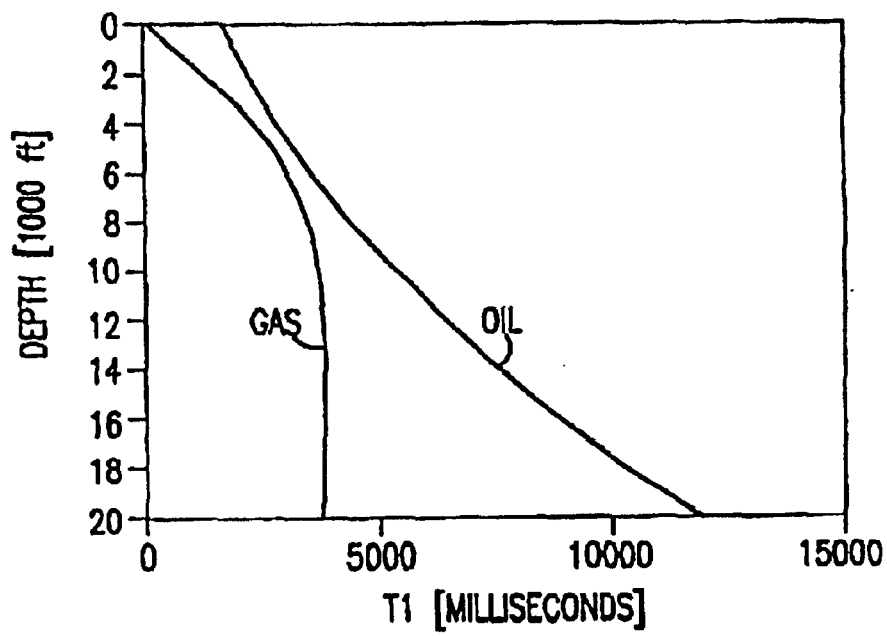
FIG. 29E shows values for the $T_1$ parameter of methane gas and light oils as a function of logging depth.

FIG. 29E shows, on the other hand, values for the $T_1$ parameter of gas (methane) and light oils at depths below 4000 feet. Both curves were computed assuming a geothermal gradient of 1.5° F./100 feet. The oil curve was computed assuming a temperature-dependent viscosity, using the expression $\eta = \eta_0 \exp(Q/RT)$, where $\eta_0 = 0.01$ cp, $Q=10.5$ kJ/mol and $R=8.314$ J/mol/K. As seen in the figure, due to different relaxation mechanisms, $T_1$ for methane can be relatively short, i.e., between about 2.5 and 4 seconds, while in the specific example $T_1$ for oil can be very long (on the order of 10 sec). Standard logging practice requires to set the wait time between successive CPMG pulse trains long enough for substantially full recovery (about 95%) of the longitudinal magnetization. Accordingly, waiting times for a particular measurement have to be adjusted dependent on the specific oil.

The apparent diffusivity D of a fluid depends both on the self-diffusion coefficient $D_0$ and the restrictions imposed by the pore space. In accordance with a preferred embodiment of the present invention, an experimental temperature and density relationship for unrestricted gas diffusion $D_{0,g}$ is used, which can be expressed mathematically as:

$$D_{0,g} = 8.5 \times 10^{-7} T^{0.9}/\rho, \quad (6)$$

where $D_{0,g}$ is measured in cm$^2$/s, the temperature T is measured in degrees Kelvin and the density $\rho$ in expressed in g/cm$^3$. Below 7,000 ft, the opposing effects of temperature and pressure stabilize the diffusion parameter $D_0$ at a value of about $10^{-3}$ cm$^2$/s. Diffusion restriction in the pore space should also be taken into account since the diffusion length (given by sqrt($2\tau D_0$)) is approximately equal to 10 μm. $D/D_0$ ratios in rock samples at this length scale have been observed ranging from about 0.55 (Indiana limestone) to about 0.9 (oomoldic limestone). Sandstone samples have been found to cluster in a tight $D/D_0$ ratio range of 0.7–0.8, which is consistent with experimental observations of $T_{2,g}^{\dagger}$ from log data.

Because of diffusion, the intrinsic relaxation rate $1/T_{2,g}$ for gas is negligible compared to $1/T_{2,g}^{\dagger}$ (see Eq. (3)). Similarly, the diffusivity of the oil phase is small compared to that of the gas phase. Consequently, the parameters $T_{2,o}$ and $T_{2,o}^{\dagger}$ which are used in the matched filter expression considered next are much larger than both $T_{2,g}^{\dagger}$ and also much larger than the total acquisition time required to separate oil from gas signals. As indicated above, numerical values for these parameters can be obtained, for example, from sample measurements.

Figure 29F:
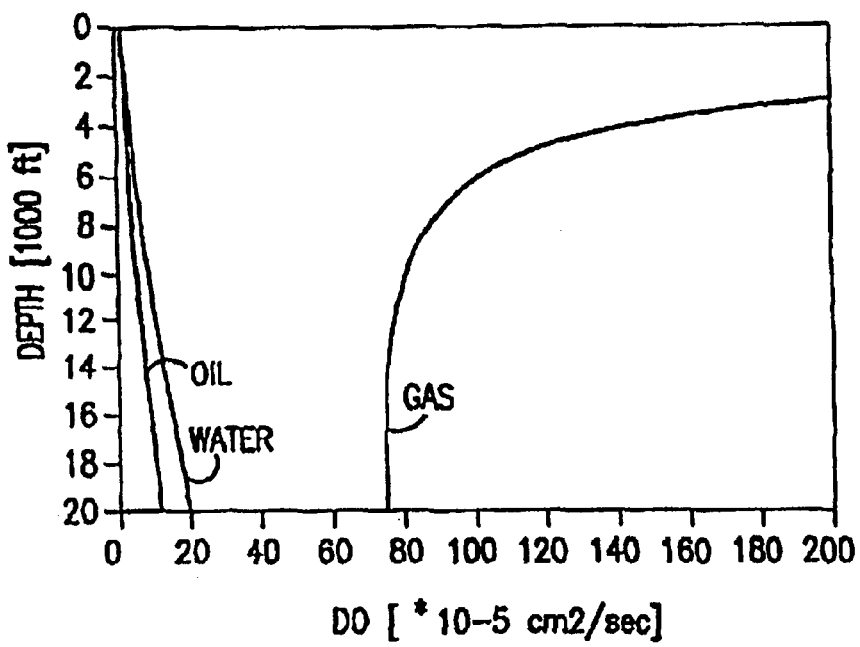
FIG. 29F illustrates the self diffusion coefficients $D_0$ for methane, water and light oil as a function of logging depth.

FIG. 29F illustrates the self diffusion coefficients $D_0$ for methane, water and light oil. All curves are based on geothermal gradient of $1.5_0$ F/100 feet, and (for gas) a hydrostatic pressure pressure. As seen, the methane $D_0$ is at least about 50 times larger than that of water and light oil. The resulting contrasts in the measured $T_2$ (i.e., $T_{2r}$) for gas compared to oil are shown in FIG. 29G. The plots include the effect of temperature and pressure on $T_1$ (see FIG. 29E) and D (see FIG. 29F) for both fluids and the effect of temperature on the parameter G for the tool. Moderate restriction diffusion effect on gas and no restriction effects on oil diffusion was assumed, i.e., $(D/D_0)_g = 0.7$; $(D/D_0)_o = 1$, Comparison of FIGS. 29E and 29G reveals that gas has a high ratio $T_1/T_2$ (larger than about 200) at all depths, which is a characteristic signature of gas. For light oil, however, this ratio is approximately equal to one and rises slowly with increased depth.

Table 2 summarizes expressions for the parameter estimates of different fluids used in accordance with a preferred embodiment of the present invention.

TABLE 2

| Fluid | Spin Lattice Relaxation (sec) | Self Diffusion coeff. (cm$^2$/sec) | parameters/units |
|---|---|---|---|
| Methane | $T_{1,g} = 25 \cdot 10^3$ $\rho/T^{1.17}$ | $D_{0g} = 8.5 \cdot 10^{-7} T^{0.9}/\rho$ | Gas density $\rho$ in gramm/cc; T-abs temp in Kelvin |
| Oil | $T_{1,o} = 1.2(T/298)/\eta$ | $D_{0,o} = 1.3(T/298)/\eta$ | $\eta$ is oil viscosity in cp; T-abs temp in Kelvin |
| Water | $T_{1,w} = 3(T/298)/\eta$ | $D_{0,w} = 1.2(T/298)/\eta$ | Same as above |

For illustrative purposes, examples of pre-calculated values for HI$_g$ diffusivity and the relaxation time parameters $T_{1,g}$ and $T_{2,g}^{\dagger}$ as functions of depth are shown in FIGS. 29A to 29D. In particular, FIG. 29A shows the hydrogen index (HI) of methane as a function of depth at different temperature gradients; FIG. 29B shows the dependency of the longitudinal relaxation time $T_1$ as a function of depth at temperature gradients of 1, 1.5 and 2° F./100 ft, and pressure gradient of 43.3 psi/100 ft; FIG. 29C shows the dependency of the self-diffusion coefficient $D_0$ of methane as a function of depth; and FIG. 29D shows the apparent transverse relaxation time $T_2^{\dagger}$ based on diffusivity $D_0$ as in FIG. 29C, diffusion restriction $D/D_0$, and magnetic field temperature gradient of –0.18%/° C.

In the examples shown in FIGS. 29A–D, a hydrostatic pressure gradient of 43.3 psi/100 ft and temperature gradients of 1, 1.5 and 2° F./100 ft were assumed, as shown. Additional parameters used in the examples include: frequency=720 kHz, $T_{eff}=0.65$ ms and $D_g/D_{0,g}=0.8$. The tool and the formation temperature were assumed to be equal. It can be seen from FIGS. 29B and 29D that functionally the curves for $T_1$ and $T_2^{\dagger}$ are similar and that the ratio $T_1/T_2^{\dagger}$ stays within narrow limits for a wide range of temperatures and logging depth.

Data Acquisition

Figure 27:
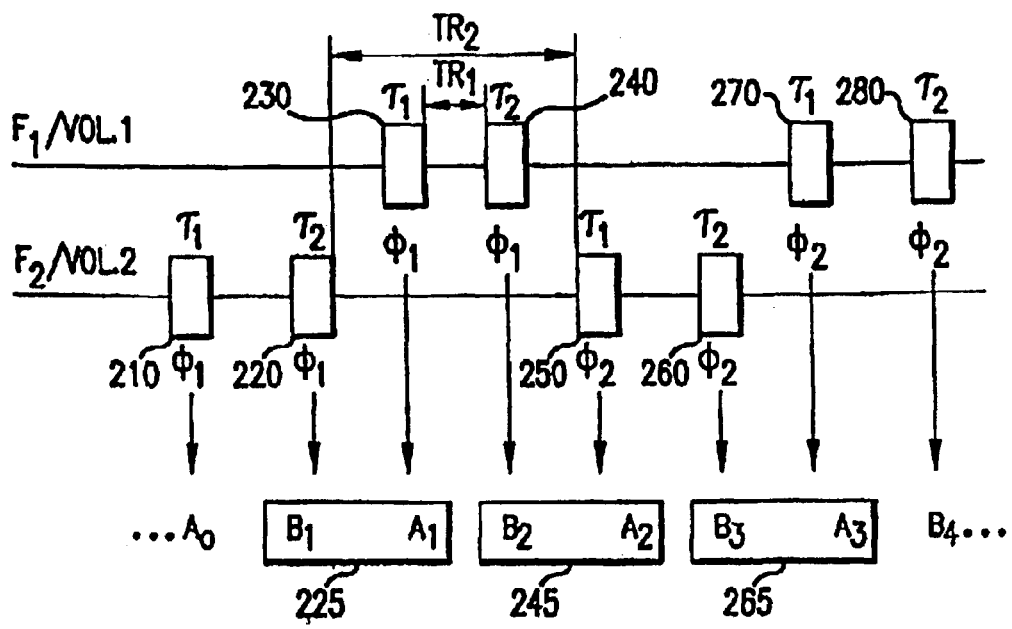
FIG. 27 illustrates an example cycle of pulse sequences in accordance with a preferred embodiment of the present invention for estimating diffusion and removing various phases, such as oil, gas, and/or water by suitable selection of recovery times.

As indicated above, the MRIL® tool of the present invention is capable of performing separate, quasi-simultaneous measurements in different sensitive volumes by simply switching the operating frequency of the tool by a small amount. In accordance with a preferred embodiment of the present invention, this multi-frequency capability of the MRIL® tool is used to provide a new data acquisition method which is particularly suitable for the detection of gas on the basis of NMR measurements with different recovery times $T_{R1}$. To this end, with reference to FIG. 27, a novel interleaved pulse sequence is proposed in which at least two CPMG pulses 210 and 220 associated with resonant frequency $F_2$ are followed by at least two CPMG pulses 230, 240 associated with a different resonant frequency $F_1$. As shown in FIG. 27, the NMR measurement is continued next using at least two new pulses 250, 260 at the initial resonance frequency $F_2$, followed by at least two separate pulses 270, 280 at the $F_1$ frequency. Due to the fact that resonant frequency $F_1$ excites protons only in volume 1 of the formation and resonant frequency $F_2$ excites protons only in volume 2 of the formation, pairs 225, 245, 265, etc., of independent complex data points can be collected at each depth mark. As shown for illustrative purposes in FIG. 27, the first data point in each pair, generally designated as $B_i$, corresponds to a short recovery time $T_{R1}$, while the second data point, generally designated as $A_i$, corresponds to a long recovery time $T_{R2}$.

Thus, using the data acquisition sequence illustrated in FIG. 27, by "hopping" the resonance frequency $F_i$ of the tool, and alternating between adjacent resonant volumes of the formation one can obtain a sequence of signal pairs, each pair corresponding to substantially the same depth mark in the formation, but measured at different recovery times. It should further be noted that data for two different recovery times need not necessarily be obtained from only two different frequencies. For example, two or more measurements associated with different frequencies can be combined (i.e., averaged) to result in a single data stream corresponding to either a short, or a long recovery time. Furthermore, it should be clear that by using more than two resonance frequencies, and applying a correspondingly larger number of pulses in each resonant volume, the data acquisition method of the present invention can easily be extended to the more general case of M-tuple measurement data sets, each measurement point corresponding to a different recovery time $T_{R1}$.

The interleaved multi-frequency data acquisition method described above is clearly preferable to prior art methods, which require separate logging passes, because it provides a simple approach to dealing with depth alignment problems. Preferably, the pulse sequences in FIG. 27 systematically alternate the roles of all sensitive volumes (and pulse phases) in order to negate any systematic difference between operating frequencies.

The data acquisition method was described above with reference to identical CPMG sequences, which mode is referred to in the present application as $T_1$-weighted acquisition. Data from this acquisition mode is suitable for the Differential Spectrum Method (DSM) described in the Akkurt et al. paper. Notably, however, the method is also suitable for direct signal subtraction in the time domain, as described in more detail next.

In an alternative preferred embodiment of the present invention, a novel data acquisition mode referred to as $T_1$-and diffusion-weighted acquisition can also be used. As indicated above with reference to the SSM method discussed in the Akkurt et al. paper, the contrast between liquid and gas signals can be enhanced by using a slightly larger pulse-echo spacing for the CPMG train associated with the shorter recovery interval. This embodiment is illustrated in FIG. 27 using two different intervals $\tau_i$ for each successive pulse in the same resonance volume. It has been found, however, that it is not necessary to eliminate the gas signal altogether. For example, an increase by only 40% in the pulse echo $\tau$ has been found to cause a 50% decrease in the diffusion-induced part of $T_2$. As indicated above with reference to the SSM method, because of diffusion dominance, the effect is much more pronounced for gases than for liquids, and can accordingly be used to enhance the separation of the two phases.

Further details of the construction and operation of the tool used in accordance with a preferred embodiment of the present invention can be found in U.S. Pat. Nos. 4,710,713 4,717,876; 4,717,877; 4,717,878; 5,212,447; 5,280,243; 5,309,098; 5,412,320; 5,517,115, 5,557,200 and 5,696,448. The content of the above patents is hereby expressly incorporated by reference. It will be appreciated that while the MRIL® tool is used in a preferred embodiment, any other tool notably the CMR and CMR-Plus tools by Schlumberger, or other available tools, such as those by Baker-Atlas and Computalog, as well as logging-while-drilling (LWD) tools, appropriately programmed, can also be used in alternative embodiments.

II. The Methods

In accordance with one aspect of the present invention, a novel approach is proposed for reducing the level of non-formation signals, i.e., ringing, in which ringing signals are characterized and removed from the underlying NMR pulse echo signals in separate steps. Once the estimated ringing component is removed from the acquisition sequence(s), in accordance with one embodiment of the invention, standard NMR processing methods are applied to derive petrophysical properties of the formation being investigated. In accordance with another aspect of the invention, which is described in Section D below, additional pre-processing is applied to the signal to further improve the resolution of the tool.

First is considered a method for reducing the level of ringing in the signal for a given signal-to-noise ration (SNR) using a multi-step approach. In a preferred embodiment, there are three conceptual steps, broadly designated: Ringing Estimation; Ringing Elimination; and Experiment Stacking.

A. Ringing Estimation

In a preferred embodiment of the invention, an estimated ringing level for each measurement is obtained in the Ringing Estimation step through use of a three-operation process. The three operations include: (a) providing a Basic Ringing Estimate; (b) providing an Echo Time Average; and (c) computing a PAP Mean Ringing Average.

A.1. Basic Ringing Estimate

In accordance with the present invention, two methods are proposed for determining the Basic Ringing Estimate. In a first, preferred method, computing the Basic Ringing Estimate is a data-driven determination from the echo-trains that comprise the phase-alternated pairs (PAPs). In accordance with an alternative embodiment, the Basic Ringing Estimate is computed using a direct measurement (DM) of the ringing from a special "ringing echo-train" acquired immediately before or after a normal echo-train.

A1.a. Basic Ringing Estimate [PAP]

The Basic Ringing Estimate [PAP] operation in accordance with the preferred embodiment comprises summing the current measurement CPMG spin echo train with one of more of the current measurement's PAP CPMG echo trains. This operation is performed on an echo by echo basis for each Phase Alternate Pair separately, which results in one or more basic ringing estimate vectors, the length of which is determined by the length of the echo trains.

In particular, in a preferred embodiment the method uses the current measurement CPMG (denoted $CPMG_0$—which is a vector having N elements, where N is the length of the spin-echo sequence) with the two nearest CPMG echo trains, with which it forms PAPs, i.e., the "preceding" alternate phase echo train ($CPMG_{-1}$) and the "following" alternate phase echo train ($CPMG_{+1}$)—to create two estimates of the basic ringing estimate vectors, each having N elements. Mathematically, the basic ringing estimates can be expressed as follows:

$$\text{Ringing}_{-1} = \frac{CPMG_0(n) + CPMG_{-1}(n)}{2} \quad \text{Eqn. (7)}$$

$$\text{Ringing}_{+1} = \frac{CPMG_0(n) + CPMG_{+1}(n)}{2}$$

Because the CPMG echo trains are acquired in quadrature, it will be appreciated that the operations described above, and in subsequent equations, are performed in the complex domain, i.e., by treating separately the real and imaginary signal input channels.

Assuming that the CPMG echo-trains acquired at a single frequency can be represented by the following sequence relative to some arbitrary starting sample at 0:

. . .
$-S_{-3}+O$
$S_{-2}+O$
$-S_{-1}+O$
$S_0+O$
$-S_{+1}+O$
$S_{+2}+O$
$-S_{+3}+O$
. . .

where $S_0$ is the formation signal at depth 0, O is the tool-generated non-formation signal, and the signs are arranged such that each adjacent pair is a PAP. In the notation used above, $CPMG_0$ is equal to $S_0+O$, and necessarily contains random or thermal noise that arises in both the formation and non-formation signals. The random noise component is omitted for convenience.

Using Eqn. (7), the 2 PAPs incorporating $(S_0+O)$ are summed in such a manner that they yield (in vector notations):

$$\left( \frac{(\bar{S}_0 - \bar{S}_{-1}) + 2\bar{O}}{2} + \frac{(\bar{S}_0 - \bar{S}_{+1}) + 2\bar{O}}{2} \right) \Big/ 2$$

where the bar superscript denotes the Echo Time Averaging described in more detail below.

The expression above, which describes the MeanRingingAverage from the third processing step can then be simplified to:

$$\bar{O} + \frac{2\bar{S}_0 - (\bar{S}_{-1} + \bar{S}_{+1})}{4}.$$

As can be seen, the MeanRingingAverage includes some information about the formation. Specifically, it carries information about the change in formation signal—as represented by $\bar{S}$—over a depth interval comprising two PAPs. If $\bar{S}$ varies linearly with depth over the scale of two adjacent PAPs—three adjacent echo-trains at the same frequency—then the formation signal present in the MeanRingingAverage cancels out and the only component remaining is the non-formation signal, $\bar{O}$.

As an example of a practical case in which the formation signal disappears from the MeanRingingAverage, consider the situation at the boundary between two "thick" beds; where "thick" in this case means having a thickness greater than the antenna aperture of the tool. If CPMG−1 and CPMG+1 are measured one antenna aperture apart and straddling the boundary, then CPMG0 will be the mean of the CPMG echo-trains above and below: In this case, $\bar{S}$ will vary linearly with depth and MeanRingingAverage will be given simply by $\bar{O}$. It should be noted that, in the preferred embodiment described above, the non-formation signal is assumed to be constant, having a value which may be a complex number.

While the preferred method described above uses two PAPs, it will be appreciated that there is no implied limitation on the maximum number of PAPs that could be used. Similarly, while the preferred method creates two Ringing Estimates, there is no implied limitation as to this number, since a single Ringing Estimate could be computed from a single PAP and can be used for the subsequent operations instead. It should also be apparent that more than two estimates can be formed at this time in alternative embodiments.

A1.b. Basic Ringing Estimate [DM]

In accordance with the direct measurement embodiment of the present invention, a Ringing Estimation Pulse Sequence (REPS) is used to determine directly the Basic Ringing Estimate. The Basic Ringing Estimate [DM] simply makes a separate measurement with a CPMG pulse sequence specifically designed to produce the ringing signal alone (designated as $RING_0$) without any other external or formation signal. In this case, $Ringing_0$, which is the ringing signal associated with the current sequence $CMPG_0$, is directly obtained from the CPMG sequence, using the expression:

$$Ringing_0(n) = RING_0(n) \quad \text{Eqn. (8)}$$

In a preferred embodiment, the REPS sequence that can be used is a CPMG sequence without an initial $\pi/2$ pulse. It will be appreciated by those skilled in the art that such sequence will create an echo-train that contains no formation signal, but which contains the needed information to characterize the non-formation signals.

Accordingly, in a preferred embodiment the REPS is a short sequence (10 to 30 echoes) of $\pi$ pulses. The sequence is substantially identical to the CPMG sequence used in the standard measurement, except that it contains fewer 180 degree (i.e., $\pi$) pulses and no 90 degree pulse. That is, the REPS sequence should be a string of $\pi$ pulses with the same separation as in the following (or preceding) CPMG measurement sequence and the same pulse shape. Preferably, the sequence is run for every frequency used in the operation of the multi-frequency tool. Generally, REPS is run during the wait time between CPMG measurement sequences. The exact location depends on the activation being run as it depends on tool power/energy being available.

Figure 3:
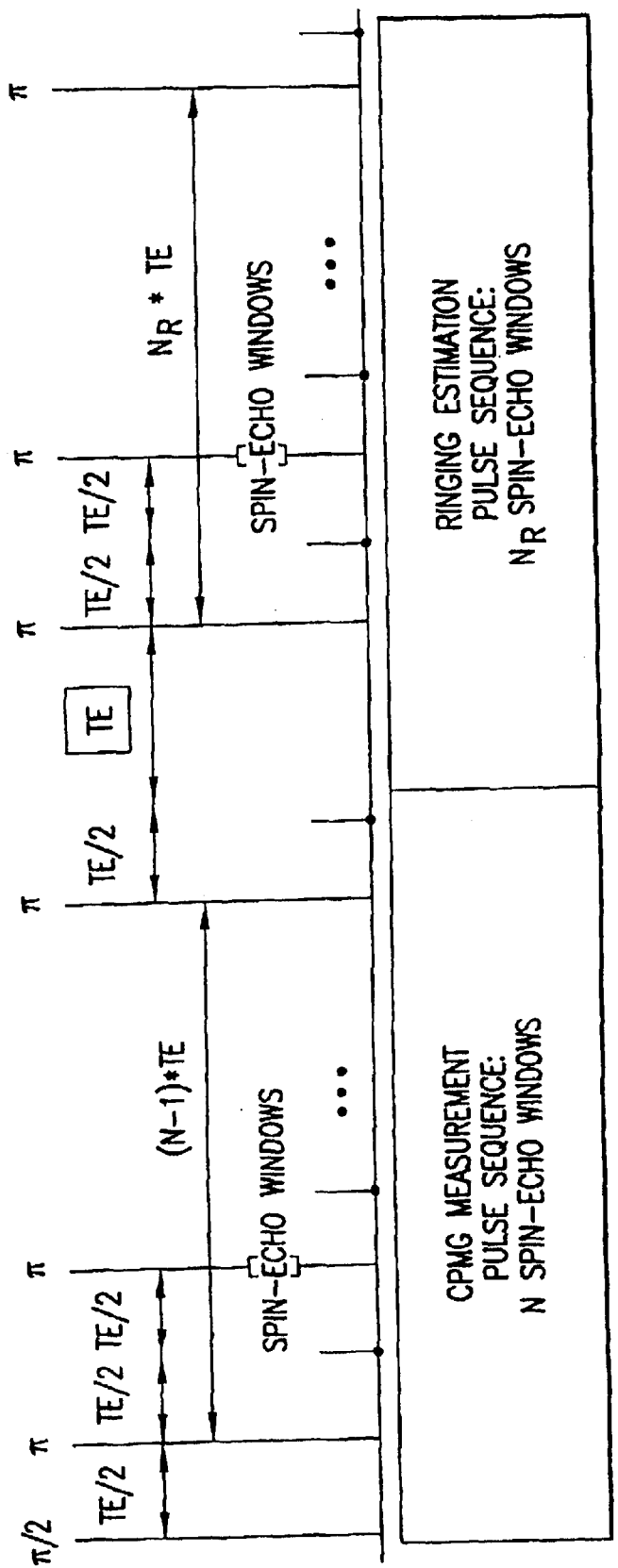
FIG. 3 is an illustration of a standard CPMG sequence along with a ringing estimation pulse sequence (REPS) used in a direct measurement of ringing signal contribution in accordance with a specific embodiment of this invention.
Figure 4A:
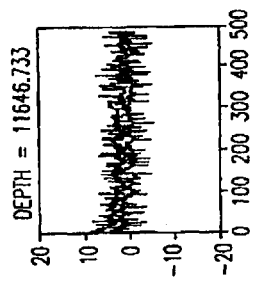
FIG. 4 illustrates intermediate results for the Ringing Estimation step and results after Ringing Elimination step (step 2) used in a preferred embodiment of this invention.
Figure 4B:
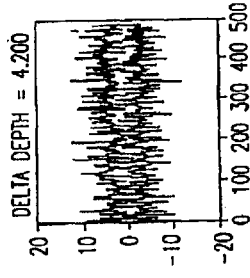
Figure 4C:
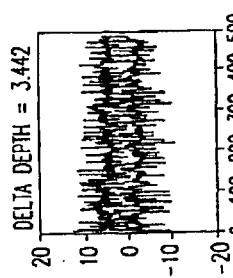
Figure 4D:
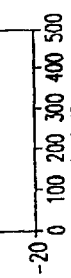
Figure 4E:
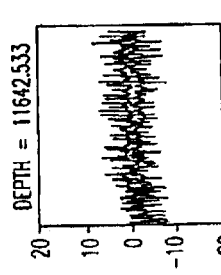
Figure 4F:
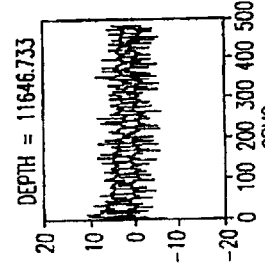
Figure 6:
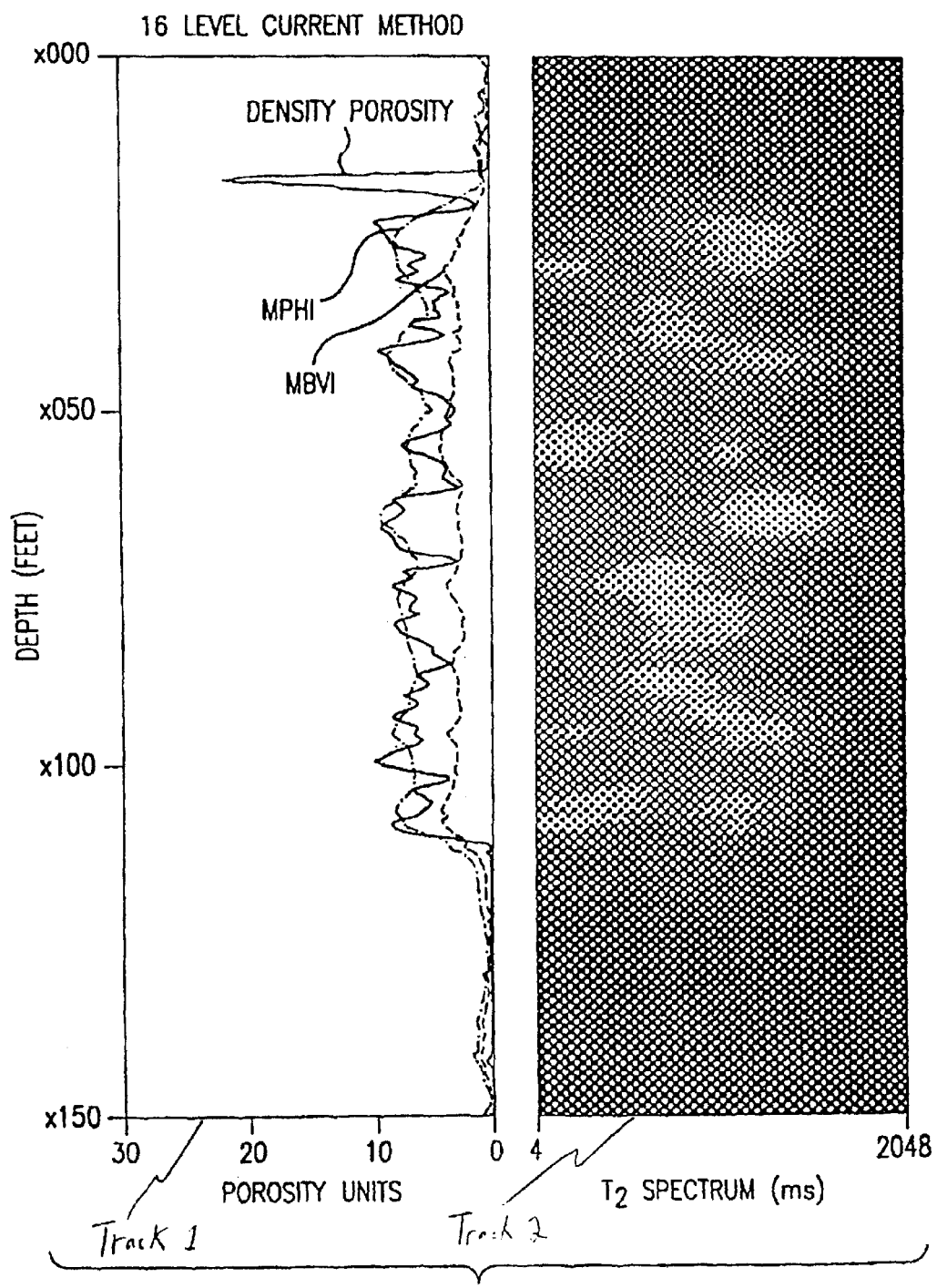
FIGS. 6 through 10 illustrate how different amounts of experiment stacking impact the vertical resolution of a section of log data in accordance with the present invention.
Figure 7:
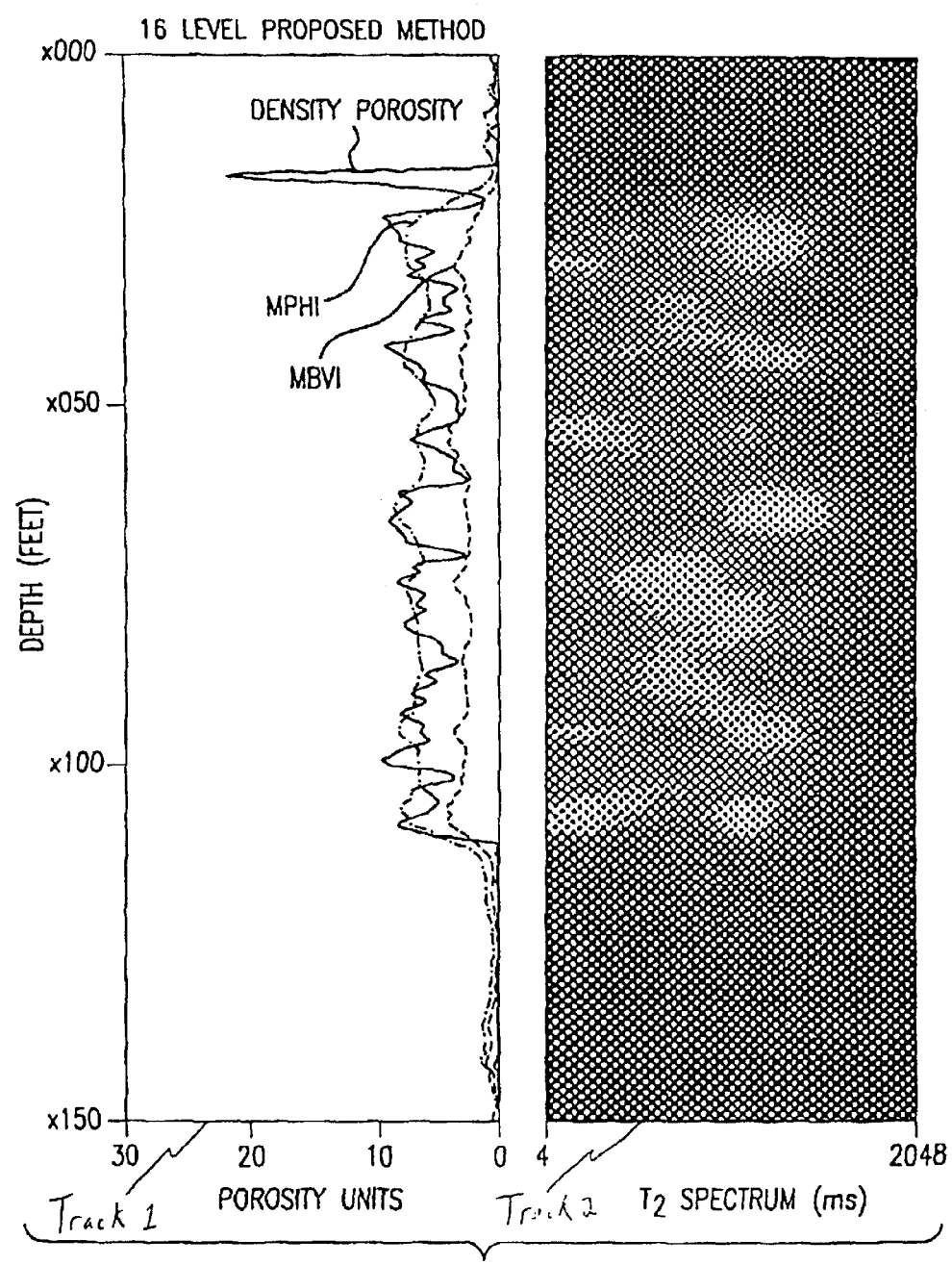
Figure 8:
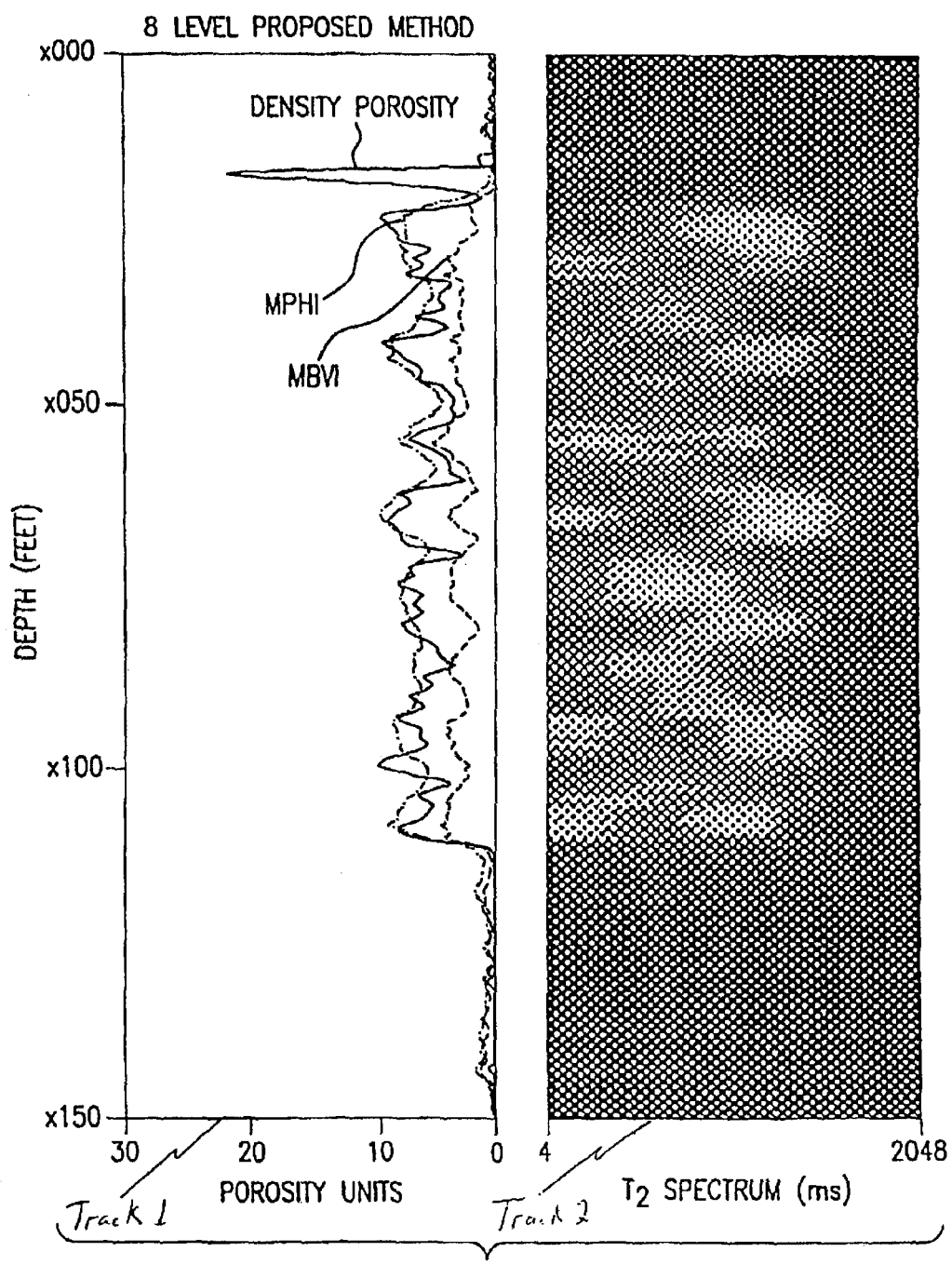
Figure 9:
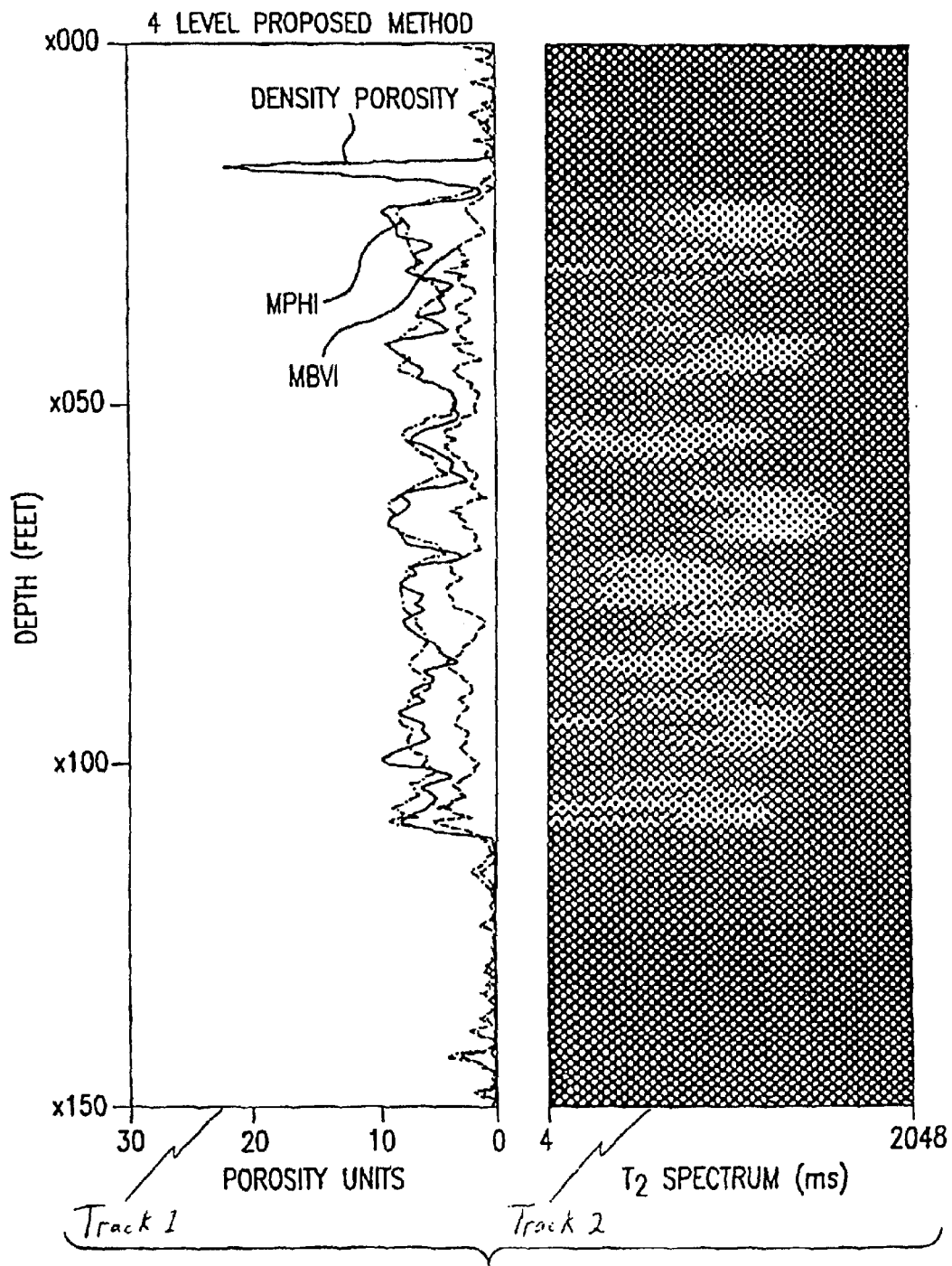
Figure 10:
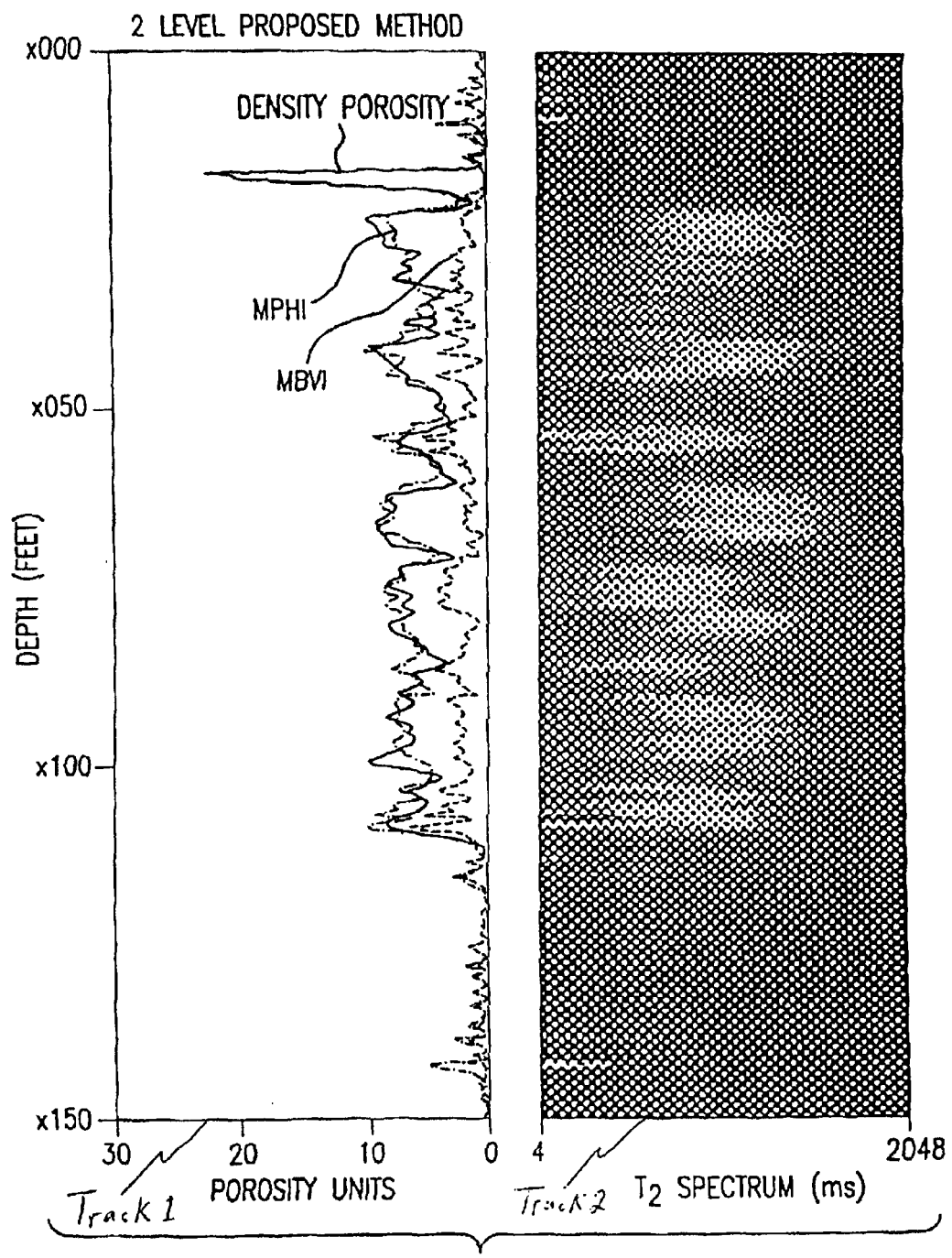
Figure 11B:
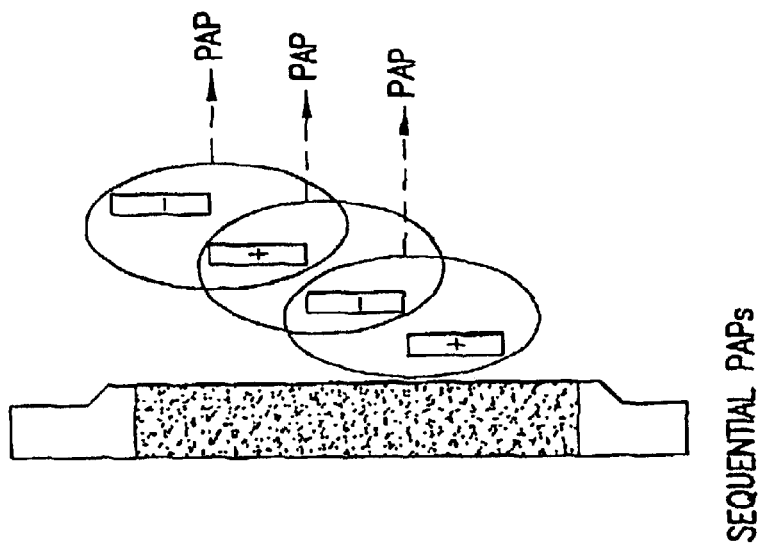
FIGS. 11A and 11B illustrate overlapping phase alternated pairs (PAPs) and sequential PAPs.
Figure 11A:
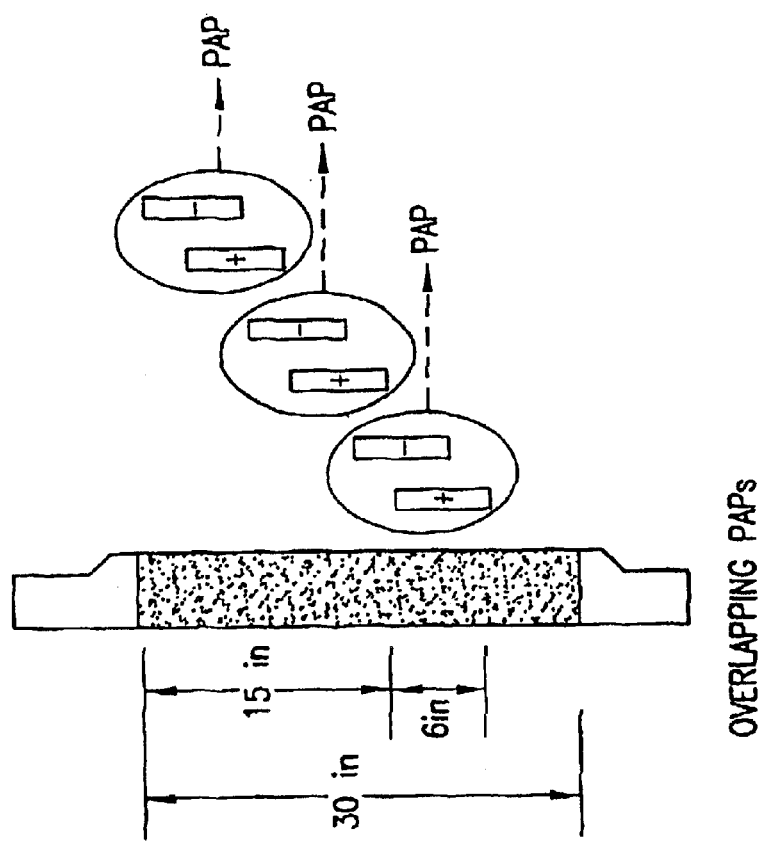

The REPS used in this embodiment of the invention is illustrated in FIG. 3. As shown, in the a timing diagram that illustrates an embodiment of a standard "CPMG Measurement Sequence"—presumably acquired after some build-up time $T_W$—followed by a "Ringing Estimation Sequence". Also shown in the drawings are the windows at which spin-echoes are acquired an interval $T_E/2$ after the $\pi$-pulses. As noted above, in the Ringing Estimation sequence, the measurements made in the spin-echo windows will actually be of the ringing signal and not of the formation spin-echoes.

The preferred embodiment shows the Ringing Estimation Sequence following the CPMG Measurement Sequence, with the first $\pi$-pulse occurring an interval $T_E$ after the last spin-echo window in the CPMG Measurement Sequence. The Ringing Estimation Sequence differs from the CPMG Measurement Sequence in that the first $\pi/2$-pulse is omitted, and in that the number of echoes in the Ringing Estimation Sequence (Nr) is not necessarily the same as the number of echoes in the CPMG Measurement Sequence (N). N and Nr are set according to the need to characterize separately the formation signal (N) and the ringing signal (Nr). It will be appreciated that in alternative embodiments of the invention the direct measurement sequence may precede the CPMG measurement sequence.

A.2. Echo Time Average

In accordance with the present invention, the Echo Time Average operation provides one or more mean ringing estimates. Broadly, the operation comprises calculating the average value of the basic ringing estimate vectors determined in the Basic Ringing Estimate operation described in Section A.1. above. In particular, in accordance with a preferred embodiment, the computation is mathematically expressed as follows:

$$MeanRinging_{-1} = \frac{1}{N}\sum_{n=1}^{N} Ringing_{-1}(n) \qquad \text{Eqn. (9)}$$

$$MeanRinging_{+1} = \frac{1}{N}\sum_{n=1}^{N} Ringing_{+1}(n).$$

In the event that the Basic Ringing Estimate [DM] method has been used, then only one summation is needed:

$$MeanRinging_0 = \frac{1}{N}\sum_{n=1}^{N} Ringing_0(n). \qquad \text{Eqn. (10)}$$

In the preferred embodiment expressed mathematically in Eqn. (9) and (10), all of the basic ringing estimate vector elements being used for calculating the average values are computed, yielding a single possibly complex number, which is an estimate of the contribution of non-formation, i.e., ringing signals. In the most general case it is unlikely that ringing will remain constant over the course of the NMR measurement or even over the course of a sequence. Accordingly, in alternative embodiments of this invention one or more subsets of the vector elements could be used instead, thereby generating a slowly developing complex function, which may be expected to more closely estimate the ringing phenomenon. It will be appreciated that if more than one subset is used, then MeanRinging will be cast as a complex-vector.

A.3. PAP Mean Ringing Average

In a preferred embodiment, the PAP Mean Ringing Average operation consists of combining one or more of the mean ringing estimates determined in the Echo Time Average Operation. This operation calculates the final estimated ringing level by calculating the mean of the separate mean ringing estimates, expressed mathematically as follows:

$$MeanRingingAverage = \frac{MeanRinging_{+1} + MeanRinging_{-1}}{2}. \qquad \text{Eqn. (11)}$$

In the event that the Basic Ringing Estimate [DM] method has been used, then MeanRingingAverage is identical to $MeanRinging_0$. In the event that MeanRinging is a complex-vector, then the method for computing MeanRingingAverage results in a complex-valued vector.

In accordance with the present invention, it has been found that the assumption of a constant ringing signal is more closely matched if the following condition is met:

$$T_E*f=N$$

i.e., when the product of the echo spacing ($T_E$) in milliseconds and the operating frequency (f) for the CPMG spin echo train(s) is an integer number N.

In addition to the preferred method(s) described above, other alternative methods for performing the Ringing Estimation step can be used and include, but are not limited to:

(a) Using just a single PAP that incorporates the current primary CPMG;

(b) Using more than single Phase Alternate Pair CPMGs both preceding and following the current primary CPMG;

(c) Using one or more PAPs or other combinations of echo-trains that may or may not incorporate the primary current CPMG;

(d) Making intermediate ringing level estimates and then using other filters, or means of characterization, to determine the final estimated ringing level;

(e) Making intermediate ringing level estimates and then characterizing any depth-dependent behavior of the ringing level estimates to determine the final estimated ringing level.

Using the principles of this invention outlined above, computation of the Ringing Estimates using the above alternative methods can be derived by persons of average skill in the art, and will not be considered in further detail. Other methods or variations of the Ringing Estimate processing step will be apparent to those skilled in the art and are intended to be used, where applicable.

B. Ringing Elimination

In accordance with the present invention, the estimated level of ringing (a single number or slowly varying function) obtained in the previous step and described in Section A above is next removed in the step of Ringing Elimination from the current CPMG echo-train measurement. This ringing elimination is accomplished in accordance with a preferred embodiment by subtracting the estimated ringing from each and every echo of the current measurement CPMG echo train, as expressed below:

$$CPMG_0'(n)=CPMG_0(n)-\text{MeanRingingAverage} \qquad \text{Eqn. (12)}$$

Again, since the CPMG echo train and the estimated ringing have both a real and imaginary component, the ringing elimination is performed for both the real and imaginary channels.

C. Experiment Stacking

Experiment stacking is used in accordance with the present invention in order to improve the signal-to-noise ratio (SNR) to an adequate level. It should be noted that for multi-frequency tools, such as the MRIL® Prime tool, this step means that the experiment stacking is performed across one or more frequencies depending on how the data was acquired.

Experiment stacking is employed in accordance with the present invention in two embodiments. In a first embodiment, the method uses a boxcar running average filter, whose length depends primarily on the desired signal-to-noise. It will be appreciated by those of skill in the art, that using filters with no other length constraints is a distinct improvement over the prior art, where the filter length is calculated as a multiple of the number of frequencies and phase alternate pairs (PAPs). Therefore, where the data dictates it, in accordance with the present invention on can use a boxcar filter of length 10, whereas in prior art stacking one would have to use a filter of length 16, which introduces processing delays and may lead to decreased vertical resolution of the data.

In a preferred second embodiment, instead of using a boxcar filter for the Experiment Stacking step other types of filters can be used advantageously and may be more appropriate for achieving the desired signal-to-noise ratio. For example, the filters described below in Section D provide an alternative to boxcar filtering to improve the vertical resolution of NMR logs such as those obtained by the MRIL® tool.

In accordance with a preferred embodiment, all three steps discussed in Sections A, B and C above can be performed as a single pass through the acquired data, CPMG by CPMG, typically in a successive or chronological fashion. In an alternative embodiment, the first two steps can be performed in a single pass through the acquired data in a successive fashion, with the third step performed as a second pass.

Post-Processing

After Experiment Stacking, which in accordance with this invention is the last pre-processing step, stacked CPMG echo trains can be treated in the same fashion as the stacked CPMG echo trains that result from prior art methods: for example, the stacked echo-trains could be "phase-rotated", and then "inverted in the $T_2$ domain" to obtain the "$T_2$ spectrum" of the echoes, as known in the art. The interested reader is directed to the disclosure of U.S. Pat. No. 5,517,115, as well as U.S. Pat. Nos. 5,212,447; 5,280,243; 5,309,098; 5,412,320; 5,557,200 and 5,696,448 for a detailed description of these methods.

Proposed Method: Special Case

The proposed method can, optionally, be altered in those circumstances in which the Experiment Stacking requires stacking echo-trains across PAPs. In this case, the Ringing Estimation and Ringing Elimination steps can be accomplished by taking the PAP differences—as is done in the current method—and then applying the appropriate type of Experiment Stacking. This approach is further addressed in Section D below.

EXAMPLES

FIG. 4 shows graphically the results of the first and second processing steps discussed above. For all plots, the x-axis is the echo time and the y-axis is the echo or ringing amplitude, the real channel echo amplitudes are shown in red and the imaginary channel amplitudes are shown in green. (color drawings attached, as well as black and white).

The first column, with three plots, shows the input primary phase CPMG echo train ($CPMG_0$) in the middle plot. The input alternate phase CPMG echo train following the primary phase ($CPMG_{+1}$) is shown in the upper plot and the input alternate phase CPMG echo train preceding the primary phase ($CPMG_{-1}$) is shown in the lower plot.

The second column with two plots shows the intermediate estimated ringing level results from Step 1a: $Ringing_{+1}$ in the upper plot and $Ringing_{-1}$ in the lower plot. In addition the intermediate estimated ringing level results are shown as the horizontal lines in the respective plots: MeanRinging+1 in the upper plot and $MeanRinging_{-1}$ in the lower plot; with the magenta line representing the real component and the cyan line representing the imaginary component.

The third column plot shows the end of the ringing removal step for the current primary phase CPMG echo train where the final estimated ringing levels (MeanRingingAverage) from the Ringing Estimation step have been removed from the input primary phase CPMG echo train.

FIG. 5 shows the effects of different levels of experiment stacking as would be applied in the Experiment Stacking step. For each plot one track (in red color) shows the real channel and the other track (in green color) shows the imaginary channel.

The plot at the top of the first column is identical to the last plot in FIG. 4. The middle and bottom plots of the first column show that the method of this invention provides almost identical results as the prior art method does when the same amount of experiment stacking (16 levels) is used.

The second column shows how the signal-to-noise of the resulting CPMG echo trains improves with increased amounts of experiment stacking.

FIGS. 6 through 10 show how different amounts of experiment stacking impact the vertical resolution of a section of log data. In particular, Track 1 shows a Density Porosity curve in black—computed from a Bulk Density log assuming grain and fluid densities of 2.65 and 1.0 gm/cc respectively—the MRIL Effective porosity (MPHI) in magenta and MRIL Bulk Volume Irreducible (MBVI) in red. Track 2 shows the $T_2$ distribution resulting from the MAP inversion algorithm.

The illustrative examples show that vertical resolution improves as the level of experiment stacking decreases with a corresponding trade-off of reduced accuracy of the inversion results. The accuracy reduction can be acceptable to a point the user is comfortable with, which then sets the acceptable vertical resolution for any particular data set.

An alternative embodiment of the invention uses a modified sequence to acquire multiple echoes (on the order of 10). The readout sequence may be identical to a short CPMG sequence with the shortest possible echo spacing (about 0.5 ms). This sequence is affected by two magneto-acoustic ringing phenomena:

(1) Ringing that is generated by every $\pi$ pulse, which affects every echo, because there is only a short time delay, of the order of a few microseconds to a hundred or so microseconds, between a $\pi$ pulse and an echo acquisition. Phase alternation can cancel this type of ringing with about 90% to about 99% efficiency.

(2) Ringing generated by the $\pi/2$ pulse extends through the following $\pi$ pulse and impacts mostly the first echo. It is phase-coherent with the $\pi/2$ pulse and therefore cannot be cancelled by phase alternation. Rather, we employ frequency dithering, which is, for instance, described in the U.S. Pat. No. 6,204,663, assigned to the assignee of the present application. In frequency dithering, the sequence is repeated on a slightly different frequency to achieve a phase difference between $\pi/2$-ringing and NMR signal. In particular, at an echo spacing of about 0.5 ms, a frequency step of 1 kHz achieves an about 180-degree phase rotation in the ringing signal. By co-adding the results, the ringing component is eliminated with cancellation efficiencies ranging from about 50% to about 95%.

The U.S. Pat. No. 6,204,663 B1, incorporated herein by reference in its entirety for all purposes, issued on Mar. 20, 2001 and assigned to the assignee of the present application describes a preferred frequency alternating approach (also termed frequency dithering) for ringing correction. This approach is described next by way of further illustrating the present invention.

With a standard pulse sequence typically employed by NMR logging tools, such as the Numar MRIL® and the Schlumberger CMR tools, an excitation pulse ($E_x$) with radio frequency (r.f.) phase of zero degrees is first applied followed by refocusing pulses with a phase of positive ninety (90) degrees relative to the $E_x$ pulse with a wait time of $\tau$(tau) between the excitation pulse and the first refocusing pulse, and between the refocusing pulses ($R_{-y}$) and the acquisition windows (A) to enable measuring of the following echo train. The phase-alternated version of pulses is identical to the above described sequence, except that the refocusing pulses ($R_{-y}$) are 180 degrees out of phase, i.e., at a phase angle of minus ninety (90) degrees with respect to the $E_x$ pulse.

When the complex-valued NMR measurements acquired according to the standard and phase-alternated, preferably CPMG, pulse sequences are added, the NMR signal is enhanced, and the interference arising from imperfect refocusing pulses is reduced. However interference associated with the excitation pulse requires more to correct self-resonances within the measurement bandwidth but not phase-locked to the NMR signal. These signals evolve with their intrinsic self-resonant frequency and exhibit a phase difference from the NMR signal that depends on the particular self-resonant frequency and the time delay between excitation and data acquisition. Typically, more than one self-resonance are located within the measurement bandwidth with their number and exact frequencies generally unknown while being time-dependent.

Application of pulse sequences corresponding to two or more frequencies with alternation between at least two closely spaced NMR frequencies excites the same self-resonance. Since, the phase difference between interference and NMR signal evolves differently between excitation and data acquisition for the two frequencies, for instance, if the frequency change is made equal to one-half of the time between excitation pulse and acquisition, an additional phase difference of 180 degrees is obtained between the two echo trains at the two frequencies that is useful in canceling the self-resonance associated ringing due to the first $E_x$ pulse.

An example cycle of pulse sequences in accordance with a preferred embodiment of the present invention is shown in FIG. 25. The second and fourth pulse sequences are applied at a different frequency from the first and third pulse sequences. Acquisition windows $A_{ij}$ correspond to the ith echo in the jth pulse sequence. In the preferred embodiment, the frequency difference is a function of the time delay between excitation pulse and data acquisition:

$$|F_1 - F_2| = \frac{1}{4\tau}$$

where $F_1$ is the frequency at which the first and third pulse sequences are applied, $F_2$ is the frequency at which the second and fourth pulse sequences are applied, and $\tau$ is the constant delay time both between the excitation pulse and the first refocusing pulse and between the refocusing pulses and the acquisition windows.

In a more general case, the frequency difference can be expressed as:

$$|F_1 - F_2| = \left(n + \frac{1}{2}\right)\frac{1}{2\tau},$$

wherein 'n' is any integer or zero. It will be appreciated that for n=0 the two frequency difference expressions are identical. The more generic expression further indicates that due to the cyclic nature of the problem, a frequency difference corresponding to an additional offset of n/(2τ) will work as well. Since keeping the frequency difference relatively small is desirable, however, it should be clear that the case in which n=0 is preferred. However, for making simultaneous measurements it is desirable to evaluate different cylindrical volumes, and a larger frequency difference provides sufficient resolution to avoid overlaps.

Further, in accordance with a preferred embodiment of the present invention, data from all four measurements shown in FIG. 25 is added, which amplifies the NMR response and cancels both excitation and refocusing interference. In particular, data corresponding to the same acquisition slots are averaged using complex arithmetic:

$A_1=1/4(A_{11}+A_{12}+A_{13}+A_{14})$, $A_2=1/4(A_{21}+A_{22}+A_{23}+A_{24})$, $A_3=1/4(A_{31}+A_{32}+A_{33}+A_{34})$, ... etc. ..., where averaged acquisition $A_k$ corresponds to the kth slot in each pulse sequence. The generalization indicates that this method can be used for an unlimited string of acquisition slots and is not limited to four (4) slots shown in FIG. 25. Preferably, the refocusing pulses and corresponding acquisitions are repeated for the full length of the pulse sequence. Thus, averaged acquisitions $A_k$ may be obtained for all acquisition slots k.

To summarize, in an embodiment of the invention each step in the saturation-recovery sequence is preferably repeated three times: phase-alternated, frequency-alternated and phase- and frequency alternated.

However, in the presence of very high ringing amplitudes (about 100%–200% of full scale NMR signals), the residuals from phase- and frequency-alternation are still strong enough to affect the final result. A 200% ringing signal, cancelled with about 98% efficiency, can result in a +/−4 p.u. (porosity unit) error in the final result, the error being random due to the randomness of ringing phase v. NMR signal phase.

Therefore, measuring both the efficiency of the ringing cancellation and the amplitude and phase (i.e sign) of the ringing residual with respect to the NMR signal can both serve as a quality control indicator and/or can lead to corrective measures that are applied to the final result.

Figure 26:
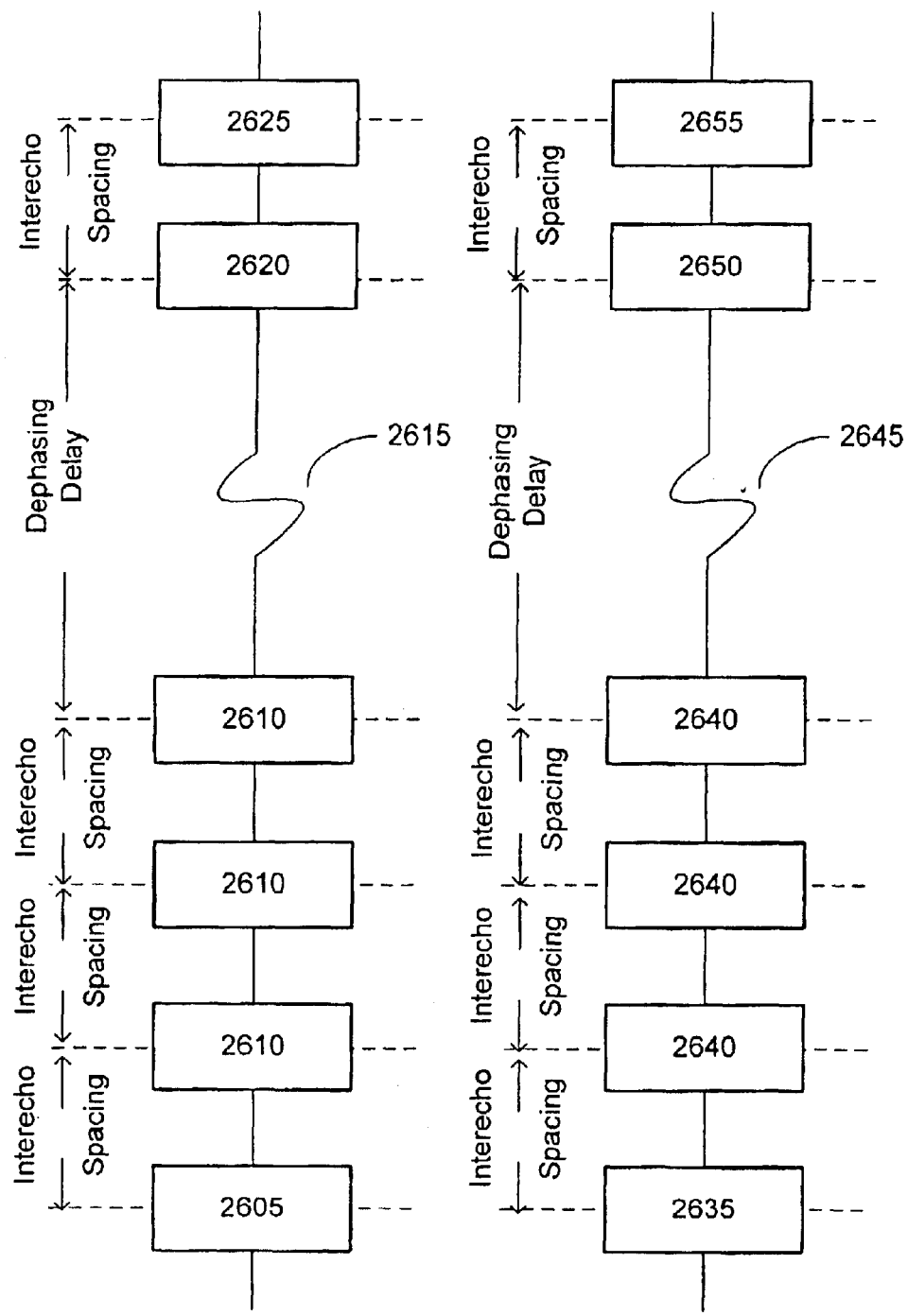
FIG. 26 illustrates example pulse sequences in accordance with a preferred embodiment of the present invention for also evaluating the residual ringing signal by introducing a dephasing delay in the pulse sequence.

A modified read-out sequence that acquires two special data points that are indicative of ringing allows such a measurement. An example, illustrated in FIG. 26, is given by:

(broadband saturation)-$T_{sr}$-$(\pi/2)_X$-[$\tau$-$(\pi)_Y$-$\tau$-echo]-$(N+1/2)\tau$-$(\pi/2)_x$-$2\tau$-$acq_x$-$\tau$-$(\pi)_y$-$\tau$-$acq_y$ where $T_{sr}$ is saturation-recovery time. Typically ranges from 1 ms to several seconds.

$(\pi/2)_X$ is the excitation pulse in the read-out phase.

$\tau$ is the CPMG time delay equal to ½ of the echo-to-echo delay $T_E$. Typically τ=0.25 ms.

$(\pi)_Y$ is the refocusing pulse in the read-out phase.

echo is the acquisition of CPMG pulse echo.

[ . . . ] denotes repeating the indicated pulses, measurements, or delays in the square brackets.

$(N+1/2)\tau$ is the delay designed to sidestep the pulse pattern set up by the CPMG sequence by introducing a non-recoverable phase error in the NMR signal.

N=0, 1, . . . . It is recommended that N is at least 5.

$(\pi/2)_x$ is a test excitation pulse.

$acq_x$ represents acquisition of ringing-only data, consisting of $(\pi/2)$ ringing.

$(\pi)_y$ is a test refocusing pulse.

$Acq_y$ denotes acquisition of ringing-only data, consisting of $(\pi)$ ringing.

This sequence is repeated for phase-alternation, that is, the phases of the (π) pulses are changed to −y. Next, the sequence is repeated on the alternate frequency for first-echo ringing cancellation and phase-alternated there as well. Note that the test data "$acq_x$" and "$acq_y$" undergo the same ringing cancellation scheme. Thus, the described example sequence does not merely gauge the amount of primary ringing, but rather also measures separately (π/2) and (π) ringing components, both amplitude and phase for each uncanceled component, that remain uncanceled.

In FIG. 26 two NMR pulse sequences are shown without the echos that are generated in response to each pulse. The first NMR pulse sequence comprises read-out excitation pulse 2605 followed by an interecho spacing and one or more read-out rephasing pulses 2610. Then, a dephasing delay 2615 is followed by test excitation pulse 2620 and test rephasing pulse 2625. The second NMR sequence is similar with corresponding read-out and test pulses. The echos generated by the first and the second NMR sequences are combined to cancel out ringing due to the rephasing pulses by inverting the phase of the second NMR sequence relative to the first NMR sequence. Ringing due to the first excitation pulse is canceled by making the frequency of the second NMR pulse slightly different from the frequency of the first NMR sequence. It should be noted that a second NMR pulse need not have both its phase and frequency adjusted relative to the first NMR pulse sequence. Instead, FIG. 26 is illustrative of possible NMR pulse sequences, and there may be variable saturation recovery times and broadband saturation pulses in addition to the illustrated elements.

In view of this information, it is then possible to (1) produce a quality-control log that shows the potential influence of residual ringing on the final log data; (2) correct the accumulated echo amplitudes (separately for the first echo and for echoes 2, 3,) after phase-cycling and frequency-cycling; (3) estimate the phase between NMR signal and residual ringing; (4) estimate the error in the final answer due to ringing and, optionally, add or subtract a correction value; and (5) do nothing, i.e. do not apply a correction, for instance, because amplitude corrections always introduce a certain amount of extraneous noise because the ringing estimation itself is noisy. Therefore, if the residual ringing can be regarded as negligible, then not doing anything is a good choice as well.

Unlike the teaching of the U.S. Pat. No. 6,121,774, issued Sep. 19, 2000 to Boqin Sun and Reza Taherian, the above described approach does not require, in eliminating ringing while measuring a nuclear magnetic resonance property of earth formations, canceling the spin-echoes followed by correcting the signals to eliminate the ringing component.

Rather than "cancel" spin-echoes the pulse-echo is side stepped by introducing a $(N+1/2)\tau$ delay described previously that moves the data acquisition windows away from where spin echoes, indirect echoes or rotary echoes may occur. Moreover, the primary echoes are corrected by applying a "ringing correction" that goes beyond estimating the ringing contribution by making the ringing correction automatic. Thus, ringing contributions are reduced by a combination of phase-alternation and frequency-alternation. Instead of ringing, the described method and system of the invention estimate the residual ringing component(s) remaining so that a decision, which may also be automated, may be made to apply or not apply various corrections after all other compensation steps (phase and frequency alternation).

Signal Processing for Detection of Diffusion and Various Phases

The method for fluid detection in accordance with a preferred embodiment of the present invention assumes data acquisition in the presence of a static magnetic field gradient in the range 10–30 G/cm, although in many embodiments of the invention significantly lower gradients may be employed with better detection and processing. The method further requires at least two separate measurements with different saturation-recovery times $T_{Ri}$ and/or different echo-to-echo spacings, and is implemented using the data acquisition sequence illustrated in FIG. 27. In addition, the very low signal-to-noise (SNR) levels which are due to HI losses and incomplete magnetization recovery in a typical NMR measurement necessitate signal detection using two-channel complex data stream. Therefore, in a preferred embodiment of the present invention data is acquired in two orthogonal channels, and averaged over a vertical logging interval to increase the SNR for the acquired measurement data.

Figure 30:
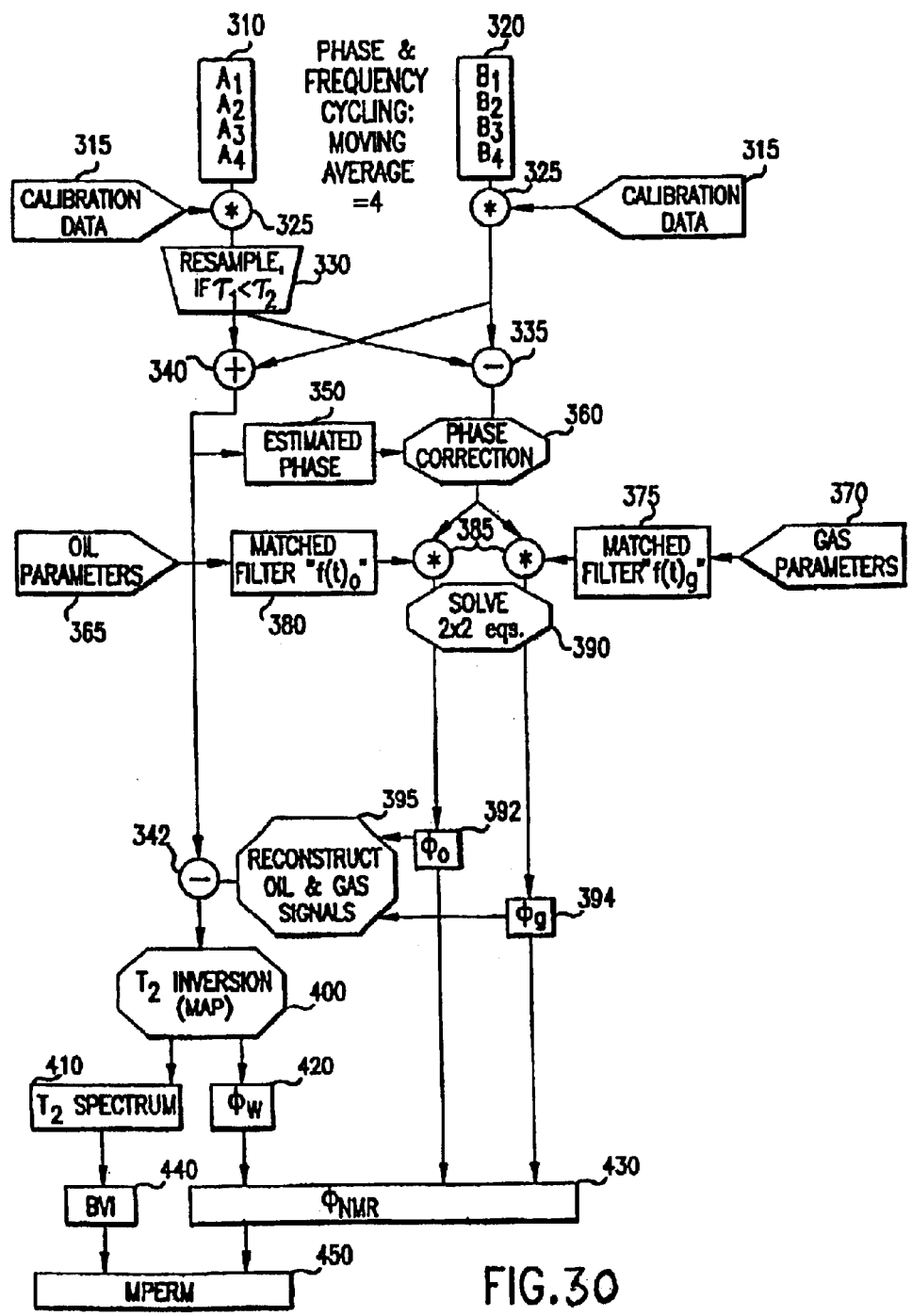
FIG. 30 is a flow diagram of the data processing method in accordance with a preferred embodiment of the present invention.

Turning next to FIG. 30, it shows in semi-block diagram form the signal processing method in accordance with a preferred embodiment of the present invention. Specifically, the determination of water, oil and gas saturations in the sensitive volume begins by performing at least two interleaved $T_1$-weighted measurements to separate the wetting phase (brine, surface-dominated relaxation) from the non-wetting phase (light hydrocarbons, bulk-dominated relaxation). Optionally, these measurements can be diffusion-weighted as well. As shown in FIG. 30, this results in two parallel data sets of complex time-domain data. Data sequence 310 generally corresponds to data obtained from the long recovery time $T_{R2}$ while data sequence 320 corresponds to data obtained from the short recovery time $T_{R1}$. Between about 150 and 300 data points are used in each sequence. Preferably, the recovery times used are about 2 sec for $T_{R1}$ and about 8 sec for $T_{R2}$. Pairs of echo trains are formed by matching overlapping short and long TR intervals thereby minimizing the systematic variations introduced when formation bed boundaries are crossed.

Figure 31A:
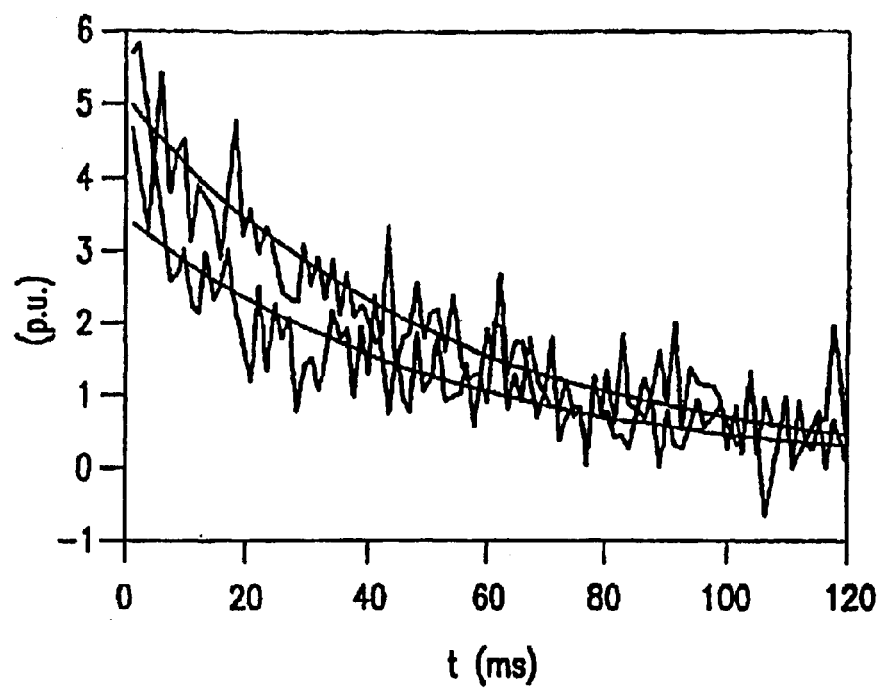
FIG. 31A illustrates the difference between two signals with different recovery times $T_{Ri}$.

Following the data acquisition process, in block 325 the two data sets are corrected using calibration data from blocks 315. Specifically, such calibration data is obtained from samples at room temperature, with 100% water saturation, for example in a water-filled tank. FIG. 31A shows two such calibrated data sequences as functions of time. As shown in FIG. 31A, the magnitude values for the measurement signals are conveniently calibrated in porosity units (p.u.). Skipping for a moment block 330, next the complex difference between the signals in each data pair is obtained in subtractor 335 to eliminate the brine contribution; the sum signal is obtained in adder 340 to estimate the input signal phase and phase-correct the difference signal in block 335 accordingly. Specifically, it has been observed that while the absolute phase of the NMR signal is subject to slow variations due to hole and tool conditions, it shows excellent short-term stability. Therefore, the phases of the sum and the difference signals are approximately equal. In accordance with the present invention this feature is used to correct the phase of the difference signal on the basis of a phase estimate for the sum signal which was found to be comparatively more accurate.

In particular, a depth-averaged signal phase is computed in block 350 from the complex sum signal. If proper frequency and phase cycling has been employed during data acquisition, all sum and difference echoes have the same average phase. The phase estimated in block 350 is used to rotate, in phase correction block 360, the phase of all data points in the complex difference signal into the real axis. Such rotation yields the true absorption mode (real-valued) signal component. The dispersion signal component (imaginary valued) can be discarded.

Based on the parametric representations for relaxation times and diffusion characteristics of the non-wetting hydrocarbon phases which are computed, as indicated in the section "Signal Modeling and Corrections", and stored in block 365 for the oil and block 370 for the gas components. Matched filters representing the liquid and the gaseous phases are computed next in blocks 375, 380 in the echo-time domain, using the expressions:

$$f(t)_o = [\exp(-TR_1/T_{1,o}) - \exp(-TR_2/T_{1,o})]\exp(-t/T_{2,o}) \quad (13a)$$

$$f(t)_g = HI_g[\exp(-TR_1/T_{1,o}) - \exp(-TR_2/T_{1,o})]\exp(-t/T_{2,o}\dagger) \quad (13b)$$

where all used parameters have been pre-computed.

In general, the filter functions in Eqs. (13a–13b) are not orthogonal and cannot be directly applied to the data. (See FIG. 32A) Instead, the amplitude responses to these filters are extracted from the phase-corrected difference signal d(t) by solving, in block 390, the overdetermined equation system, $$Ax=d(t), A=[f(t)_o^T f(t)_g^T] \qquad (14)$$

in a least-squares sense. The solution is found by solving the following 2×2 equation system for the amplitude vector x:

$$(A^T A)x = A^T d(t), \qquad (15)$$

If the difference signal d(t) was properly scaled in p.u., the first element of the solution vector x is oil-filled porosity $\phi_o$, obtained in block 392, and the second is gas-filled porosity $\phi_g$ (block 394). Calculating backwards from these numbers, the properly scaled oil and gas signatures can be reconstructed in block 395, and subtracted from the complex sum signal in block 342. The remainder is the signal originating from brine, which, as wetting phase, is sensitive to the surface-to-volume ratios in the remaining pore space available to water.

In block 400, a $T_2$ inversion mapping is constructed, as discussed, for example in the Prammer et al. paper above. The results are used, in block 410, to estimate the $T_2$ spectrum of the signal and in block 420 to estimate the water-bound porosity.

These ratios are indicative of the non-producible water volume held in place by capillary forces (BVI), which is computed in block 440. On the other hand, the total area under the $T_2$ curve is interpreted as water-filled porosity $\phi_W$, which is computed in block 420. The total NMR porosity can be computed in block 430 using the expression:

$$\phi_{NMR} = \phi_W + \phi_o + \phi_g \qquad (16)$$

The free-fluid index as seen from the water phase is augmented by oil and gas porosity:

$$FFI = FFI_W + \phi_o + \phi_g \qquad (17)$$

From $\phi_{NMR}$, BVI and FFI, a permeability estimate can be calculated in block 450, which depends only on NMR-derived quantities.

Processing of Diffusion-weighted Data.

Turning back to block 330 in FIG. 30, for a diffusion-weighted measurement a complication arises from the different sampling grids employed in acquiring the data sets, which make up a data pair. In this case, data from the shorter echo spacing is mapped onto the wider sampling grid by linear interpolation between complex echoes. Diffusion-weighting is taken into account to give the following matched-filters expressions:

$$f(t)_o = [\exp(-TR_1/T_{1,o}) - \exp(-TR_2/T_{1,o})]\exp(-t/T_{2,o}), \qquad (18a)$$

$$f(t)_g = HI_g[1-\exp(-TR_2/T_{1,g})]\exp(-t/T_{2,g}^\dagger) - HI_g[1-\exp(-TR_1/T_{1,g})] \\ \exp(-t/T_{2,g}^{554}(T_2/T_1)^2) \qquad (18b)$$

The diffusion-weighted data is next processed following the flow graph in FIG. 30. The combined $T_1$-weighted and diffusion-weighted measurement is advantageously used in cases where the gas filled porosity and HI are relatively low, and correspondingly the SNR of the measurement is relatively low.

Error estimates for $T_1$-weighted and diffusion-weighted data acquisitions in accordance with a preferred embodiment of the present invention can be obtained using the following considerations. The input data consists of two data sets, weighed by different recovery times and possibly sampled with different echo spacings. Each set is individually calibrated for HI=1.0. To compute the uncertainty of the parameter estimates, it is assumed that the noise in each data set is random and has Gaussian distribution with standard deviation σ=2. As indicated in locks 350 and 360 above, a depth-averaged signal phase is computed from the complex second echo in the sum. The estimated phase is used to rotate all complex differences into the real axis. Allowing for a small error in phase estimation, the noise component in the real-valued difference signal (dt) is approximately 1.5 p.u. Gas and oil porosities are given as least-squares solutions in block 390 in FIG. 30. Formally, the least-squares solution can be written as:

$$x_{(LSQ)} = (A^T A)^{-1} A^T d(t) \qquad (19)$$

Figure 33:
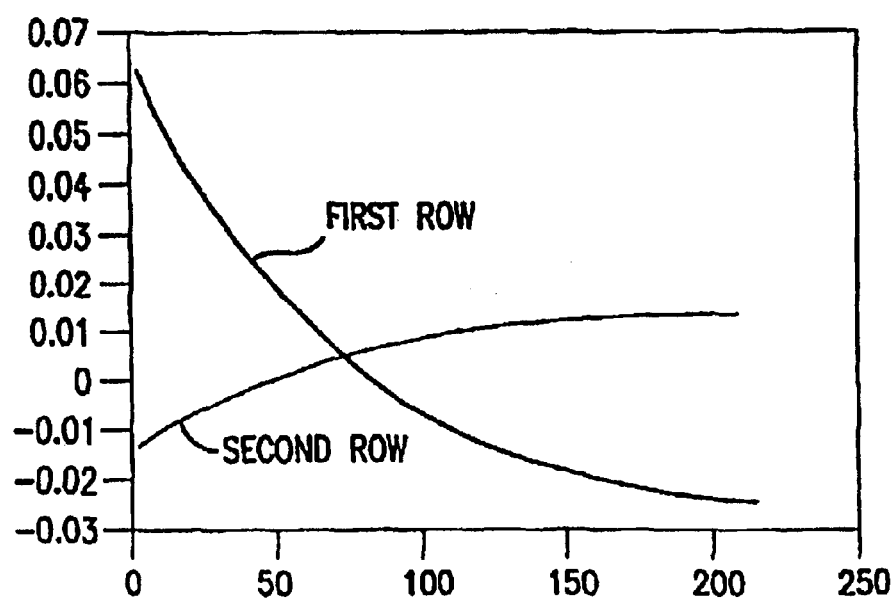
FIG. 33 shows orthogonalized filter functions of the gas and the oil matched filters in accordance with the present invention.

The sensitivity of the solution to random errors in the input is given by the condition number of the square, positive-definite matrix $A^T A$. The orthogonalized oil-sensitive filter function $f(t)'_o$ is the first row of the expression $(A^T A)^{-1} A^T$. The second row of this expression contains the orthogonal filter $f(t)'_g$, which is sensitive to the gas component. The orthogonal filter responses are shown in FIG. 33. Filter response functions are computed as follows:

$$\Phi_0 = \int_0^\infty d(t) f(t)'_0 dt$$

$$\Phi_g = \int_0^\infty d(t) f(t)'_g dt$$

The average output uncertainty was determined by Monte Carlo simulation. Using 100,000 samples, and assuming parameters, $HI_g=0.5$, $T_{1,g}=5$ s, the standard output deviation in the answer for gas filled porosity is ≈2.5 p.u. The uncertainty in oil-filled porosity is substantially reduced and is approximately equal to 1 p.u., dependent on $T_{1,o}$.

For the reader's convenience, a list of all notations used in the description above is given next.

| Nomenclature |
| --- |
| A = design matrix for least-squares problem |
| $A^T$ = transpose matrix of A |
| BVI = bulk volume irreducible water, p.u. |
| D = restricted diffusivity, cm$^2$/S |
| $D_O$ = unrestricted diffusivity, cm$^2$/S |
| d(t) = difference function |
| f(t) = filter function |
| FFI = free fluid index, p.u. |
| G = magnetic field gradient, G/cm |
| HI = hydrogen index, relative to water |
| MPHI = apparent NMR porosity, p.u. |
| T = absolute temperature, ° K. |
| $T_1$ = longitudinal relaxation time, s |
| $T_1^\dagger$ = pseudo transverse relaxation time, s |
| $T_2$ = transverse relaxation time, s |
| $T_2^\dagger$ = apparent transverse relaxation time, s |
| TE = CPMG echo-to-echo delay (TE = 2τ), s |
| TR = recovery time, s |
| x = solution vector to least-squares problem |
| φ = porosity, p.u. |
| $\phi_{NMR}$ = corrected NMR porosity, p.u. |
| $\phi_n$ = CPMG phase, n = 1 or 2 |
| γ = gyromagnetic ratio, ratio, rad$^{-1}$ G$^{-1}$ |
| {character pullout} = density, g/cm$^3$ |
| ρ = standard deviation |
| τ = CPMG pulse-to-echo delay (τ = TE/2), s |
| $\tau_{eff}$ = diffusion-effective CPMG delay, s |

Subscripts
g = gas
o = oil

The following figures serve to provide better understanding of different aspects of the invention with reference to signals obtained in different processing blocks in FIG. 30.

Figure 31B:
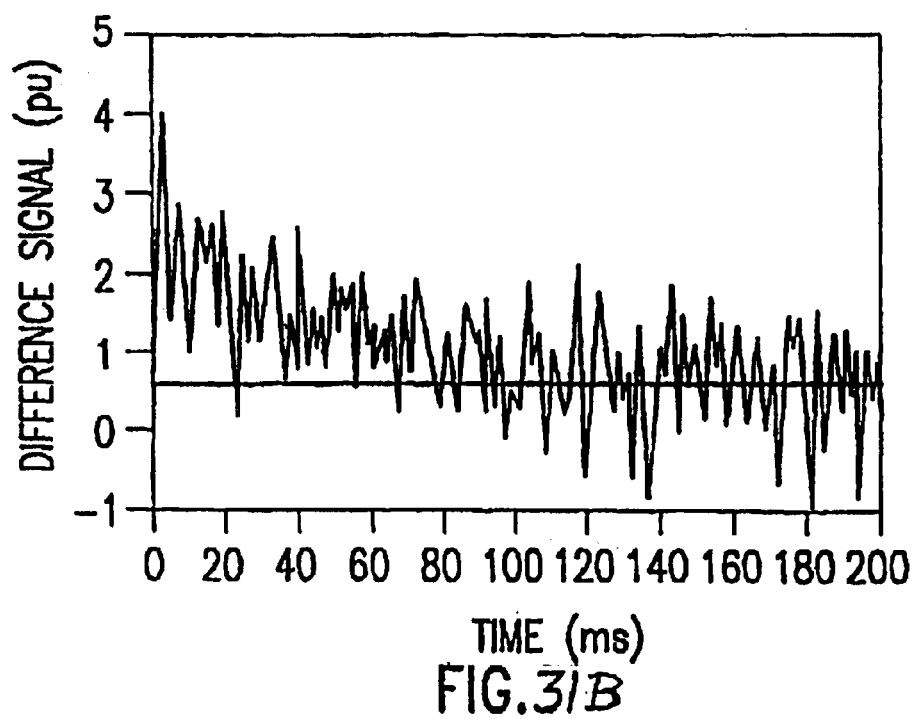
FIG. 31B shows a sample display of a difference data signal acquired at depth 15710 ft, as a function of time.
Figure 31C:
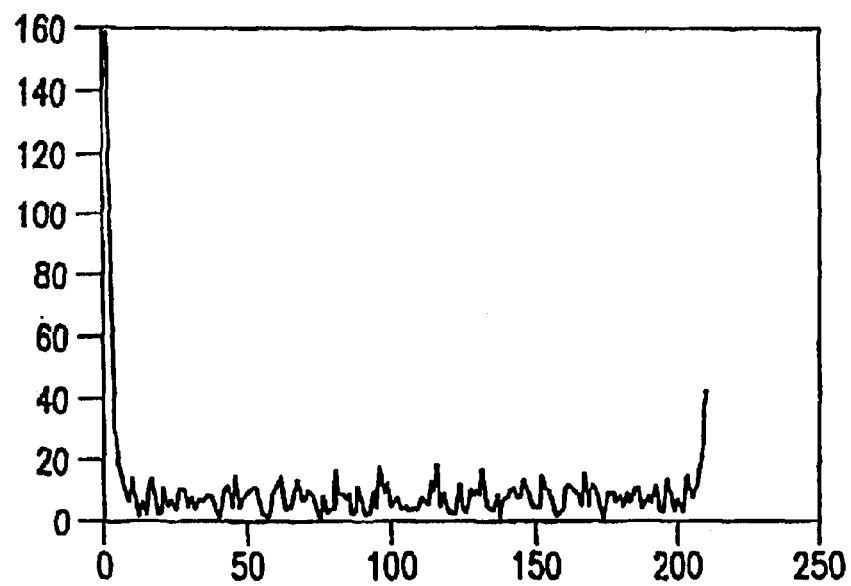
FIG. 31C is the magnitude of the Fourier transform of the signal shown in FIG. 32B.

In particular, FIG. 31A illustrates the difference between two signals with different recovery times $TR_i$. FIG. 31B shows a sample display of a difference data signal obtained at depth 15710 ft, as a function of time. FIG. 31C is the magnitude of the Fourier transform of the signal shown in FIG. 31B.

Figure 32A:
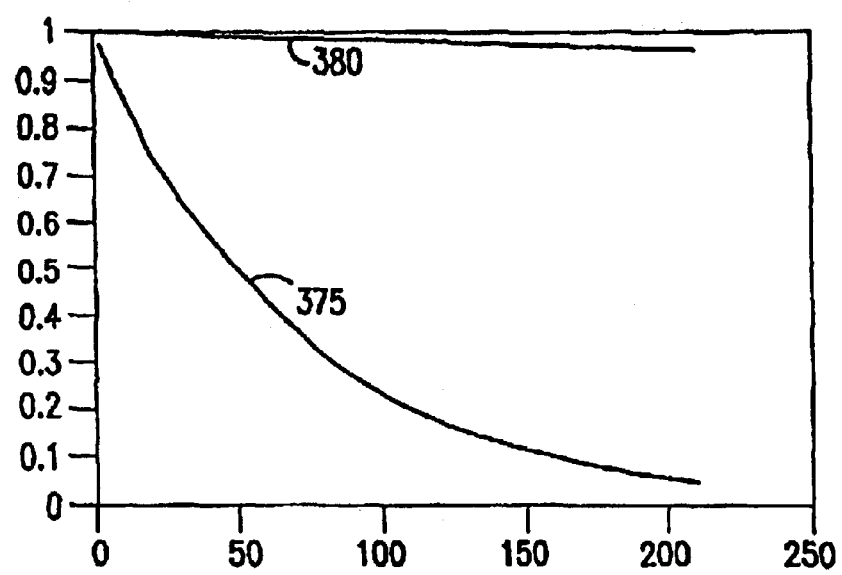
FIG. 32A shows sample response of the gas and the oil matched filters in accordance with the present invention.
Figure 32B:
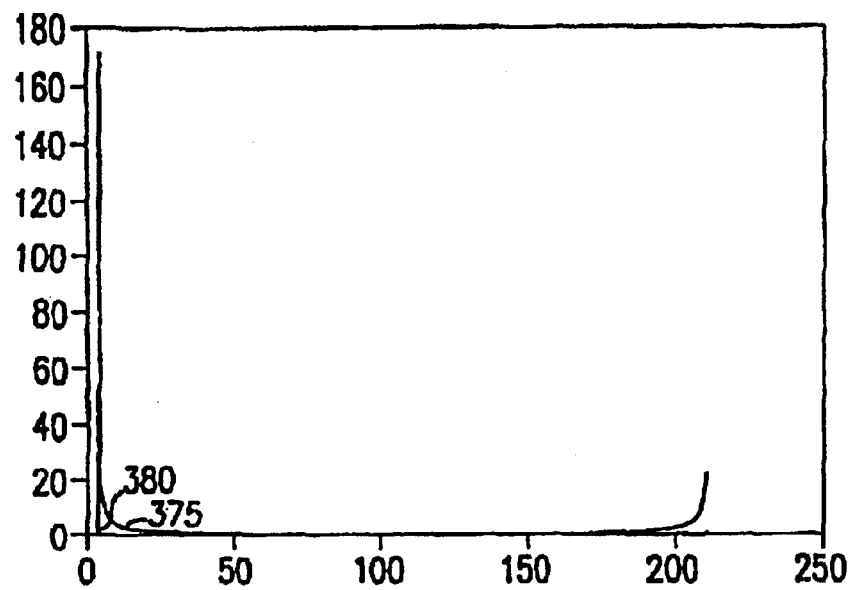
FIG. 32B is the magnitude of the Fourier transform of the matched filter responses shown in FIG. 32A.

FIG. 32A shows the response of the gas (block 375) and the oil (block 380) matched filters in accordance with the present invention; FIG. 32B illustrates the magnitude of the Fourier transform of the matched filters responses shown in FIG. 32A.

FIG. 33 shows the orthogonalized filter functions of the gas and the oil matched filters in accordance with the present invention.

Results

Logging tests were performed in single-frequency and dual frequency operating modes to assess the amount of vertical and lateral motion, which could affect the accuracy of the $T_1$-weighted measurements conducted in accordance with the present invention. A similar operating procedure was already in place to set the optimum delay time between measurements in the pay zone. Data acquired under a variety of hole conditions and $T_1$ values were examined; logging speeds in this particular mode were typically 300 ft/hr. In all cases, increasing the recovery time interval resulted either in a monotonic increase in NMR amplitude or in no increase. Sudden increases in amplitude at short recovery intervals, indicative of uncontrolled tool motion, were not observed.

The effect of invasion was studied by comparing results from wells drilled with water-base muds (WBM) and oil-muds (OBM). The WBM-drilled formations generally suffer high invasion and residual oil and gas saturations are low. Nevertheless, in many cases gas quantities above the detectability threshold are present, possibly due to backsaturation of gas into the invaded zone. As indicated above, another factor aiding the MRIL® is the 4" blind zone into the formation. OBM filtrate generally invades less and is therefore better suited for near-borehole saturation measurements. Oil filtrate mixes with the connate oil and replaces it to a certain extent. Because the filtrate has low viscosity, OBM aids the described hydrocarbon detection method by supplying a slowly relaxing component with known $T_1$. We recommend performing $T_1$ and $T_2$ measurements of filtrates in the laboratory at 1 MHz to assess the effect of OBM invasion.

The following example data was acquired in a deep (>10,000 ft), on-shore gas well, drilled with OBM. The gas parameters are summarized in Table 3.

TABLE 3 parameters for example data.

| | |
|---|---|
| gas temperature: | 100° C. |
| gas pressure: | 9000 psi |
| gas type: | $CH_4$ |
| $CH_4$ density: | $\rho = 0.26$ g/cm$^3$ |
| $CH_4$ hydrogen index: | $HI_g = 0.6$ |
| longitudinal relaxation time: | $T_1 = 6$s |
| unrestricted diffusivity: | $D_0 = 0.7 \times 10^{-3}$ cm$^2$/s |
| diffusion restriction (est.): | $D/D_0 = 0.8$ |
| magnetic field gradient: | $G = 18$ G/cm |
| effective pulse-echo spacing: | $\tau_{eff} = 0.65$ ms |
| apparent transverse relaxation: | $T_2^{\uparrow} = 60$ ms |
| $T_1/T_2^{\uparrow}$ contrast: | ~100 |

Figure 34:
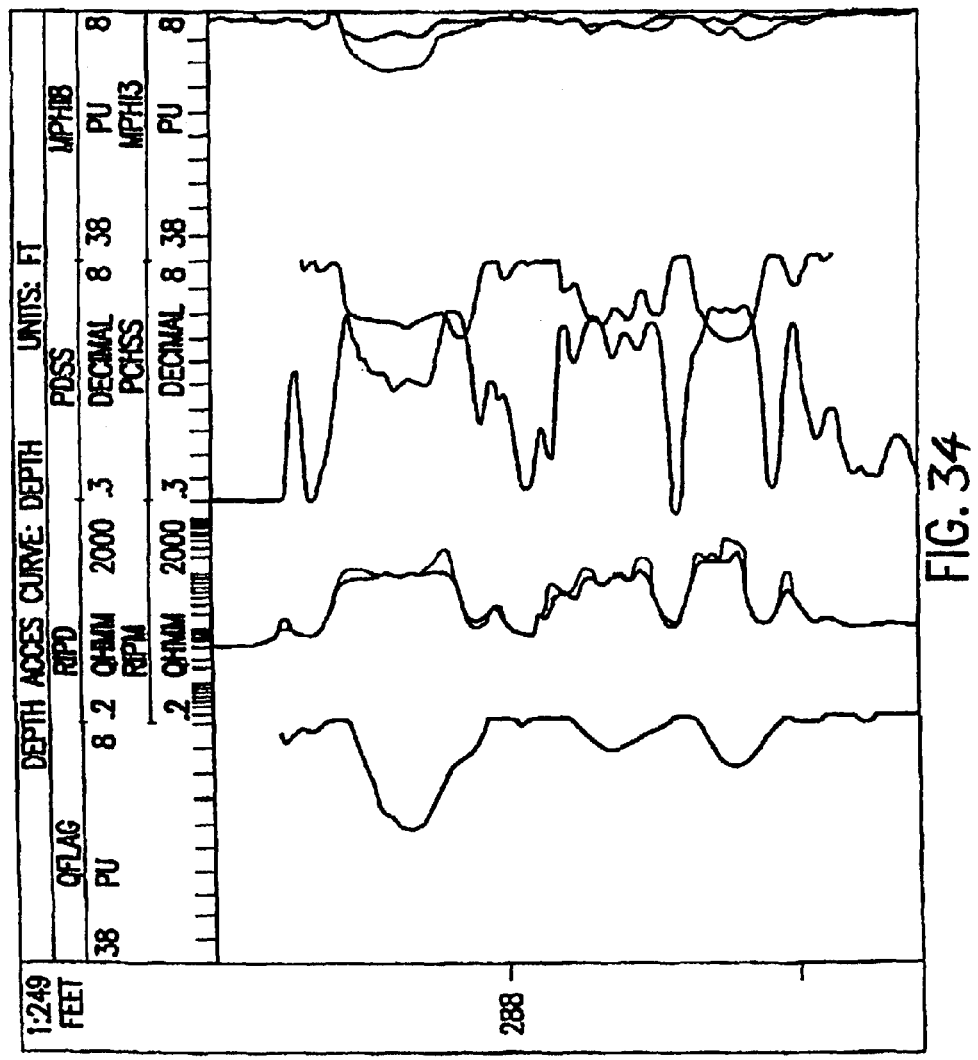
FIG. 34 shows logging data from an off-shore gas well at depth>10,000 ft.

Log results are shown in FIG. 34. For the example illustrated in FIG. 34 NMR data for recovery times of $TR_1=3$s and $TR_2=8$s were acquired in separate passes with a pulse-echo spacing $\tau=0.6$ ms. Both apparent NMR porosities are too low in the gas zone (shown in track 4). Complex echo sums and differences from these echo sets were computed. The sum had a constant phase of −2.1 rad, which was used to convert the difference signal to real-type values. Matched filters for the oil component:

$$HI_o=1.0, T_{1,o}=2000 \text{ ms}, T_{2,o}=100 \text{ ms};$$

and for the gas component:

$HI_g=0.6$, $T_{1,g}=6000$ ms, $T_{2,g}^{\dagger}=60$ ms; were computed and applied to the data in a least-squares sense as described above. The oil-filter response was essentially zero (not shown), the gas-filter response is plotted in track 1.

Gas-corrected NMR porosity indicates that mud filtrate did not invade the sampling diameter (15" at a probe temperature of 100° C.), or that gas did backsaturate into the invaded zone. In either case, the results clearly indicate the value of hydrocarbon saturation measurements near the borehole wall.

E. Alternatives to Box-Car Filtering

Yet another problem is improving the vertical resolution of the NMR data. Described below are approaches for improving the vertical resolution of NMR logs by replacing the box-car filter used in the prior art for removing both coherent and random noise signals, with a combination of two filters, in which the above functions are advantageously separated. A particular problem addressed below is that since in multi-frequency tools any two PAPs are separated by N CPMG pulse sequences, where N is the number of operating frequencies, the filter length used in the prior art has to be a multiple of 2*N. Due to this limitation, very long filters have to be used in the prior art, especially when the number N of operating frequencies is high. For example, there are N=8 operating frequencies that can be used in a MRIL® tool, so if full use is made of these frequencies, the minimum filter length is 16. Due to relatively low signal levels and the corresponding need for signal stacking, filter lengths of 64 are not uncommon.

D.1. Prior Art Filtering

The current processing practice involves the use of boxcar (BC) filters, which simultaneously perform phase alternated pair (PAP) stacking for coherent noise removal, and signal averaging for random noise reduction. The filter lengths used to this end are referred to as the Running Average (RA), and are multiples of the so called Minimum Running Average (MRA). As known in the art, the MRA depends on the type of the tool and its activation (i.e., dithered vs. non-dithered). The minimum filter lengths for the BC filters, for both MRIL-C and MRIL®-Prime tools are shown in the following Table 4.

TABLE 4

Minimum Running Averages (MRA) for MRIL-C, and MRIL-Prime Tools

| Tool | No. of Freq. | Dithering | MRA |
|---|---|---|---|
| MRIL-C | 2 | No | 4 |
| MRIL-C | 2 | Yes | 8 |
| MRIL-Prime | 8 | No | 16 |

In general, the filter length, or running average RA, is determined by $\sigma_n$, which is the standard deviation of the noise. The proper running average filter length is defined as $RA=n*MRA$ that results in $\sigma_n=1$, where n is an integer number. Although BC filters are efficient, primarily because of the simultaneous treatment of coherent and random noise components, and are easy to implement, there are four general problems associated with their use in practical applications.

First, in most high-gain environments (oil based mud, 8.5-inch hole, high frequency operation, etc.), the RA, that results in $\sigma_n$ of about 1, can be as low as 4. However, the actual running average used in such cases is typically larger due to the MRA condition. For example, consider a high-gain case, where RA=4 would be sufficient. The actual running average to be used, however, has to be 16 for the MRIL®-Prime tool, or 8 for a dual-frequency MRIL®-C tool (4 if the activation is not dithered).

Next, the constraint that the RA must be a multiple of MRA, results in a similar problem, particularly for tools such as the MRIL® Prime tool. For example, consider the case of a MRIL Prime measurement, where RA=24 would actually satisfy the $\sigma_n$ of about 1 condition. Since MRA is 16 for the MRIL® Prime tool, an RA value of 36 must be used instead of 24.

Further, the boxcar filter has an equal-weight distribution, which causes significant degradation of vertical resolution in those cases where a large number of CPMGs must be stacked for proper random noise cancellation. Consider, for example, a very highly conductive mud, where RA=48, and the sampling rate is 2 CPMGs per foot. In this case, a single point on the porosity log represents a formation volume thickness of 24 feet, and a bed near the edge of the sampled volume has equal weight in the porosity as a bed just at the mid-point.

Figure 12:
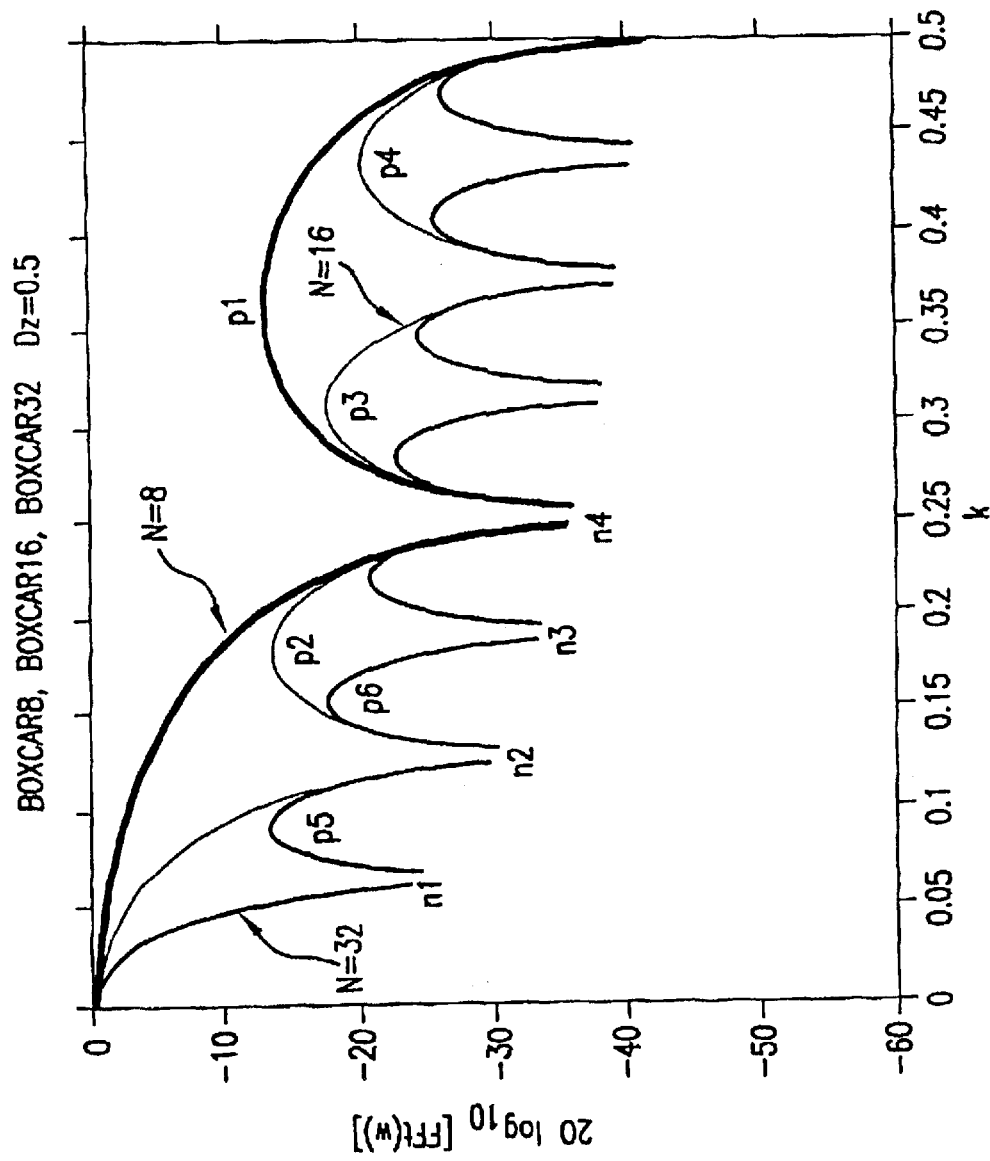
FIG. 12 illustrates the frequency response of several boxcar filters, which are used in the prior art methods.

Finally, the output of the boxcar filter is generally very noisy. The frequency response of several boxcar filters can be seen in FIG. 12. Notable in the figure is the presence of many notches in the frequency response, as well as the numerous secondary peaks. In practical applications these notches, in addition to the secondary peaks, cause oscillatory and noisy behavior. Further, one can note the secondary peaks, marked in FIG. 12 as p1 to p6. These peaks generate noise, since they are at or above −20 db level, which is considered the detection threshold for human eye.

D.2. An Alternative Approach

In accordance with the present invention an alternative approach is proposed that eliminates problems associated with the prior art. It is perceived that the main problem with the BC filter (in addition to its noisy behavior for large N) is its equal-weight distribution; as noted above, depending on the length of the filter local features may be lost. In accordance with the present invention it is proposed to use a tapered filter, such as the Hamming filter, which generally results in better preservation of the local features. Unfortunately, however a tapered filter alone cannot deal with the coherent noise components, due to the very nature of the MRIL data acquisition in multi-frequency mode. Thus, in accordance with the present invention removal of the coherent non-formation signals must be performed prior to the application of a tapered filter. The prior art discloses the use of PAPs to this end. The disclosure in Sections II.A/B and C this application illustrate other ways of removing this undesirable signal component.

In contrast to the simultaneous treatment of coherent and random noise by the boxcar approach, use of a tapered filter requires a two step approach, where PAPs-type processing to remove coherent noise signal components is followed by a tapered filter, as explained below.

Figure 13A:
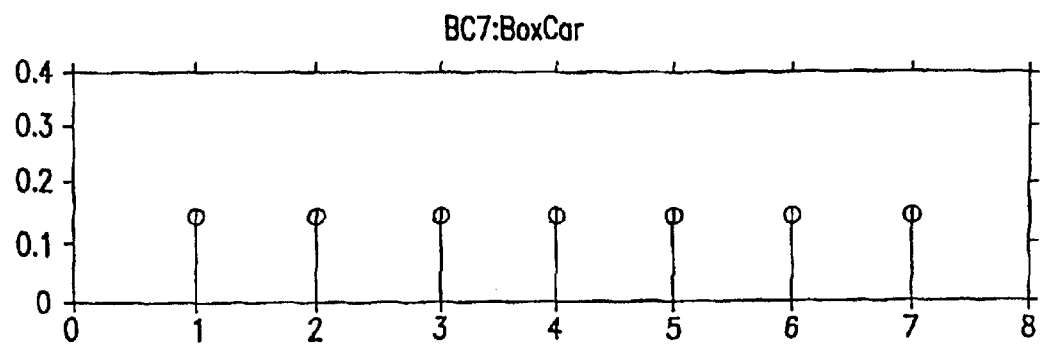
FIGS. 13A, 13B and 13C are plots of the filter coefficients of the box-car (A), Comb filter (B), and a Hamming filter (C)
Figure 13B:
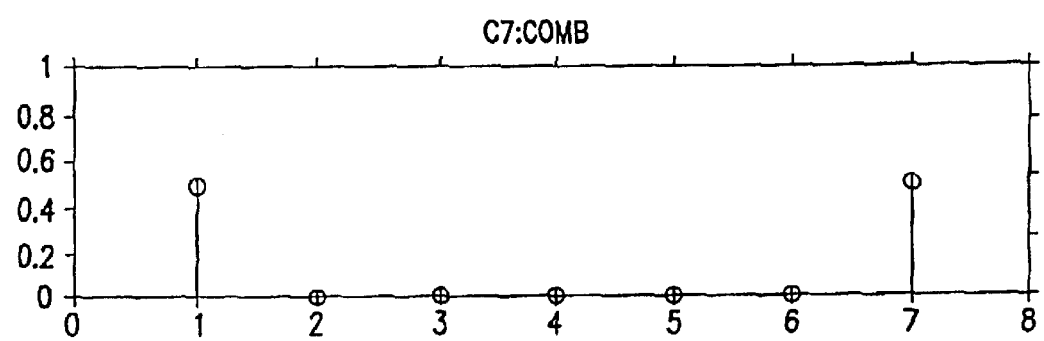

First, a Comb filter of length n (Cn) is applied to perform removal of the coherent noise components. A plot of the box-car and a Comb filter, for N=7, can be seen in FIGS. 13A and 13B. The filter lengths for the Comb filter depend on the tool and its activation type, and are listed in Table 5 below. Note that in this approach each CPMG sequence that belongs to a particular frequency is combined with its true phase alternated pair. CPMGs from other frequencies are not involved in this operation.

TABLE 5

Comb filter lengths for MRIL-C, and MRIL-Prime Tools

| Tool | No. of Freq. | Dithering | Length (n) |
| --- | --- | --- | --- |
| MRIL-C | 2 | No | 3 |
| MRIL-C | 2 | Yes | 5 |
| MRIL-Prime | 8 | No | 9 |

Figure 13C:
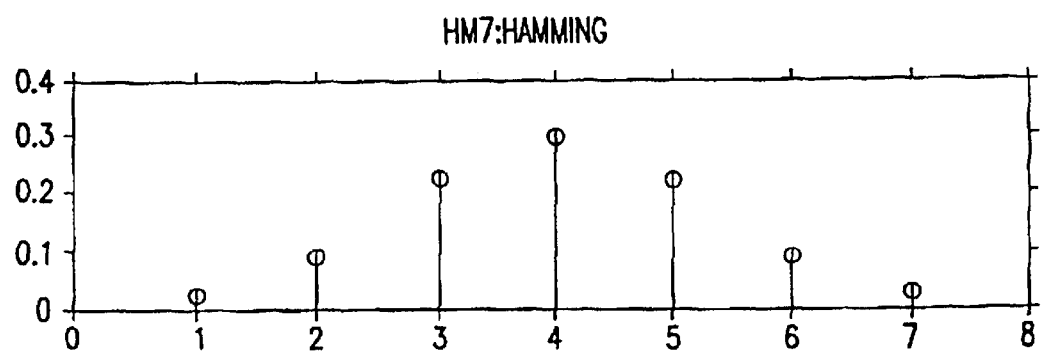

Secondly, a tapered filter of length n, such as a Hamming filter (HMn), is applied to the already phase alternated CPMGs, as shown in the illustrative examples below. This operation preserves more of the local information, while reducing random noise. A Hamming filter is illustrated in FIG. 13C.

While the definitions of these filters are well known in the art, they are repeated next for convenience. For all the filter definitions given below, N is the number of the filter elements, where it is assumed that they run between $1 \leq i \leq N$. Information on other tapered filters can be found in standard signal processing references, such as "Handbook for Digital Signal Processing", Edited by Sanjit Mitra and James Kaiser, Wiley & Sons, Inc. 1993. The content of this reference relevant to filter design is hereby incorporated by reference for background.

1. BCn. BoxCar filter with N points. The filter coefficients are given by $$f_i = \frac{1}{N}$$

2. Cn. Comb filter with N points. The filter coefficients are given by
$\theta_i=0.5$ for i=1 and i=N and 0.0 otherwise 3. HMn. Hamming filter with N points. The filter coefficients are given by $$f_i = 0.54 - 0.46 \cos\left[\frac{2\pi(i-1)}{N-1}\right]$$

The overall effect of the Comb filter and the tapered filter can be analyzed by considering the Fourier transform of their convolution. Comparison of the current and proposed methodologies based on their Fourier transforms is illustrated below. It should be noted that Filter 1 and Filter 2 in accordance with this invention need not necessarily be separate and distinct entities—in specific implementations they could be built into a single filter that has the response corresponding to the convolution of the two separate filters. For reasons of conceptual simplicity, the two filters are considered as being separate in the sequel.

Filter Response Comparison

Assume a hypothetical case where 16 CPMGs must be stacked to satisfy the $\sigma_n$ of about 1 condition. The response of the proposed approach in accordance with the present invention is compared to the response of the conventional boxcar filter in three separate cases simulating:

1. Dual-frequency MRIL-C, non-dithered activation (C3HM16),
2. Dual-frequency MRIL-C, dithered activation (C5HM16),
3. MRIL-Prime (C9HM16).

Case 1: BC16 vs. C3HM16

Figure 14:
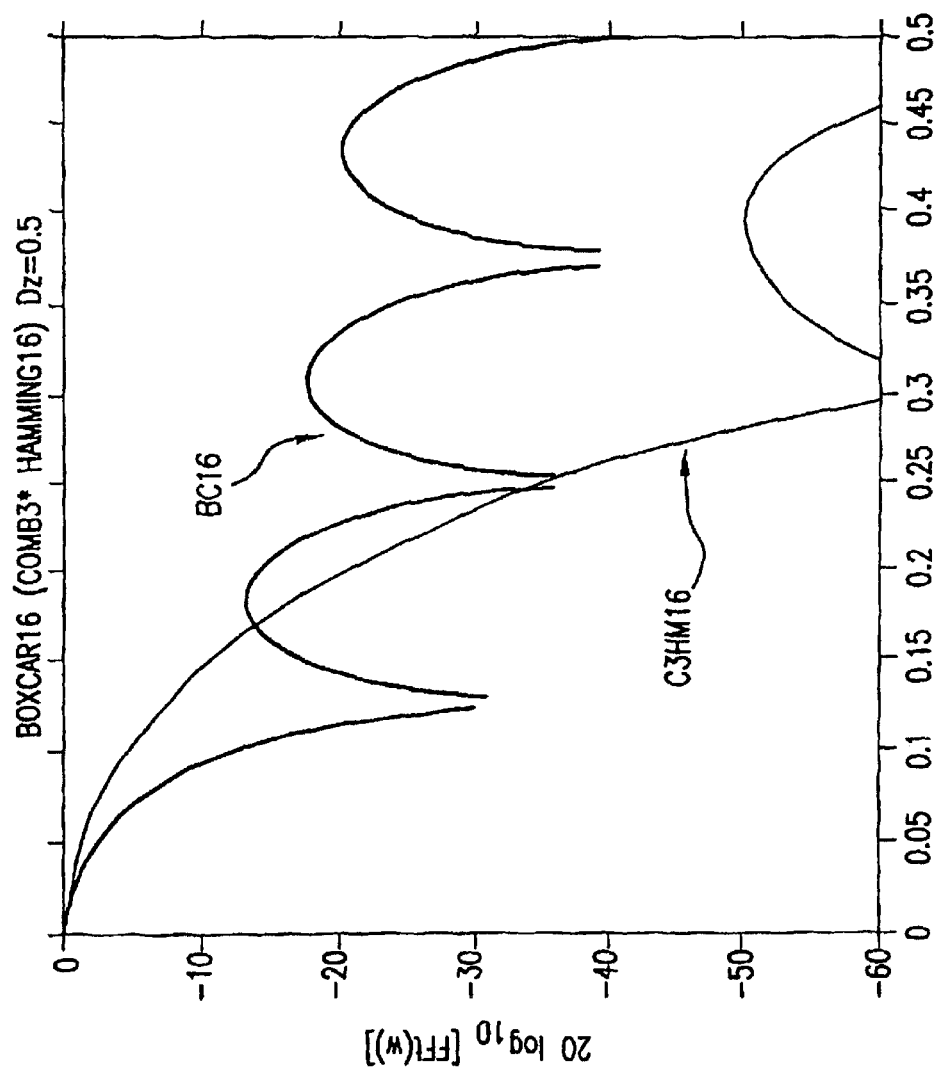
FIGS. 14 through 18 illustrate comparisons between the frequency response of box car filters used in the prior art with combination filters used in accordance with the present invention.

In the case of a dual-frequency MRIL-C tool, with a non-dithered activation, a Ccomb filter of length 3 is followed by a Hamming filter of length 16. The comparison of BC16 vs. C3HM16 is given in FIG. 14. As shown, the BC16 filter has a notch at k=0.125, and two peaks at k=0.175, and k=0.32, all generating noise in a visible range. The C3HM16 filter on the other hand monotonically decreases, has no significant notches, or secondary visible peaks. There is a significant improvement in the vertical resolution, with almost no side-lobe noise.

Case 2: BC16 vs. C5HM16

Figure 15:
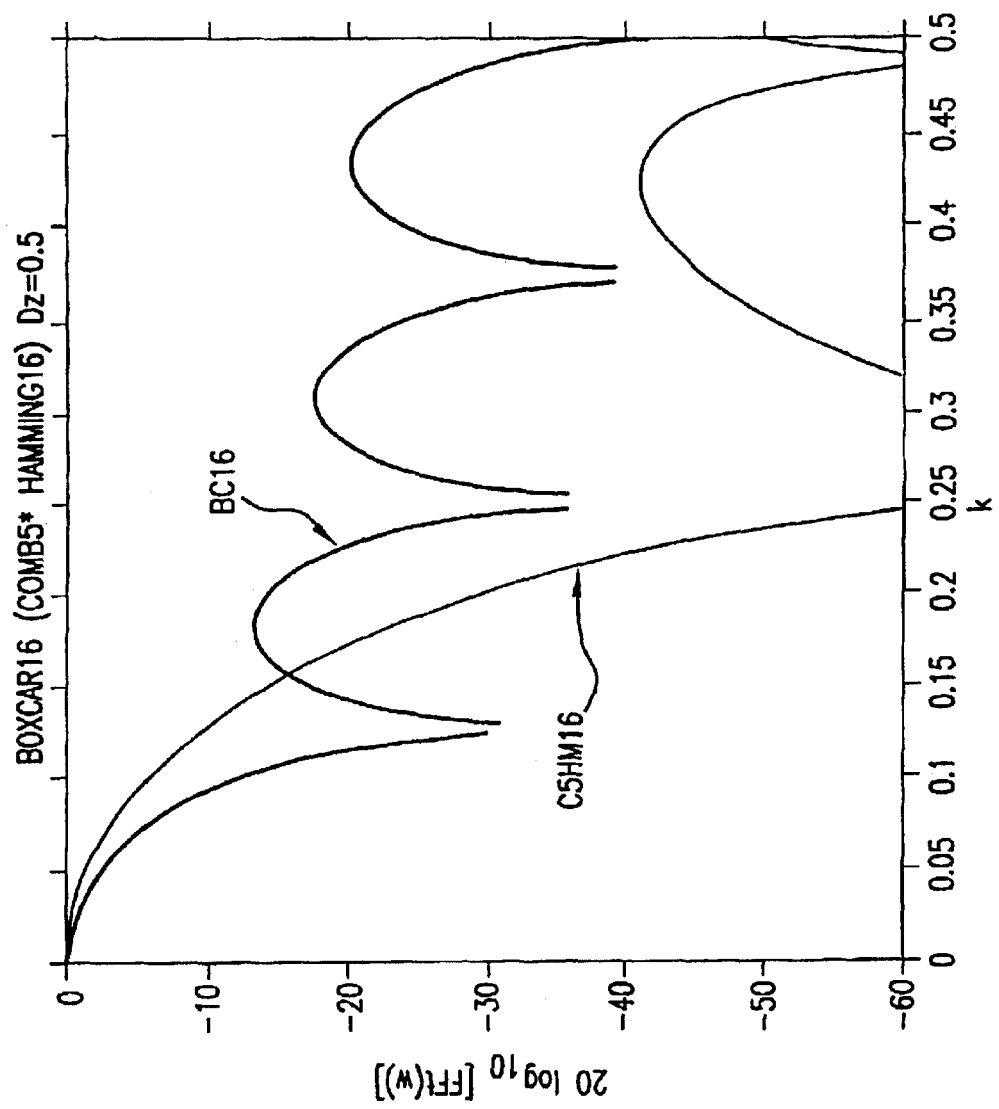

In the case of a dual-frequency MRIL-C tool with dithered activation, a comb filter of length 5 is followed by a Hamming filter of length 16. The comparison of BC16 vs. C5HM16 is given in FIG. 15. The C5 HM16 filter decreases monotonically, as in FIG. 14. Although the boxcar filter may appear to contain a larger proportion of the wavelengths around k=0.18, the notch followed by a peak causes oscillations in the logs. The first notch of the C5HM16 filter occurs at a later spatial-frequency, improving vertical resolution, and the following side-lobe is much smaller compared to the boxcar filter, resulting in significantly reduced side-lobe noise.

Case 3: BC16 vs. C9HM16

Figure 16:
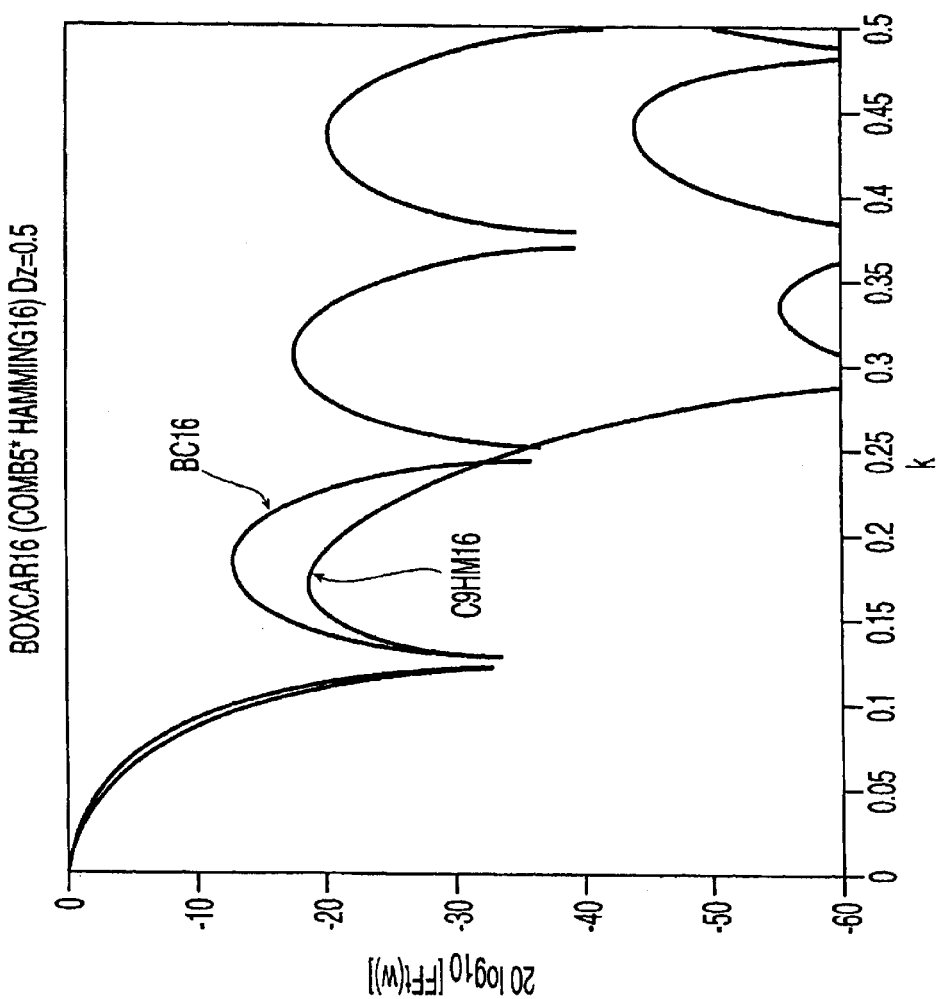

In the case of an MRIL-Prime tool, a comb filter of length 9 is applied before a Hamming filter of length 16. The comparison of BC16 vs. C9HM16 is given in FIG. 16. Both filters have similar responses up to the first notch, explaining why the proposed method may not improve vertical resolution in this particular instance. However, the C9HM16 filter generates a less-noisy response (by approximately 6 dB), since its main side-lobe is weaker compared to the BC16 filter. The second peak of the C9HM16 filter is not as strong as that of the BC16. Although this may imply better resolution on the part of the BC16 filter, the stronger second peak is actually a source of noise that can be observed on the logs. The more suppressed second peak of the C9HM16 response results in a cleaner response.

Filter Response Comparison for Longer Filter Lengths

Figure 17:
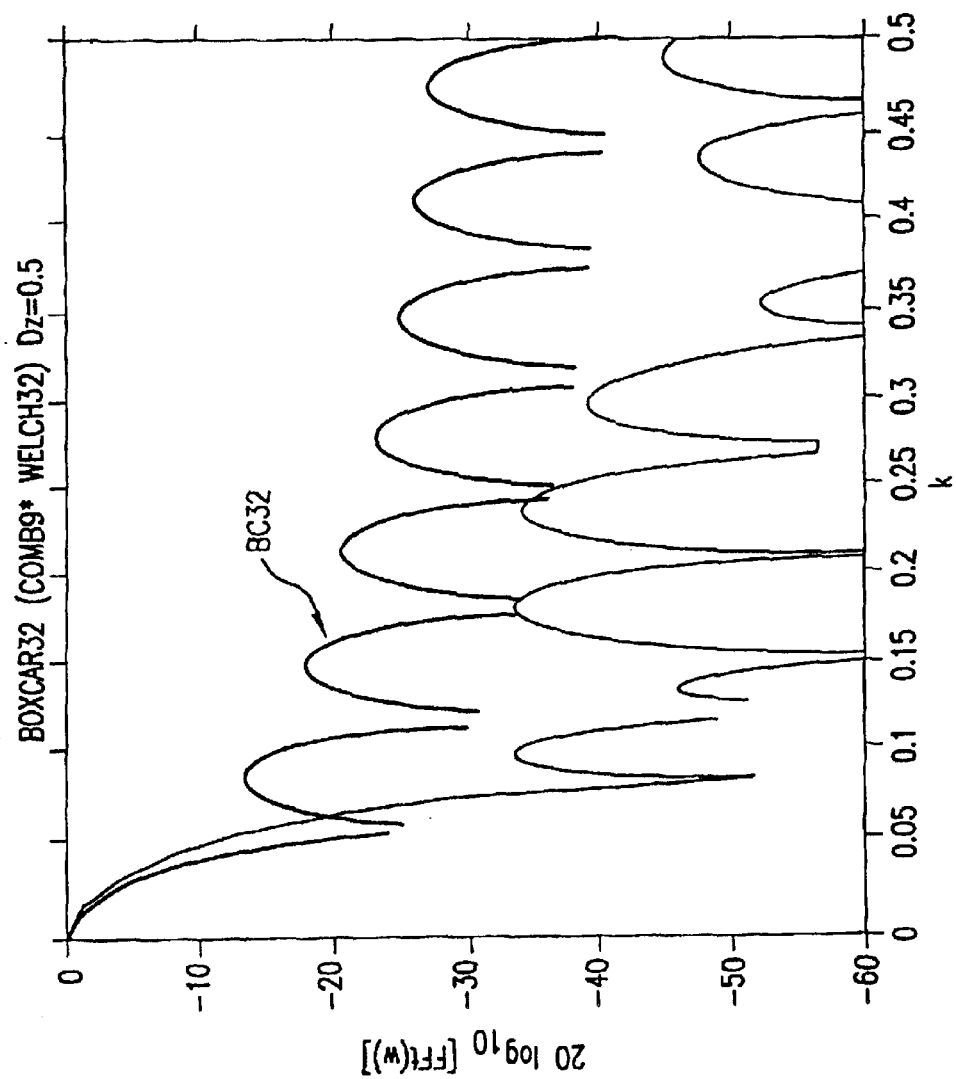
Figure 18:
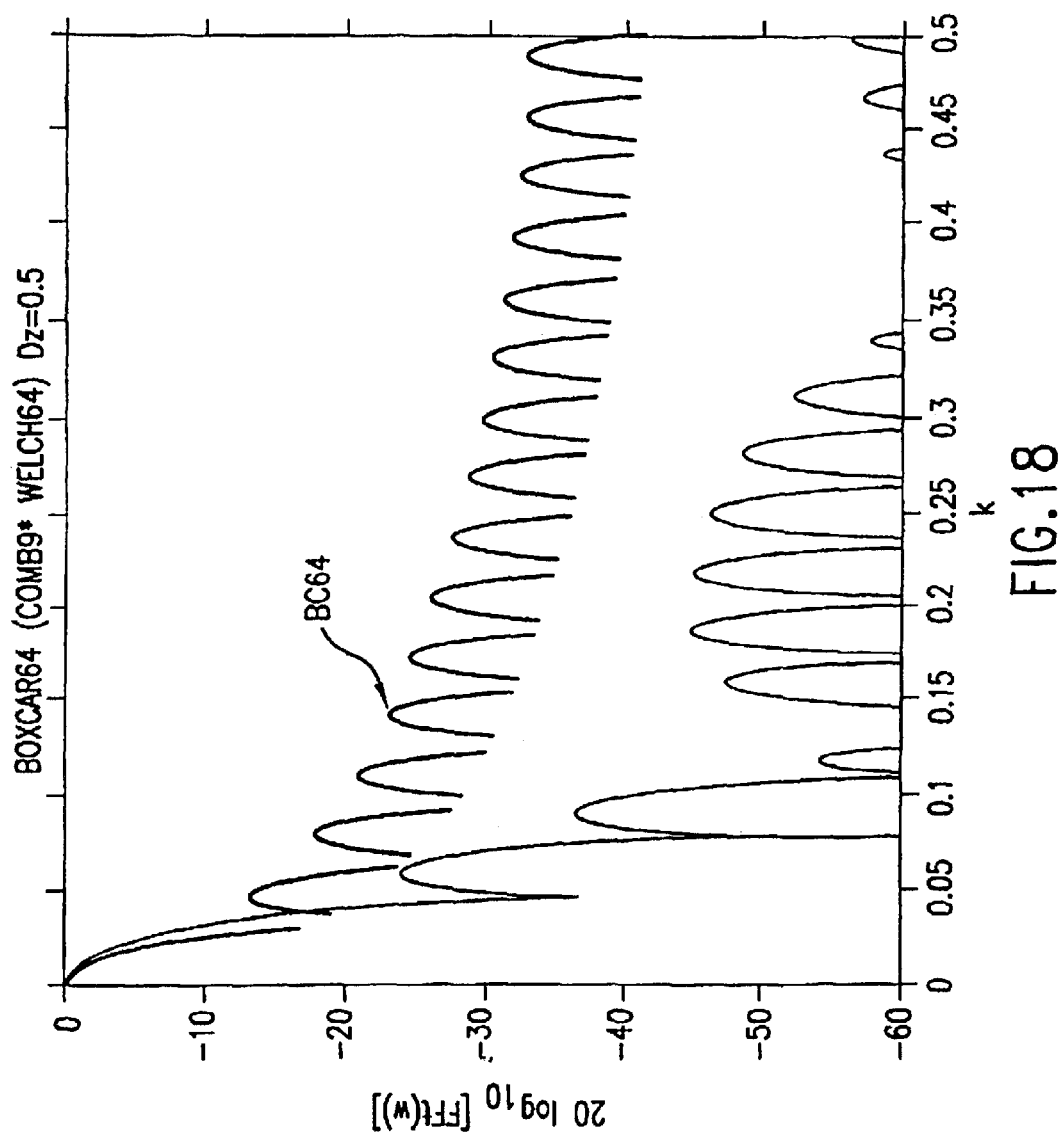

Filter responses for BC32 and BC64, vs. C9HM32 and C9HM64, respectively, can be seen in FIGS. 17 and 18. As the RA gets larger, the locations of the first notch in both filters converge. However, the secondary peak in the C9HM32 or C9HM64 filters is much weaker, resulting in cleaner log response. As illustrated in FIG. 17 for a comparison of BC32 and C9HM32 filters, the notch in the CM9HM32 filter occurs at a higher spatial-frequency, thereby increasing the inherent vertical resolution. Also note the weaker side-lobe (compared to C9HM32), after the first notch.

FIG. 18 illustrates a comparison of the BC64 and C9HM64 filters. The inherent vertical resolution of the C9HM64 filter clearly is better, since the first notch occurs at a higher spatial-frequency compared to the BC64 filter.

Log Examples

Non-dithered MRIL-C Log

Figure 19:
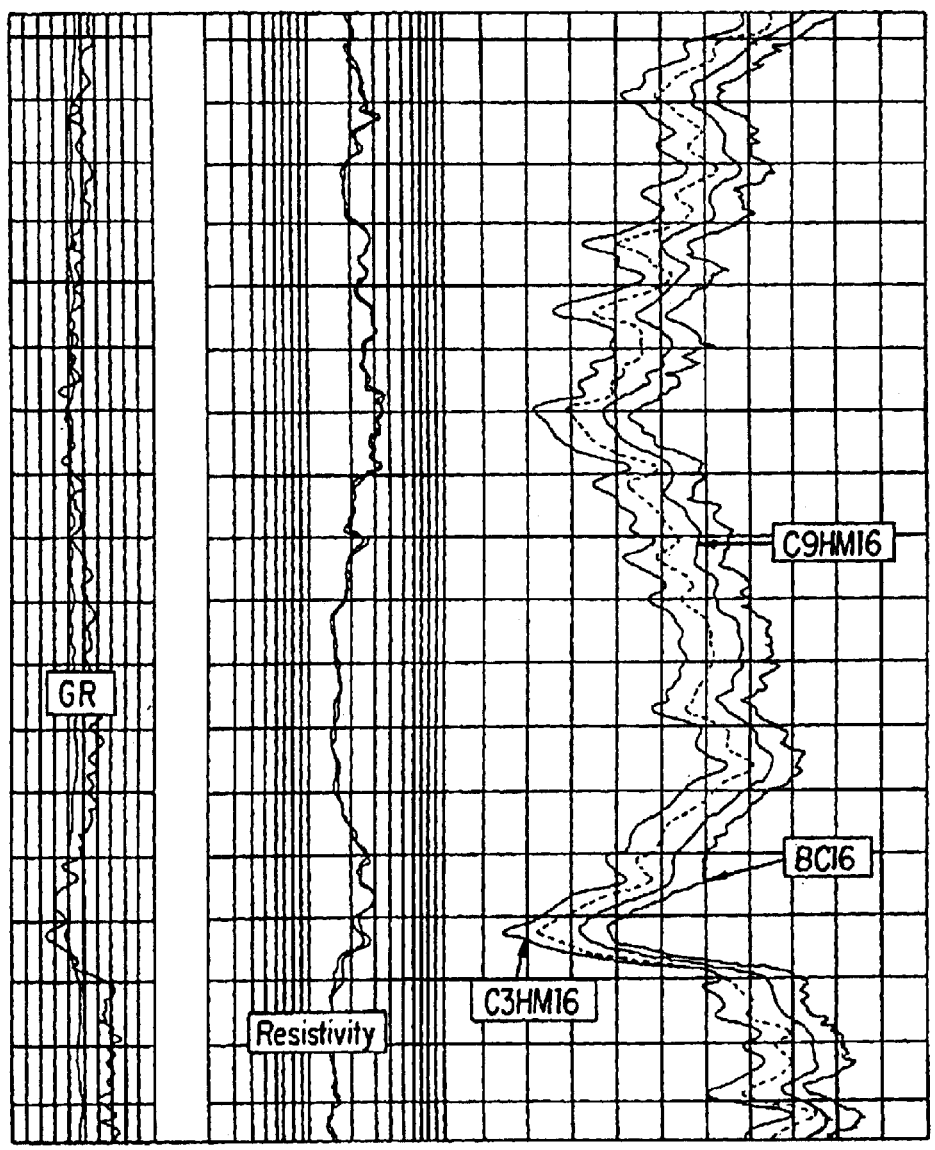
FIG. 19 illustrates the application of four filters, to a 1995-vintage, dual-frequency MRIL-C log.

The four filters, BC16, C3HMN16, C5HM16, and C9HM16 were applied to a 1995-vintage, dual-frequency MRIL-C log. The activation used at the time was not dithered. The results of the four filters can be seen in FIG. 19. The logs have been offset by a constant amount to allow easier visual identification of the features. Porosity from the conventional BC16 process is the red curve, easily identified by jittery noise. The black curve corresponds to the C3HM16 filter, which has the best vertical resolution and the most stable appearance. The other two curves, corresponding to C5HM16 and C9HM16 filters, are also better than the BC16 case, but not as good as the C3HM16 filter. Note the excellent agreement between the theory and the results.

MRIL-C Log, BA Test Well, 6 Second Wait Time

Figure 20:
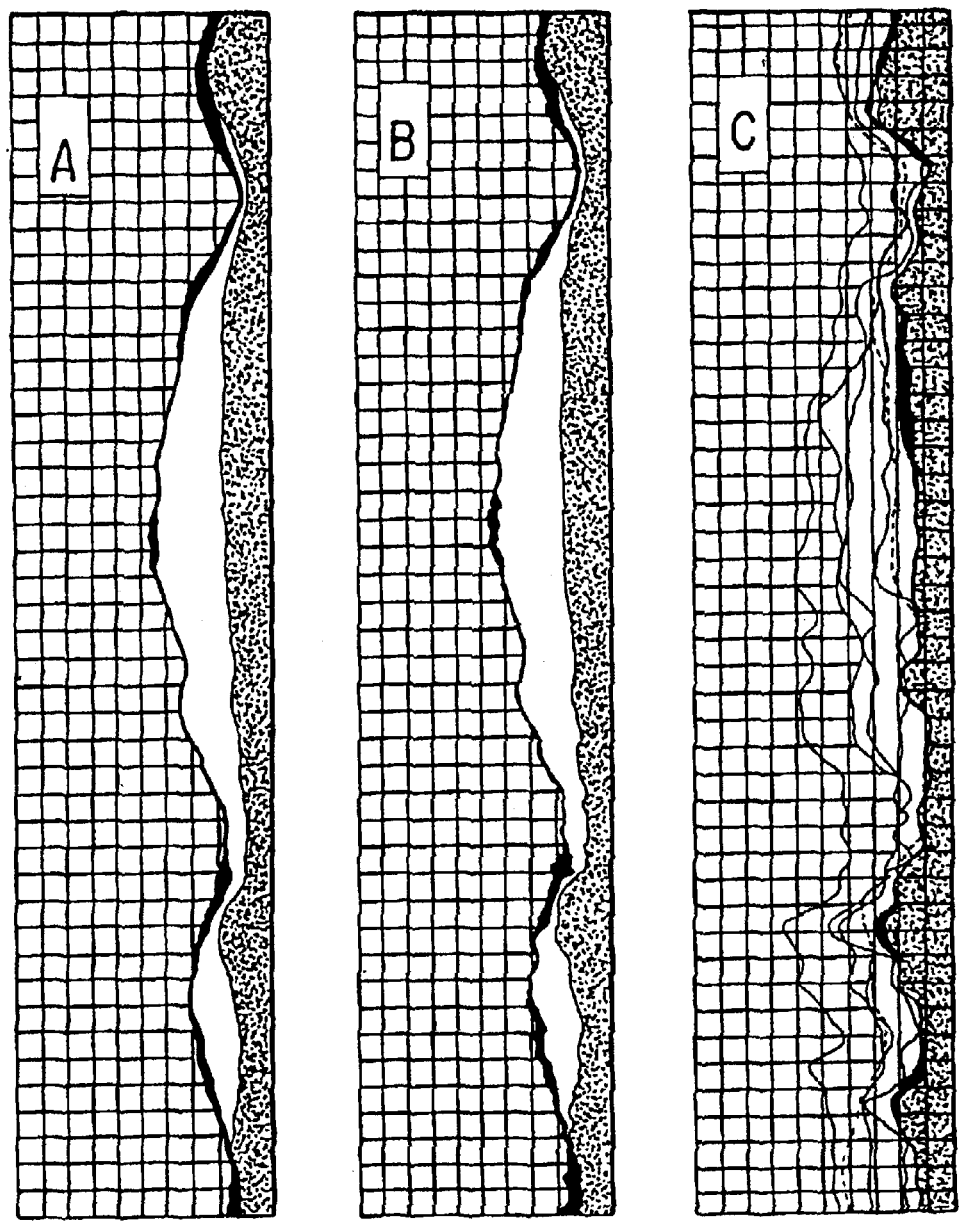
FIGS. 20 and 21 show a comparison of standard processing, versus the method of this invention, in a Baker-Atlas well, MRIL-C log, 6 and 3 second wait time, respectively.
Figure 21:
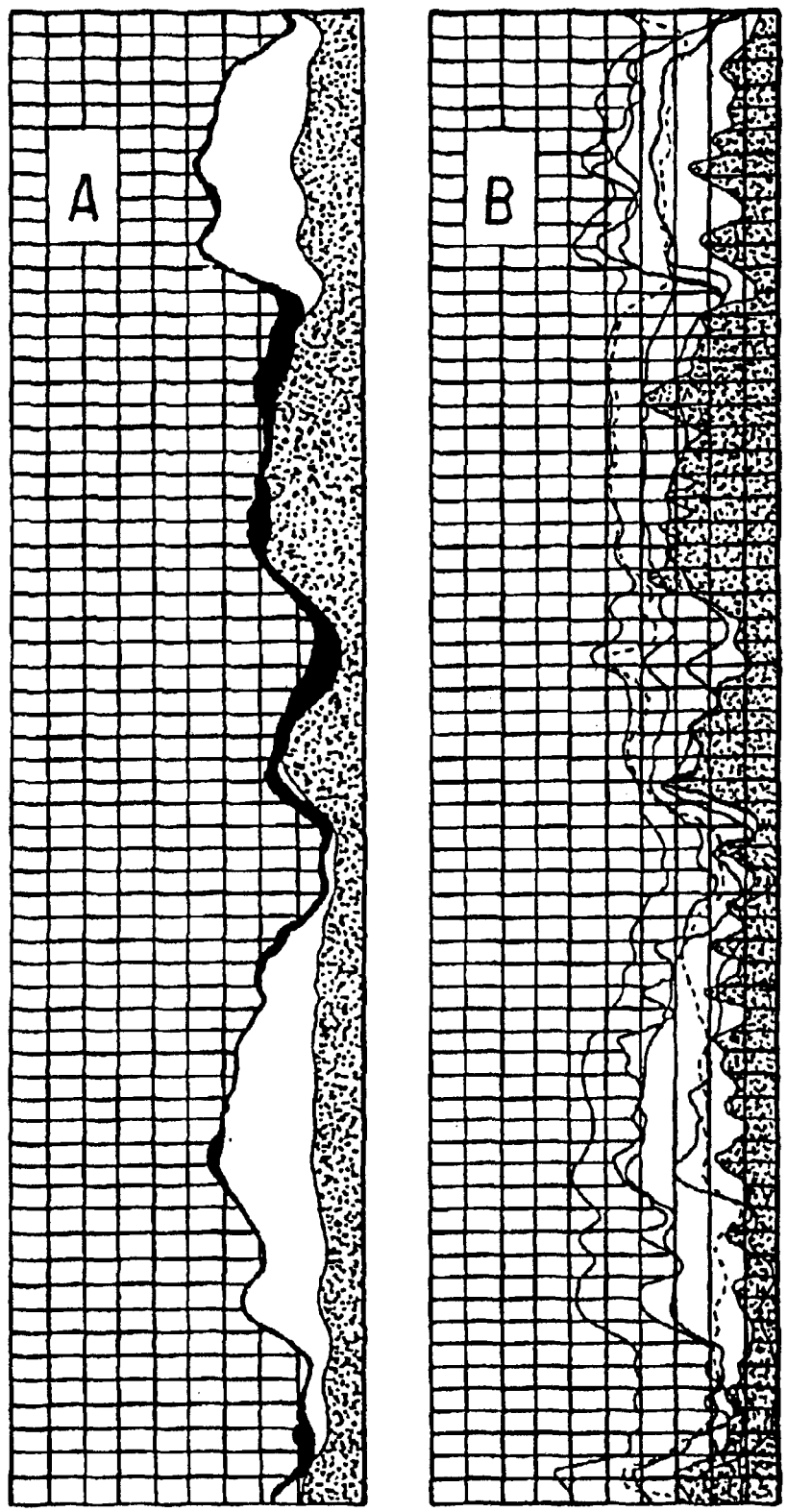

A comparison of standard processing, vs. the method of this invention, in a Baker-Atlas well are shown in FIGS. 20 and 21. Log A is standard MRIL boxcar processing, with a post-inversion cosine filter applied, while B is the same log without the cosine filter. Log C shows results from the new method, with clear improvements in vertical resolution. FIG. 20 is a Baker-Atlas Test Well, MRIL-C log, 6 second wait time. FIG. 20(A) illustrates standard MRIL boxcar processing with post-inversion cosine filter; FIG. 20(B) is the same as (A), without the cosine filter; and FIG. 20(C) illustrates the new method. While porosities in FIGS. 20(A) and (B) contain contributions from the PR06 data set, the porosity log in (C) has been obtained only from the $t_e$=1.2 ms data set.

MRIL-C Log, BA Test Well, 3 Second Wait Time

A comparison of the logs, in the same well, but with a wait time of 3 seconds is shown in FIG. 21. FIG. 21(A) is the standard processing, FIG. 21(B) illustrates the new method. As in the previous figure, the porosity curve in (B) has been obtained from the 1.2 ms data set only. The logging speeds in FIGS. 20 and 21 are close, such that the reduction in the wait time, when using similar stacking levels, results in improved vertical resolution, independent of the method. The zone shown in FIG. 21 covers the same sand in the previous figure, and another shorter zone above it.

Based on the above examples, the following observations can be made: an alternative pre-processing method has been developed to improve the vertical resolution of NMR logs. The methods proposed in Section D replace the boxcar filter with the combination of a comb filter, and a tapered filter, and is equally applicable to a variety of multi-frequency tools.

Next, overall the filter response of the method of this invention is less noisy than the boxcar filter. The side-lobes in the filters (after the first notch) are alternately anti-phase and in-phase with the main-lobe. Consequently, the first side-lobe contributes a strong signal out of phase with the true signal. Hence, a strong first side-lobe will generate appreciable noise (as in the case of boxcar filters), while weaker side-lobes (as in the case of the proposed method) will result in much cleaner response. Indeed, it appears likely that noise originating from the first side-lobe of the boxcar filter is what necessitates the additional application of a cosine filter in the post-inversion phase of the current processing.

In low SNR conditions, where RA*MRA, the proposed method can significantly enhance the vertical resolution of both the MRIL-C and MRIL-D tools, while significantly reducing filter side-lobe noise.

In high SNR conditions (such as oil-based mud, high frequency operation, etc.), the proposed method can significantly enhance the vertical resolution of MRIL-C logs. The improvements are more dramatic in the case of non-dithered activations.

Although a Hamming filter has been used in a specific embodiment illustrated in the drawings, a large selection of filters exists in literature, which can be used in alternate embodiments, dependent on the particular application and ease of implementation.

D.3 Implementation Issues

Figure 22:
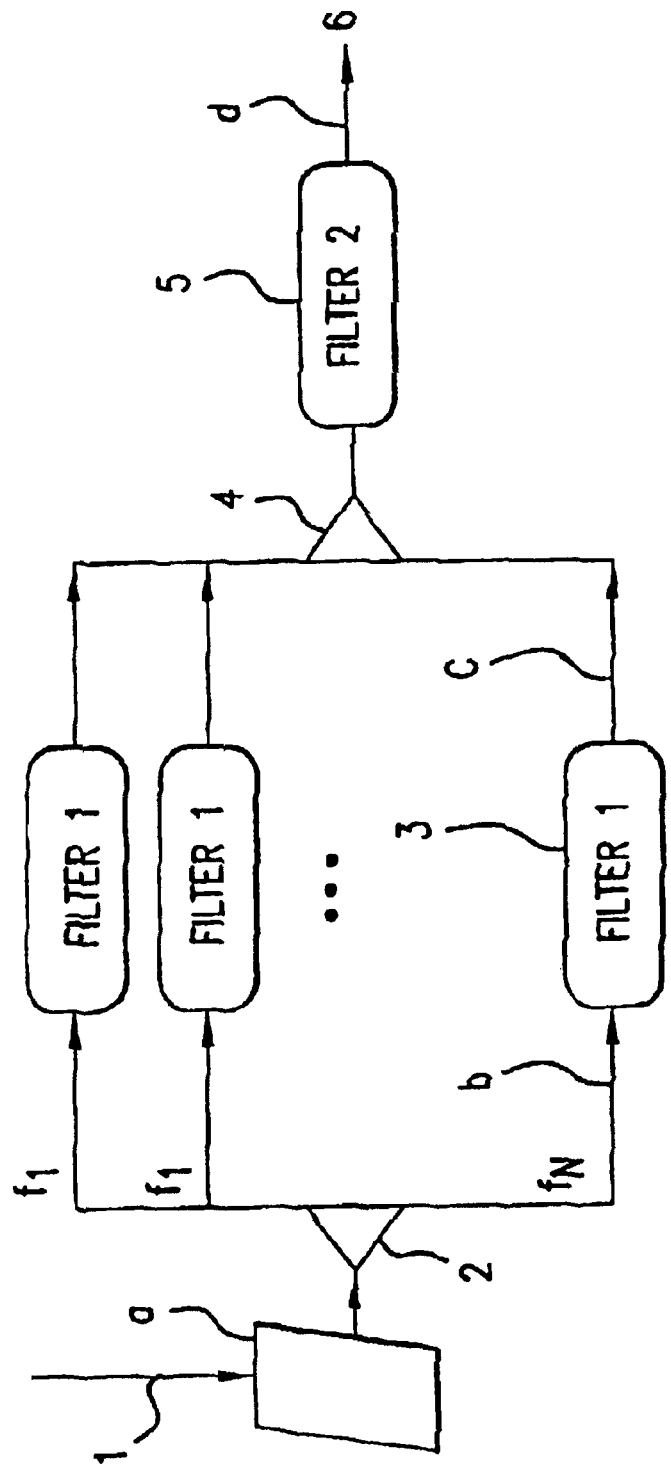

FIGS. 22, 23 and 24 illustrate in more detail the implementation of the method of the present invention discussed in Section D of the disclosure. More specifically, FIG. 22 illustrates in a flow-diagram form the use of two filters to replace the single boxcar filter employed by the prior art.

As illustrated in FIG. 22, the first step 1 is of acquisition & storage of a depth-varying sequence of multi-frequency PAP echo trains, which are designated in the figure for purposes of illustration as echo trains "a". In the following step of the method the multi-frequency echo-trains input signal is separated into multiple data-flow paths, one path per frequency, resulting in N data flow paths, corresponding to the operating frequencies of the tool.

In the following step 3 of the processing algorithm, Filter 1 is applied separately to the data "b" in each data-flow path, producing as the output from each path a sequence of "clean" echo-trains "c" referenced to the mid-point of each echo-train PAP. In the context of this application "clean" denotes that the echo trains no longer contain the non-formation signals that the PAP method or the methods discussed in Sections A, B and C of this application are designed to remove.

In the following step 4 of the method, the separate data-flow paths are re-combined into a single data-flow of the clean echo trains; in the following step 5, Filter 2, as discussed above, is applied to the sequence of clean echo-trains in this recombined data-flow path.

Subsequent processing of the clean echo-trains "d" using standard procedures, such as MAP inversion, is applied as known in the art.

With reference to FIG. 23, an alternative embodiment of the present invention can be used, where the processing modification would allow the user to obtain, for example, the best possible inversions at multiple depths of investigation (lower frequency=>deeper investigation per MRIL design). In particular, and with further reference to the discussion concerning FIG. 22, step 4 of re-combining the data paths is eliminated, so that a separate filter is applied to each data path, as shown in FIG. 23A. In accordance with this embodiment further illustrated in FIG. 23B, a Filter 2' (designed in the same manner as Filter 2 discussed above) is applied to obtain optimum vertical resolution for a given SNR—even though the data is much sparser than with the recombined echo-trains—and to produce multiple frequency-separated clean echo trains "e" with optimum vertical resolution for the required SNR. Subsequent processing of the frequency-separated clean echo-trains using standard procedures is applied, as known in the art.

Figure 24A:
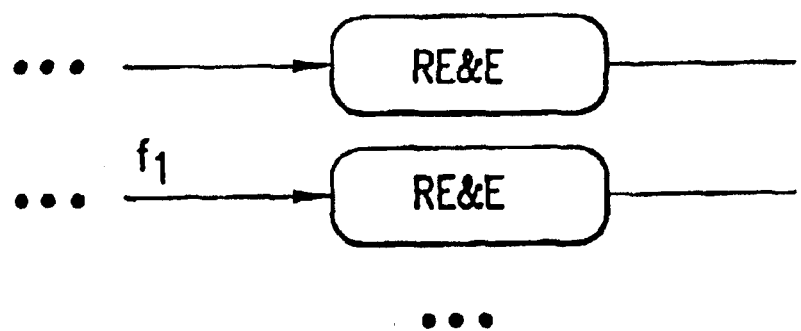
Figure 24B:
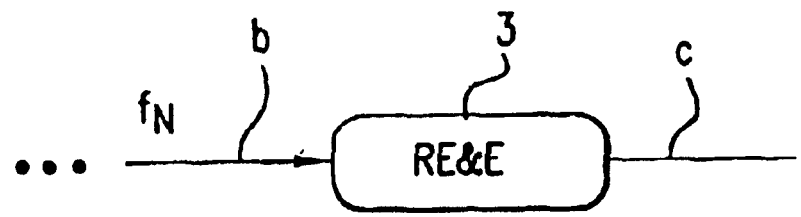

With reference to FIGS. 24A and 24B, in an alternative embodiment, the filtering in Step (3) could be replaced by (3') the data-driven determination of the ringing signal with subsequent removal from the echo-trains. Data driven determination of the ringing signal is discussed in more detail in Section A of this application. [RE&E—Ringing Estimation & Elimination]. Subsequent processing can be either with steps (4), (5) and (6), or with steps (5') and (6'), as described previously, or with other methods not explicitly described.

F. Overall System and Method Considerations

In accordance with the present invention, and as also indicated above, the methods disclosed in Sections A, B, C and D can be used advantageously in combination. It is noted first that the method in Section D, can be used to replace boxcar filtering in all practical applications. In the more special case when the SNR of the formation data is sufficiently high, it can be supplemented with processing of the type discussed in Sections A–C.

More specifically, in a preferred embodiment a NMR system for data logging and analysis is operated as follows. First, the method disclosed in Section D is initially applied and used to estimate the SNR, which is obtained from the input data. Next is determined if the vertical-resolution is sub-optimal and, if so, the processing is switched to the ringing estimation method discussed in Sections A–C.

In an alternative embodiment, one can start by using the Direct Ringing Estimation approach discussed in Section A.1.b; based on the results from this step one can then estimate what filter length is needed to obtain adequate SNR. If the estimated filter length is consistent with the approach discussed in Section D, the operation is switched for this processing.

In general, it will be noted that the filtering approach disclosed in Section E is robust, as it does not make any assumptions about the ringing signal other than that it is essentially unchanged between any two echo-trains that make up a PAP. The estimation of ringing, on the other hand, makes some assumptions about the ringing signal, which in the preferred embodiment is quite simple, i.e., that the ringing signal is characterized by an offset (in the complex space) to the real and imaginary components in the NMR signal, which remain essentially unchanged between any two echo-trains that make up a PAP.

The combination discussed above is believed to be a significant contribution to the art of NMR logging with wide ranging applications involving virtually all NMR tools, and a broad range of practical applications, including logging while drilling.

While the invention has been described with reference to the preferred embodiments, it will be appreciated by those of ordinary skill in the art that modifications can be made to the structure and form of the invention without departing from its spirit and scope, which is defined in the following claims.

What is claimed is:

1. A method for nuclear magnetic resonance (NMR) measurement of petrophysical properties of an earth formation, comprising:

providing at least one first plurality of NMR pulses having at least one excitation and at least one refocusing pulse followed by a de-phasing delay and further followed by at least one test excitation pulse and at least a test refocusing pulse; and receiving at least one first signal in response to the at least one first plurality of NMR pulses; and combining the received at least one first signal with a second signal to reduce ringing error; wherein a second plurality of NMR pulses is generated at a second frequency, $F_2$, which is different from a frequency, $F_1$, of the at least one first plurality of NMR pulses, to generate the second signal, and wherein the difference between the first and second frequencies is given by $$|F_1 - F_2| = \left(n + \frac{1}{2}\right)\frac{1}{2\tau},$$

wherein n is an integer, and τ is an inter echo spacing.

2. The method of claim 1, wherein n is zero.

3. The method of claim 1, wherein n is $\geq 1$.

4. A method for nuclear magnetic resonance (NMR) measurement of petrophysical properties of an earth formation, comprising:

providing at least one first plurality of NMR pulses having at least one excitation and at least one refocusing pulse followed by a de-phasing delay and further followed by at least one test excitation pulse and at least a test refocusing pulse; and receiving at least one first signal in response to the at least one first plurality of NMR pulses; and combining the received at least one first signal with a second signal to reduce ringing error; wherein the difference between the first and second frequencies is given by $$|F_1 - F_2| = \left(n + \frac{1}{2}\right)\frac{1}{2\tau},$$

wherein n is an integer, and τ is an inter echo spacing, wherein pulses at the first frequency $F_1$ are interleaved with pulses at the second frequency $F_2$, wherein echoes from the interleaved pulses are processed to generate a difference signal between a first echo, corresponding to a first recovery time, and a second echo, corresponding to a second recovery time, and wherein the second recovery time is selected to cause substantial loss of signals associated with one or more of a gas phase, a water phase, and an oil phase in the geological formation.

5. The method of claim 1, wherein at least two consecutive pulses at the first frequency $F_1$ are followed by at least two consecutive pulses at the second frequency $F_2$.

6. The method of claim 1, wherein the first and second echo in the difference signal substantially correspond to a single depth mark.

7. The method of claim 1 further comprising providing a fifth plurality of NMR pulses corresponding to a third frequency $F_3$, wherein the first frequency $F_1$ and third frequency $F_3$ correspond to non-overlapping resonant volumes in the geologic formation.

8. The method of claim 1, wherein the at least one first plurality of NMR pulses comprises at least two pulses separated by a variable recovery time selected to substantially reduce signals associated with one or more of a gas phase, a water phase, and an oil phase in the geological formation.

9. The method of claim 8, wherein the at least one second plurality of NMR pulses comprises at least two pulses separated by the variable recovery time.

10. The method of claim 1, wherein the generated at least one broadband saturation pulse and the at least one first plurality of pulses, are according to a pulse sequence defined as:

(broadband saturation)–$T_{sr}$–$(\pi/2)_X$–[τ–$(\pi)_Y$–τ–echo]

where $T_{sr}$ is saturation-recovery time, $(\pi/2)_X$ is an excitation pulse, τ is a time delay, $(\pi)_Y$ is a refocusing pulse, echo is the acquisition of a pulse echo, [ . . . ] denotes repeating the indicated pulses, measurements, or delays contained inside one or more times.

11. The method of claim 10, wherein the pulse sequence is modified as follows:

(broadband saturation) – $T_{sr}$ – $(\pi/2)_X$ – [τ – $(\pi)_Y$ – τ – echo] – $\left(N + \frac{1}{2}\right)\tau - (\pi/2)_x - 2\tau - acq_x - \tau - (\pi)_y - \tau - acq_y$, where (N+1/2)τ is a delay and N is an integer, $(\pi/2)_x$ is a test excitation pulse, $acq_x$ represents acquisition of π/2 ringing data, $(\pi)_y$ is a test refocusing pulse, and $acq_y$ denotes acquisition of π ringing data.

12. The method of claim 11 further comprising the step of repeating the pulse sequence for phase alternation, by replacing the $(\pi)_Y$ and $(\pi)_y$ pulses by $(\pi)_{-Y}$ and $(\pi)_{-y}$, respectively.

13. The method of claim 12 further comprising the step of repeating the pulse sequence at frequency $F_2$.

14. The method of claim 13 further comprising the step of combining received echoes from the pulse sequences at frequencies $F_1$ and $F_2$.

15. The method of claim 14 further comprising the step of estimating an efficiency measure of non-formation signal cancellation in the combined received echoes from the pulse sequences at frequencies $F_1$ and $F_2$ following the (N+1/2)τ delay.

16. A method for determination of petrophysical properties of a volume of earth formation in a borehole using an NMR tool, the method comprising the steps of:
providing a static magnetic field in said volume of earth;
providing oscillating magnetic fields in said volume of earth formation, to detect echoes thereto as an induced signal, according to pulse sequence comprising a first set of CPMG pulses associated with a pulse echo spacing $\tau_1$ and a second set of CPMG pulses associated with a pulse echo spacing $\tau_2$, shorter than $\tau_1$; and
processing the induced signal with additional induced signals to determine petrophysical properties of the volume of earth formation, wherein data, the data comprising the induced signal and the additional induced signals, is acquired in at least two orthogonal channels.

17. A method for making nuclear magnetic resonance (NMR) measurements of a geologic formation using an NMR logging tool, comprising the steps of:
providing a static magnetic field in the a volume of the formation;
applying oscillating magnetic fields according to at least one modified CPMG pulse sequence characterized by at least one first echo spacing TD and a second echo spacing TE; wherein the at least one first echo spacing TD is selected to correspond to diffusion characteristics of fluids in the formation and cause corresponding amplitude loss in induced NMR echo signals, and TE is relatively short, such that diffusion in the corresponding induced NMR echo signals is substantially negligible;
measuring the induced NMR echo signals;
determining the amount of amplitude loss resulting from at least one TD interval; and
computing diffusion properties of fluids in the formation based on the determined amplitude loss.

18. The method of claim 17, wherein the modified CPMG sequence is repeated with at least one first echo spacing TD≧TE.

19. The method of claim 17, wherein the at least one TD is selected to cause loss of signals associated with one or more of a gas phase, an oil phase, and a water phase to derive petrophysical properties of the geological formation.

20. The method of claim 17 further comprising the step of estimating diffusivity values for gas, water and oil phases in the formation, and selecting values for the TD and TE echo spacings based on the estimated diffusivity values.

21. The method of claim 20, wherein the selection of values for the TD and TE echo spacings is based on forward-modeling of signal components to achieve maximum contrast between fluid phases.

22. A system for increasing the resolution of NMR log data obtained using a multi-frequency NMR tool having N operating frequencies, comprising:
means for providing a NMR pulse echo signal comprising components corresponding to at least two operating frequencies of the tool;
means for separating the provided pulse echo signal into two or more data-flow paths, each data flow path corresponding to an operating frequency of the tool;

means for processing the signal in each data flow path separately to remove coherent noise components;

means for combining output signals from the separately processed data flow paths to remove random noise components; and means for estimating residual coherent noise.

23. The system of claim 22 further comprising means responsive to a residual coherent noise estimate for initiating additional noise reduction by stacking at least one more signal.

* * * * *